US007653491B2

(12) United States Patent
Schadt et al.

(10) Patent No.: US 7,653,491 B2
(45) Date of Patent: Jan. 26, 2010

(54) COMPUTER SYSTEMS AND METHODS FOR SUBDIVIDING A COMPLEX DISEASE INTO COMPONENT DISEASES

(75) Inventors: Eric E. Schadt, Kirkland, WA (US); Stephanie A. Monks, Stillwater, OK (US)

(73) Assignee: Merck & Co., Inc., Whitehouse Station, NJ (US)

( * ) Notice: Subject to any disclaimer, the term of this patent is extended or adjusted under 35 U.S.C. 154(b) by 252 days.

(21) Appl. No.: 10/515,804

(22) PCT Filed: May 20, 2003

(86) PCT No.: PCT/US03/15768

§ 371 (c)(1),
(2), (4) Date: Jan. 24, 2006

(87) PCT Pub. No.: WO03/100557

PCT Pub. Date: Dec. 4, 2003

(65) Prior Publication Data

US 2006/0122816 A1 Jun. 8, 2006

Related U.S. Application Data

(60) Provisional application No. 60/382,036, filed on May 20, 2002, provisional application No. 60/460,304, filed on Apr. 2, 2003.

(51) Int. Cl.
*G06F 19/00* (2006.01)
*G11C 17/00* (2006.01)
*G06F 15/00* (2006.01)

(52) U.S. Cl. ................. 702/20; 365/94; 700/1
(58) Field of Classification Search ............. None
See application file for complete search history.

(56) References Cited

U.S. PATENT DOCUMENTS

| | | | |
|---|---|---|---|
| 5,075,217 A | 12/1991 | Weber | |
| 5,324,631 A | 6/1994 | Helentjaris et al. | |
| 5,510,270 A | 4/1996 | Fodor et al. | |
| 5,569,588 A | 10/1996 | Ashby et al. | |
| 5,578,832 A | 11/1996 | Trulson et al. | |
| 5,965,352 A | 10/1999 | Stoughton et al. | |
| 6,132,969 A | 10/2000 | Stoughton et al. | |
| 6,132,997 A | 10/2000 | Shannon | |
| 6,165,709 A | 12/2000 | Friend et al. | |
| 6,218,122 B1 | 4/2001 | Friend et al. | |
| 6,271,002 B1 | 8/2001 | Linsley et al. | |
| 6,324,479 B1 | 11/2001 | Friend et al. | |
| 6,368,806 B1 | 4/2002 | Openshaw et al. | |
| 2002/0094532 A1 | 7/2002 | Bader et al. | |
| 2003/0180761 A1 | 9/2003 | Castonguay et al. | |
| 2003/0224394 A1 | 12/2003 | Schadt et al. | |
| 2006/0241869 A1 | 10/2006 | Schadt et al. | |
| 2007/0038386 A1 | 2/2007 | Schadt et al. | |

FOREIGN PATENT DOCUMENTS

| | | |
|---|---|---|
| WO | WO 99 13107 | 3/1999 |
| WO | PCT/US03/03100 | 2/2003 |
| WO | PCT/US03/15768 | 5/2003 |
| WO | PCT/US03/23976 | 8/2003 |
| WO | WO 03/065282 | 8/2003 |
| WO | PCT/US03/41613 | 12/2003 |
| WO | WO 03/100557 | 12/2003 |
| WO | WO 2004/013727 | 2/2004 |
| WO | PCT/US2004/016917 | 5/2004 |
| WO | WO 2004/061616 | 7/2004 |
| WO | WO 2004/109447 | 12/2004 |
| WO | WO 2005/017652 | 2/2005 |
| WO | WO 2005/107412 | 11/2005 |

OTHER PUBLICATIONS

PCT/US04/17754, International Search Report, dated May 23, 2007.
PCT/US05/15419, International Search Report, dated May 10, 2006.
Lan et al., 2006, "Combined Expression Trait Correlations and Expression Quantitative Trait Locus Mapping," PLoS Genetics, 2, pp. 0051-0061.
U.S. Appl. No. 11/527,145, filed Sep. 25, 2006, Schadt.
U.S. Appl. No. 11/587,900, filed Oct. 27, 2006, Zhu and Schadt.
U.S. Appl. No. 11/985,979, filed Nov. 19, 2007, Schadt.
U.S. Appl. No. 11/986,001, filed Nov. 19, 2007, Schadt.
U.S. Appl. No. 10/558,928, filed Nov. 30, 2005, Schadt et al.
U.S. Appl. No. 10/540,405, filed Jun. 22, 2005, Schadt et al.
U.S. Appl. No. 10/523,143, filed Jan. 31, 2005, Schadt et al.
Aitman et al., 1999, "Identification of Cd36 (Fat) as an insulin-resistance gene causing defective fatty acid and glucose metabolism in hypertensive rats," Nature Genetics 21: 76-83.
Akagi et al., 1996, "Microsatellite DNA markers for rice chromosomes," Theor. Appl. Genet. 93:1071-1077.
Allison et al., 1998, "Multiple phenotype modeling in gene-mapping studies of quantitative traits: power advantages," Am. J. Hum. Genet. 63:1190-1201.
Amos et al., 1990, "A multivariate method for detecting genetic linkage, with application to a pedigree with an adverse lipoprotein phenotype," Am. J. Hum. Genet. 47:247-254.
Barbosa et al., 1976, "The genetic heterogeneity of diabetes : histocompatibility antigens (HLA) in families with maturity-onset type diabetes of the young (MODY) and juvenile, insulin-dependent diabetes (JID) [proceedings]," Diabete. Metab. 2:160.

(Continued)

*Primary Examiner*—John S Brusca
(74) *Attorney, Agent, or Firm*—Jones Day

(57) ABSTRACT

A method for identifying a quantitative trait loci for a complex trait that is exhibited by a plurality of organisms in a population. The population is divided into a plurality of sub-populations using a classification scheme. Depending on what is known about the population, either a supervised or unsupervised classification is used. The classification scheme is derived from a plurality of cellular constituent measurements obtained from each organism in the population. For each sub-population in the plurality of sub-populations, a quantitative genetic analysis is performed on the sub-population in order to identify one or more quantitative trait loci for the complex trait.

333 Claims, 16 Drawing Sheets

OTHER PUBLICATIONS

Blanchard et al., 1996, "Sequence to array: Probing the genome's secrets," Nature Biotechnology 14:1649.

Blanchard et al., 1996, "High-density oligonucleotide arrays," Biosensors & Bioelectronics 11: 687-690.

Bligh et al, 1995, "A microsatellite sequence closely linked to the Waxy gene of *Oryza sativa*," Euphytica 86:83-85.

Bochner et al., 2001, "Phenotype microarrays for high-throughput phenotypic testing and assay of gene function," Genome Res. 11:1246-1255.

Börjeson, 1976, "The aetiology of obesity in children," Acta. Paediar. Scand. 65:279-287.

Bray, 1989, "1989 McCollum Award Lecture. Genetic and hypothalamic mechanisms for obesity-finding the needle in the haystack," Am. J. Clin. Nutr. 50:891-902.

Bray, 1992, "Genetic, hypothalamic and endocrine features of clinical and experimental obesity," Progress in Brain Research 93:333-341.

Brem et al., 2002, "Genetic Dissection of Transcriptional Regulation in Budding Yeast," Science 296:752-755.

Brown et al., 2000, "Knowledge-based analysis of microarray gene expression data by using support vector machines," Proc. Natl. Acad. Sci. USA 97:262-267.

Cheung et al., 2002, "The genetics of variation in gene expression," Nature Genetics Supplement 32: 522-525.

Cheung et al., 2003, "Natural variation in human gene expression assessed in lymphoblastoid cells," Nature Genetics 33: 422-425.

Chirgwin et al., 1979, "Isolation of biologically active ribonucleic acid from sources enriched in ribonuclease," Biochemistry 18:5294-5299.

Cohen et al., 2000, "A computational analysis of whole-genome expression data reveals chromosomal domains of gene expression," Nature Genetics 26:183-186.

Corder et al., 1993, "Gene dose of apolipoprotein E type 4 allele and the risk of Alzheimer's disease in late onset families," Science 261:921-923.

Cox et al., 1999, "Loci on chromosomes 2 (NIDDM1) and 15 interact to increase susceptibility to diabetes in Mexican Americans," Nature Genetics 21:213-215.

DeRisi et al., 1996, "Use of a cDNA microarray to analyse gene expression patterns in human cancer," Nature Genetics 14:457-460.

Doerge, 2002, "Mapping and analysis of quantitative trait loci in experimental populations," Nature Reviews 3:43-52.

Draghici, 2003, "Data Analysis Tools for DNA Microarrays," Chapman & Hall, p. 1-478.

Duda et al., 2001, Pattern Classification, John Wiley & Sons, New York, NY, p. 521-530.

Duda et al., 2001, Pattern Classification, John Wiley & Sons, New York, NY, p. 550-557.

Easton et al., 1993, "Inherited susceptibility to breast cancer," Cancer Surv. 18:95-113.

Eaves et al., 2002, "Combining Mouse Congenic Strains and Microarray Gene Expression Analyses to Study a Complex Trait: the NOD Model of Type 1 Diabetes," Genome Research 12: 232-243.

Egholm et al., 1993, "PNA hybridizes to complementary oligonucleotides obeying the Watson-Crick hydrogen-bonding rules," Nature 365:566-568.

Elowitz et al., 2002, "Stochastic Gene Expression in a Single Cell," Science 297:1183-1186.

Falk et al., 1987, "Haplotype relative risks: an easy reliable way to construct a proper control sample for risk calculations," Ann. Hum. Genet. 51 ( Pt 3):227-233.

Ferguson et al., 1996, "A fiber-optic DNA biosensor microarray for the analysis of gene expression," Nature Biotechnology 14:1681-1684.

Fiehn et al., 2000, "Metabolite profiling for plant functional genomics," Nature Biotech. 18:1157-1161.

Fishel et al., 1993, "The human mutator gene homolog MSH2 and its association with hereditary nonpolyposis colon cancer," Cell 75:1027-1038.

Fodor et al., 1991, "Light-directed, spatially addressable parallel chemical synthesis," Science 251:767-773.

Ford et al., 1994, "Risks of cancer in BRCA1-mutation carriers. Breast Cancer Linkage Consortium," Lancet 343:692-695.

Friedman et al., 1991, "Molecular mapping of obesity genes," Mammalian Genome 1:130-144.

Friedman et al., 1992, "Tackling a weighty problem," Cell 69:217-220.

Froehler et al., 1986, "Synthesis of DNA via deoxynucleoside H-phosphonate intermediates," Nucleic Acids Research 14:5399-5407.

Fulker et al., 1999, "Combined Linkage and Association Sib-Pair Analysis for Quantitative Traits," Am. J. Hum. Genet. 64:259-267.

Fullerton et al., 2000, "Apolipoprotein E variation at the sequence haplotype level: implications for the origin and maintenance of a major human polymorphism," Am. J. Hum. Genet. 67:881-900.

Gaasterland et al., 2000, "Making the most of microarray data," Nature Genetics 24:204-206.

Goffeau et al., 1996, "Life with 6000 genes," Science 274:546-567.

Grunau et al., 2001, "MethDB—a public database for DNA methylation data," Nucelic Acids Research, 29: 270-274.

Grundy et al., 1990, "Metabolic and health complications of obesity," Dis. Mon. 36:641-731.

Haley et al., 1992, "A simple regression method for mapping quantitative trait loci in line crosses using flanking markers," The Genetical Society of Great Britain 69:315-324.

Hayashi et al., 1994, "Detection of additive and dominance effects of QTLs in interval mapping of F2 RFLP data," Theor. Appl. Genet. 87:1021-1027.

Helentjaris et al., 1985, "Restriction fragment polymorphisms as probes for plant diversity and their development as tools for applied plant breeding," Plant Molecular Biology 5:109-118.

Helm et al., 1991, "Classification and identification of bacteria by Fourier-transform infrared spectroscopy," Journal of General Microbiology 137: 69-79.

Hu et al., 1991, "Identification of broccoli and cauliflower cultivars with RPD markers," Plant Cell Reports 10:505-511.

Hughes et al., 2000, "Functional Discovery via a Compendium of Expression Profiles," Cell 102:109-126.

International Human Genome Consortium, 2001, "Initial sequencing and analysis of the human genome," Nature 409:860-921.

James et al., 1998, "Non-alcoholic steatohepatitis (NASH): a disease of emerging identity and importance," Journal of Hepatology 29: 495-501.

Jansen, 1993, "Interval mapping of multiple quantitative trait loci," Genetics 135:205-211.

Jansen, 1994, "Controlling the type I and type II errors in mapping quantitative trait loci," Genetics 138:871-881.

Jansen et al., 2001, "Genetical genomics: the added value from segregation," Trends in Genetics 17:388-391.

Jarvis et al., 1973, "Clustering using a similarity measure based on shared near neighbors," IEEE Transactions on computers C-22:1025-1034.

Jaspers et al., 1982, "Genetic heterogeneity in ataxia-telangiectasia studied by cell fusion," Proc. Natl. Acad. 79: 2641-2644.

Jiang et al., 1995, "Multiple trait analysis of genetic mapping for quantitative trait loci," Genetics 140:1111-1127.

Jin et al., 2001, "The contributions of sex, genotype and age to transcriptional variance in *Drosophila melanogaster*," Nature Genetics 29: 389-395.

Kajiwara et al., 1994, "Digenic Retinitis Pigmentosa Due to Mutations at the Unlinked Peripherin/RDS and ROM1 Loci," Science 264: 1604-1608.

Karp et al., 2000, "Identification of complement factor 5 as a susceptibility locus for experimental allergic asthma," Nature Immunology, vol. 1, No. 3: 221-226.

Kearsey et al., 1994, "QTL analysis: a simple 'marker-regression' approach," Theor. Appl. Genet. 89:698-702.

Knapp et al., 1993, "The haplotype-relative-risk (HRR) method for analysis of association in nuclear families," Am. J. Hum. Genet. 52:1085-1093.

Knoll et al., 1993, "Cytogeneitc and Molecular Studies in the Prader-Willi and Angelman Syndromes: An Overview," Amer. Journal of Medical Genetics 46: 2-6.

Kruglyak et al., 1996, "Parametric and nonparametric linkage analysis: a unified multipoint approach," Am. J. Hum. Genet. 58:1347-1363.

Kruglyak et al., 2001, "Variation is the spice of life," Nature Genetics 27:234-236.

Lance et al., 1967, "A general theory of classificatory sorting strategies," Computer Journal 9:373-380.

Lander et al., 1989, "Mapping Mendelian factors underlying quantitative traits using RFLP linkage maps," Genetics 121:185-199.

Lander et al., 1994, "Genetic dissection of complex traits," Science 265:2037-2048.

Lander, 1996, "The new genomics: Global views of biology," Science 274:536-539.

Levsky et al., 2002, "Single-Cell gene expression profiling," Science 297:836-840.

Lockhart et al., 1996, "Expression monitoring by hybridization to high-density oligonucleotide arrays," Nature Biotechnology 14:1675-1680.

Lynch et al., 1998, "Genetics and Analysis of Quantitative Traits," Sinauer Associates, Inc.: 3-867.

Machleder et al., 1997, "Complex Genetic Control of HDL Levels in Mice in Response to an Atherogenic Diet," J. Clin. Invest. 99:1406-1419.

Manley et al., 1999, "Overview of QTL mapping software and introduction to Map Manager QT," Mammalian Genome 10:327-334.

Martinez et al., 1994, "Missing markets when estimating quantitative trait loci using regression mapping," The Genetical Society of Great Britain 73:198-206.

Maskos et al., 1992, "Oligonucleotide hybridisations on glass supports: a novel linker for oligonucleotide synthesis and hybridisation properties of oligonucleotides synthesised in situ," Nucleic Acids Research 20: 1679-1684.

McBride et al., 1983, "An Investigation of Several Deoxynucleoside Phosphoramidites Useful for Sythesizing Deoxyoligonucleotides," Tetrahedron Letters 24: 245-248.

Moll et al., 1991, "The Genetic and Environmental Sources of Body Mass Index Variability: Te Muscatine Ponderosity Family Study," Am. J. Hum. Genet. 49: 1243-1255.

Mount, 2001, "Genome Analysis," Bioinformatics Sequence and Genome Analysis Chapter 10, p. 479-531.

Naumann et al., 1991, "Microbiological characterizations by FT-IR spectroscopy," Nature 351: 81-82.

Nguyen et al., 1995, "Differential gene expression in the murine thymus assayed by quantitative hybridization of arrayed cDNA clones," Genomics 29:207-216.

Nishina et al., 1994, "Atherosclerosis in genetically obese mice: the mutants obese, diabetes, fat, tubby, and lethal yellow," Metabolism 43:554-558.

Olson et al., 1999, "Tutorial in biostatistics genetic mapping of complex traits," Statistics in Medicine 18:2961-2981.

Patil et al., 2001, "Blocks of limited haplotype diversity revealed by high-resolution scanning of human chromosome 21," Science 294:1719-1723.

Pease et al., 1994, "Light-generated oligonucleotide arrays for rapid DNA sequence analysis," Proc. Natl. Acad. Sci. 91: 5022-5026.

Pericak-Vance et al., 1991, " Linkae Studies in Familial Alzheimer Disease: Evidence for Chromosome 19 Linkage," Am. J. Hum. Genet. 48: 1034-1050.

Prashar et al., 1996, "Analysis of differential gene expression by display of 3' end restriction fragments of cDNAs," Proc. Natl. Acad. Sci. USA 93:659-663.

Reeders et al., 1987, "A study of genetic linkage heterogeneity in adult polycystic kidney disease," Hum. Genet. 76:348-351.

Roberts et al., 2000, "Signaling and Circuitry of Multiple MAPK Pathways Revealed by a Matrix of Global Gene Expression Profiles," Science 287: 873-880.

Sagliocco et al., 1996, "Identification of Proteins of the Yeast Protein Map using Genetically Manipulated Strains and Peptide-Mass Fingerprinting," Yeast 12: 1519-1533.

Sandberg et al., 2000, "Regional and strain-specific gene expression mapping in the adult mouse brain," PNAS 97: 11038-11043.

Schadt et al., 2003, "Genetics of gene expression surveyed in maize, mouse and man," Nature 422:297-302.

Schadt et al., 2003, "A new paradigm for drug discovery: integrating clinical genetic, genomic and molecular phenotype data to identify drug targets," Biochemical Society 31:437-443.

Schena et al., 1996, "Parallel human genome analysis; microarray-based expression of 1000 genes," Proc. Natl. Acad. Sci. USA 93:10614-10619.

Schena et al., 1995, "Quantitative Monitoring of Gene Expression Patterns with a Complementary DNA Microarray," Science 270: 467-470.

Shalon et al., 1996, "A DNA microarray system for analyzing complex DNA samples using two-color fluorescent probe hybridization," Genome Research 6:639-645.

Shevchenko et al., 1996, "Linking genome and proteome by mass spectrometry: Large-scale identification of yeast proteins from two dimensional gels," Proc. Natl. Acad. Sci. 93: 14440-14445.

Spielman et al., 1989, "Genetic Analysis of IDDM: Summary of GAW5 IDDM Results," Genetic Analysis of complex Traits, Part I: 43-58.

Steinmetz et al., 2002, "Dissecting the architecture of a quantitative trait locus in yeast," Nature 416: 326-330.

St. George-Hyslop et al., 1990, "Genetic linkage studies suggest that Alzheimer's disease is not a single homogeneous disorder. FAD Collaborative Study Group," Nature 347:194-197.

Struss et al., 1998, "The use of microsatellite markers for detection of genetic diversity in barley populations," Theor. Appl. Genet. 97:308-315.

Stover, et al., 2001, "Characterization of Gene Expression Profiles In Peripheral Blood Mononuclear Cells and Bone Marrow of Normal Human Volunteers," FASEB Journal, 534.9: A696.

Stunkard et al., 1990, "The Body-Mass Index of Twins Who Have Been Reared Apart," New England Journal of Medicine 322: 1483-1487.

Tamayo et al., 1999, "Interpreting patterns of gene expression with self-organizing maps: Methods and application to hematopoietic differentiation," Proc. Natl. Acad. Sci. USA 96:2907-2912.

Terwilliger et al., 1992, "A haplotype-based 'haplotype relative risk' approach to detecting allelic associations," Hum. Hered. 42:337-346.

Twine et al., 2003, "Disease-associated Expression Profiles in Peripheral Blood Mononuclear Cells from Patients with Advanced Renal Cell Carcinoma," Cancer Research 63: 6069-6075.

Velculescu et al., 1995, "Serial Analysis of Gene Expression," Science 270: 484-487.

Venter et al., 2001, "The Sequence of the Human Genome," Science 291: 1304-1351.

Weisblum et al., 1972, "Genetic Heterogeneity of Xeroderma Pigmentosum demonstrated by Somatic Cell Hybridization," Nature New Biology 238: 80-83.

Welsh et al., 1990, "Fingerprinting genomes using PCR with arbitrary primers," Nucleic Acids Research 18: 7213-7218.

Williams et al., 1999, "Joint multipoint linkage analysis of multivariate qualitative and quantitative traits," Am. J. Hum. Genet. 6:1134-1147.

Wu et al., 1993, "Abundance, polymorphism and genetic mapping of microsatellites in rice," Mol. Gen. Genet. 241:225-235.

Younossi et al., 2002, "Perspectives in Clinical Hepatology: Nonalcoholic Fatty Liver Disease: An Agenda for Clinical Research," Hepatology: 746-752.

Zeng, 1993, "Theoretical basis for separation of multiple linked gene effects in mapping quantitative trait loci," Proc. Natl. Acad. Sci. USA 90:10972-10976.

Zeng, 1994, "Precision mapping of quantitative trait loci," Genetics 136:1457-1468.

326

| Quantitative Trait (Exp. Stat. Set) 1 | 328-1 |
| Position 1 | 330-1-1 |
| statistical score | 332-1-1 |
| Position 2 | 330-1-2 |
| statistical score | 332-1-2 |
| ⋮ | |
| Position X | 330-1-X |
| statistical score | 332-1-X |
| ⋮ | |
| Quantitative Trait (Exp. Stat. Set) M | 328-M |
| Position 1 | 330-M-1 |
| statistical score | 332-M-1 |
| Position 2 | 330-M-2 |
| statistical score | 332-M-2 |
| ⋮ | |
| Position X | 330-M-X |
| statistical score | 332-M-X |

FIG. 6

|  | Phenotype 1 | ... | Phenotype M | CC 248-1 | ... | CC 248-Z |
|---|---|---|---|---|---|---|
| Organism 246-1 | Amount 1301-1-1 | ... | Amount 1301-1-M | Level 250-1-1 | ... | Level 250-1-Z |
| Organism 246-2 | Amount 1301-2-1 | ... | Amount 1301-2-M | Level 250-2-1 | ... | Level 250-2-Z |
| ⋮ | ⋮ | ⋮ | ⋮ | ⋮ | ⋮ | ⋮ |
| Organism 246-N | Amount 1301-N-1 | ... | Amount 1301-N-M | Level 250-N-1 | ... | Level 250-N-Z |

FIG. 13

COMPUTER SYSTEMS AND METHODS FOR SUBDIVIDING A COMPLEX DISEASE INTO COMPONENT DISEASES

CROSS-REFERENCE TO RELATED APPLICATIONS

This application claims benefit, under 35 U.S.C. § 119(e), of U.S. Provisional Patent Application No. 60/382,036 filed on May 20, 2002 which is incorporated herein, by reference, in its entirety. This application also claims benefit, under 35 U.S.C. § 119(e), of U.S. Provisional Patent Application No. 60/460,304 filed Apr. 2, 2003, which is incorporated herein, by reference, in its entirety.

1. FIELD OF THE INVENTION

The field of this invention relates to computer systems and methods for identifying genes and biological pathways associated with complex traits. In particular, this invention relates to computer systems and methods for subdividing complex traits into component traits. Then, gene expression data and genetic data are used to identify gene-gene interactions, gene-phenotype interactions, and biological pathways linked to the component traits.

2. BACKGROUND OF THE INVENTION

2.1. Current Approaches to Biological Target Selection

The search for biological targets (proteins) suitable for pharmaceutical study is an important task. In a classic pharmaceutical approach, a particular protein is associated with a disease. Once a biological target is identified, compounds that alter the activity of the biological target are developed with the hope that one such compound will alter the activity of the target in such a way that the diseased state is abrogated.

One approach to identifying biological targets is to gain an understanding of the biological cascades that are up-regulated or down-regulated in the diseased state. Once such biological cascades are elucidated, individual proteins within the cascade may be selected as biological targets. For example, IL-15 is an important disease target because it is an immune system signaling molecule that appears early in the cascade of events that ultimately leads to inflammatory disease. IL-15 induces both the production of TNF-alpha, another cytokine that has been shown to play a pivotal role in inflammation, as well as the recruitment of inflammatory T cells. These T cells in turn promote the production of more IL-15, and the cycle escalates. Inflammatory diseases where IL-15 plays a role include arthritis, inflammatory bowl disease, celiac disease and psoriasis. The drawback to this approach to identifying biological targets is that, often, information on the biological cascades associated with a disease are not known or fully understood. Failure to obtain this detailed knowledge may result in serious or even lethal side effects. For example, an inhibitor developed against a poorly understood biological target may, in fact, inhibit or alter several essential biological processes.

Another target-selection approach is to first choose a particular class of genes and their products, such as a class of cell surface receptors, based on the historic suitability of that class as drug targets. Once this decision has been made, the next step is to review sequence databases as well as the literature in order to identify all possible protein candidates of the selected type. Because important new gene family members may be discovered at any time, periodic review of sequence databases and the literature is necessary even after an initial comprehensive review has been completed. From the list of possible protein candidates identified by sequence database and literature review, which may include a hundred or more candidate proteins, the most promising targets are identified and advanced. Often, this review is iterative because the available information on most candidates is incomplete and constantly being added to and revised. One drawback to this approach is that it is limited to those diseases that are affected by the particular class of genes under study.

Another target-selection approach is to focus first on a specific disease, or at least diseases in specific therapeutic categories. Initial experiments focus on analyzing gene expression patterns, comparing tissues from various disease stages with normal tissue, and looking at the effects of current effective drugs, if any, on gene expression. This process yields information on hundreds of genes. The information is analyzed in order to determine a suitable target. One drawback with this approach is that, even after significant amount of investment in the analysis of the data, suitable targets may not be identified. This is particularly the case in complex diseases, such as cancer or arthritis. The problem with such diseases is that there is heterogeneity in a population that has this disease. For example, in a cancer population, individual patients may have different types of cancers. If this heterogeneity is extensive, the analysis of the information on hundreds of genes from a large population will not lead to the identification of suitable drug targets unless the heterogeneity is taken into account.

Genetics is used in some target-selection approaches. Genetics is particularly useful for identifying genes and pathways associated with traits. This knowledge, in turn, can be used to identify suitable targets for drug development. One genetic technique is linkage analysis, in which genes are linked with gross phenotypes. In one instance, cystic fibrosis has been linked to mutations in the cystic fibrosis gene using linkage analysis. The approach of applying genetics to gross phenotypes has the drawback in that it is limited to particular situations, such as cystic fibrosis, where mutations in the gene cause the disease.

In another approach to finding biological targets, genetics is applied to clinically sub-divided phenotypes. That is, risk factors associated with a particular disease are measured in a large patient population and these measurements are used to link particular quantitative trait loci within the genome of the patient population to the risk factors using genetic approaches. For example, in the case of heart disease, phenotypes such as triglyceride levels, HDL/LDL levels, and cholesterol levels are measured in a patient population. Then, one or more of these clinically sub-divided phenotypes is linked to a quantitative trait locus (QTL) in the human genome. As used herein, a quantitative trait locus (QTL) is a region of a genome that has an influence on a quantitative trait. QTL are analyzed using QTL mapping in order to identify genes that are linked to the clinically sub-divided phenotypes. QTL mapping methodologies provide statistical analysis of the association between phenotypes and genotypes for the purpose of understanding and dissecting the regions of a genome that affect complex traits.

A key development in the field of genetics has been the construction of large collections of molecular/genetic markers, which can be used to construct detailed genetic maps of species such as humans. These maps are used in quantitative trait locus (QTL) mapping methodologies such as single-marker mapping, interval mapping, composite interval mapping and multiple trait mapping. (For a review, see Doerge, 2002, *Nature Reviews: Genetics* 3: 43-62). Despite the development of improved marker maps, the goal of identifying all regions that are associated with a specific complex phenotype is typically difficult to accomplish because of the sheer number of QTL, the possible epistatis or interactions between QTL, as well as many additional sources of variation.

The use of genetics to identify genes and pathways associated with traits follows a standard paradigm. First, a genome-wide linkage study is performed using hundreds of genetic markers in family-based data to identify broad regions linked to the trait. The result of this standard sort of linkage analysis is the identification of regions controlling for the trait, thereby restricting attention from the 30,000 plus genes in, say, the human genome, to perhaps as few as 500 to 1000 genes in a particular region of the genome that is linked to the trait. However, the regions identified using linkage analysis are still far too broad to identify candidate genes associated with the trait. Therefore, such linkage studies are typically followed up by fine mapping the regions of linkage using higher density markers in the linkage region, increasing the number of families in the analysis, and identifying alternative populations for study. These efforts further restrict attention to narrower regions of the genome, on the order of 100 genes in a particular region linked to the trait. Even with the more narrowly defined linkage region, the number of genes to validate is still unreasonably large. Therefore, research at this stage focuses on identifying candidate genes based on putative function of known genes in the region and the potential relevance of that function to the trait. This approach is problematic because it is limited to what is currently known about genes. Often, such knowledge is limited and subject to interpretation. As a result, researchers are often led astray and do not identify the genes affecting the trait.

There are many reasons that standard genetic approaches have not proven very successful in the identification of genes associated with complex traits, such as human diseases. First, common human diseases such as heart disease, obesity, cancer, osteoporosis, schizophrenia, and many others are complex in that they are polygenic. That is, they potentially involve many genes across several different biological pathways and they involve complex gene-environment interactions that obscure the genetic signature. Second, the complexity of the diseases leads to a heterogeneity in the different biological pathways that can give rise to the disease. Thus, in any given heterogeneous population, there may be defects across several different pathways that can give rise to the disease. This reduces the ability to identify the genetic signal for any given pathway. Because many populations involved in genetic studies are heterogeneous with respect to the disease, multiple defects across multiple pathways are operating within the population to give rise to the disease. Third, even when statistically significant associations between the complex traits and molecular markers are identified, the genomic regions are usually so large that subsequent experiments, used to zero in on these regions, are often expensive. The limitations of this technology typically result in the loss of at least one of the regions that affect or are linked to a complex trait. In the event of success, which is the identification of the genomic region that contains genes that are responsible for the complex trait variation, the expense and time from the beginning to the end of this process is often too great for widespread application to problems of scientific, economic, or medical importance. Fourth, the traits and disease states themselves are often not well defined. Fifth, in the case where the diseased state is heterogeneous in the patient population, the ability to determine which QTL are linked to the clinically sub-divided phenotypes is lost due to the heterogeneity. Therefore, subphenotypes are often overlooked even though these subphenotypes implicate different sets of biological pathways. This reduces the power of detecting the associations.

2.2. Complex Traits

As Section 2.1 indicates, known approaches to finding suitable biological targets to alleviate complex traits are problematic. The term "complex trait" refers to any phenotype that does not exhibit classic Mendelian recessive or dominant inheritance attributable to a single gene locus. See, for example, Lander and Schork, 1994, *Science* 265: 2037. Such "complex" traits include susceptibilities to heart disease, hypertension, diabetes, cancer, and infection. Complex traits arise when the simple correspondence between genotype and phenotype breaks down, either because the same genotype can result in different phenotypes (due to the effect of chance, environment, or interaction with other genes) or different genotypes can result in the same phenotype.

It is often difficult to find a genetic marker that shows perfect cosegregation with a complex trait. The reasons for this can be ascribed to fundamental problems associated with complex traits. These fundamental problems include incomplete penetrance and phenocopy. Some individuals who inherit a predisposing allele may not manifest the disease (incomplete penetrance), whereas others who inherit no predisposing allele may nonetheless get the disease as a result of environmental or random causes (phenocopy). Thus, the genotype at a given locus may affect the probability of disease, but not fully determine the outcome. The penetrance function $f(G)$, specifying the probability of disease for each genotype G, may also depend on nongenetic factors such as age, sex, environment, and other genes. For example, the risk of breast cancer by ages 40, 55, and 80 is 37%, 66%, and 85% in a woman carrying a mutation at the BCRA1 locus as compared with 0.4%, 3%, and 8% in a noncarrier (Easton et al., 1993, *Cancer Surv.* 18: 1995; Ford et al., 1994, *Lancet* 343: 692). In such cases, genetic mapping is hampered by the fact that a predisposing allele may be present in some unaffected individuals or absent in some affected individuals.

Another problem with complex traits is that mutations in any one of several genes may result in identical phenotypes (genetic heterogeneity). Thus, in cases where there is genetic heterogeneity, it may be difficult to determine whether two patients suffer from the same disease for different genetic reasons until the genes are mapped. Examples of complex diseases that arise due to genetic heterogeneity in humans include polycystic kidney disease (Reeders et al., 1987, *Human Genetics* 76: 348), early-onset Alzheimer's disease (George-Hyslop et al., 1990, *Nature* 347: 194), maturity-onset diabetes of the young (Barbosa et al., 1976, *Diabete Metab.* 2: 160), hereditary nonpolyposis colon cancer (Fishel et al., 1993, *Cell* 75: 1027) ataxia telangiectasia (Jaspers and Bootsma, 1982, *Proc. Natl. Acad. Sci. U.S.A.* 79: 2641), obesity, and xeroderma pigmentosum (De Weerd-Kastelein, *Nat. New Biol.* 238: 80). Genetic heterogeneity hampers genetic mapping, because a chromosomal region may cosegregate with a disease in some families but not in others.

Yet another problem associated with some complex traits is the phenomenon of polygenic inheritance. Polygenic inheritance arises when a complex trait requires the simultaneous presence of mutations in multiple genes. An example of polygenic inheritance in humans is one form of retinitis pigmentosa, which requires the presence of heterozygous mutations at the perpherin/RDS and ROM1 genes (Kajiwara et al., 1994, *Science* 264: 1604). It is believed that the proteins coded by RDS and ROM1 are thought to interact in the photoreceptor outer pigment disc membranes. Polygenic inheritance complicates genetic mapping, because no single locus is strictly required to produce a discrete trait or a high value of a quantitative trait.

High frequency of disease-causing alleles will cause difficulties in mapping even a simple trait if the disease-causing allele occurs at high frequency in the population. That is because the expected Mendelian inheritance pattern of disease will be confounded by the problem that multiple independent copies of D may be segregating in the pedigree and that some individuals may be homozygous for D, in which case one will not observe linkage between D and a specific allele at a nearby genetic marker, because either of the two homologous chromosomes could be passed to an affected offspring. Late-onset Alzheimer's disease provides one example of the problems raised by high frequency disease-causing alleles. Initial linkage studies found weak evidence of linkage to chromosome 19q, but they were dismissed by many observers because the lod score (logarithm of the likelihood ratio for linkage) remained relatively low, and it was difficult to pinpoint the linkage with any precision (Pericak-Vance et al., 1991, *Am J Hum. Genet.* 48: 1034). The confusion was finally resolved with the discovery that the apolipoprotein E type 4 allele appears to be the major causative factor on chromosome 19. The high frequency of the allele (about 16% in most populations) had interfered with the traditional linkage analysis (Corder et al., 1993, *Science* 261: 921). High frequency of disease-causing alleles becomes an even greater problem if genetic heterogeneity is present.

Thus, given the above background, what is needed in the art are improved methods for identifying genes and biological pathways that affect complex traits, such as complex diseases. Improved methods for identifying such genes and biological pathways will lead to improved biological target-selection.

Discussion or citation of a reference herein will not be construed as an admission that such reference is prior art to the present invention.

3. SUMMARY OF THE INVENTION

The present invention provides novel computer systems and methods for identifying genes and biological pathways that affect complex traits. Patient populations are subdivided based on cellular constituent measurements, such as gene or protein expression measurements. Subdivided patient populations are then subjected to genetic methods that are designed to identify targets in each sub-group. The approach taken in the present invention is advantageous because it helps to circumvent the problems raised by complex traits, including incomplete penetrance, phenocopy, genetic heterogeneity, polygenic inheritance, and high frequency of disease-causing alleles. The filtration of a disease population prior to subjecting the population to quantitative genetic analysis presents an additional advantage. The filtration of the patient population reduces the heterogeneity present in the disease population that is subjected to quantitative genetic analysis. This, in turn, improves the accuracy and reliability of results obtained through quantitative genetic analysis. These improvements lead to an increase in the ability of identifying genes in biological pathways associated with complex traits that can serve as drug discovery targets.

One embodiment of the present invention provides a method for identifying a quantitative trait locus for a complex trait that is exhibited by a plurality of organisms in a population. The plurality of organisms comprise a single species. In the method, the population is divided into a plurality of sub-populations using a classification scheme that classifies each organism in the population into a sub-population in the plurality of sub-populations. The classification scheme uses a plurality of cellular constituent measurements from each of the organisms. Further, for each sub-population in the plurality of sub-populations, quantitative genetic analysis is performed on the sub-population in order to identify the quantitative trait loci for the complex trait. In some embodiments, the cellular constituent measurements from each of the organisms are transcriptional state measurements or translational state measurements. In other embodiments, the cellular constituents comprise a plurality of metabolites and the plurality of cellular constituent measurements are derived by a cellular phenotypic technique such as a metabolomic technique in which a plurality of metabolite levels in each organism is measured. In some embodiments, the plurality of cellular constituent measurements comprise gene expression levels, abundance of mRNA, protein expression levels, or metabolite levels.

In some embodiments of the present invention, the complex trait is characterized by an allele that exhibits incomplete penetrance in the population. In some embodiments, the complex trait is a disease that is contracted by an organism in the population, and the organism inherits no predisposing allele to the disease. In some embodiments, the complex trait arises when any of a plurality of different genes in the genome of the single species represented by the population is mutated. In some embodiments, the complex trait requires the simultaneous presence of mutations in a plurality of genes in the genome of the single species represented by the population. In some embodiments, the complex trait is associated with a high frequency of disease-causing alleles in the population. Finally, in some embodiments, the complex trait is a phenotype that does not exhibit Mendelian recessive or dominant inheritance attributable to a single gene locus.

In yet other embodiments of the present invention, the step of dividing the population further comprises determining whether a class predictor is available. When a class predictor is available, a supervised classification scheme is used to classify each organism in the population into a sub-population in the plurality of sub-populations. When a class predictor is not available, an unsupervised classification scheme is used to classify each organism in the population into a sub-population in the plurality of sub-populations.

In some embodiments of the present invention, the classification scheme is a supervised classification scheme whereas in other embodiments the classification scheme is an unsupervised classification scheme. Supervised classification schemes in accordance with the present invent use techniques that include, but are not limited to, linear discriminant analysis and linear regression. Linear regression is a broad category of statistics that includes, but is not limited to, multiple linear regression, partial least squares regression, and principal components regression. Unsupervised classification schemes in accordance with the present invention include, but are not limited to, hierarchical cluster analysis, non-hierarchical cluster analysis, artificial neural networks, and self-organizing maps.

In some embodiments of the present invention, the hierarchical cluster analysis uses a nearest-neighbor algorithm, a farthest-neighbor algorithm, an average linkage algorithm, a centroid algorithm, or a sum-of-squares algorithm to determine the similarity between (i) the plurality of cellular constituent measurements from one organism in the population and (ii) the plurality of cellular constituent measurements from another organism in the population. In some embodiments, the hierarchical cluster analysis is agglomerative clustering, polythetic divisive clustering or monthetic divisive clustering. In some embodiments of the present invention, the agglomerative clustering procedure uses Pearson correlation coefficients; Euclidean distance, squared Euclidean distance, Euclidean sum of squares, a Manhattan metric, or squared Pearson correlation coefficients to determine similarity between (i) the plurality of cellular constituent measurements from one organism in the population and (ii) the plurality of cellular constituent measurements from another organism in the population. In still other embodiments of the present invention, the non-hierarchical cluster analysis is K-means clustering, fuzzy k-means clustering, or Jarvis-Patrick clustering. In some embodiments of the present invention, the artificial neural network is a Kohonen artificial neural network or an auto-associative neural network.

In some embodiments of the present invention, the quantitative genetic analysis is performed using linkage analysis, a form of quantitative trait locus (QTL) analysis that uses the plurality of cellular constituent measurements as a phenotypic trait, or association analysis. In some embodiments in which the QTL analysis uses the plurality of cellular constituent measurements as a phenotypic trait, the QTL analysis has the following steps. First, QTL data from a plurality of QTL analyses is clustered to form a QTL interaction map. Each QTL analysis in the plurality of QTL analyses is performed for a gene G in a plurality of genes in the genome of the plurality of organisms using a genetic marker map and a quantitative trait in order to produce the QTL data. For each QTL analysis, the quantitative trait comprises an expression statistic for the gene G, for which the QTL analysis has been performed, for each organism in the population. Further, the genetic marker map is constructed from a set of genetic markers associated with the plurality of organisms. Second, the QTL interaction map is analyzed to identify the QTL associated with the quantitative trait.

Some embodiments of the present invention provide a computer program product for use in conjunction with a computer system. The computer program product comprises a computer readable storage medium and a computer program mechanism embedded therein. The computer program mechanism comprises a classification module and a quantitative genetic analysis module. The classification module includes instructions for dividing a plurality of organisms in a population into a plurality of sub-populations using a classification scheme. The classification scheme classifies each organism in the population into a sub-population in the plurality of sub-populations. The plurality of organisms comprises a single species and the classification scheme uses a plurality of cellular constituent measurements from each organism in the population. The quantitative genetic analysis module includes instructions for performing, for each sub-population in the plurality of sub-populations, a quantitative genetic analysis on the sub-population in order to identify a quantitative trait loci for a complex trait that is exhibited by one or more organisms in the plurality of organisms.

Some embodiments of the present invention provide a computer system for identifying a quantitative trait loci for a complex trait that is exhibited by a plurality of organisms in a population. The computer system comprises a central processing unit and a memory coupled to the central processing unit. The memory stores a classification module and a quantitative genetic analysis module. The classification module includes instructions for dividing a plurality of organisms in a population into a plurality of sub-populations using a classification scheme. The classification scheme classifies each organism in the population into a sub-population in the plurality of sub-populations. The plurality of organisms comprises a single species and the classification scheme uses a plurality of cellular constituent measurements from each organism in the population. The quantitative genetic analysis module includes instructions that, for each sub-population in the plurality of sub-populations, performs quantitative genetic analysis on the sub-population in order to identify a QTL for a complex trait that is exhibited by one or more organisms in the population.

Another aspect of the present invention provides a method of subdividing a plurality of organisms S in order to derive a plurality of subpopulations for use in quantitative genetic analysis. The plurality of organisms S comprises a single species. Furthermore, a complex trait is exhibited by one or more organisms in the plurality of organisms S. Two or more groups of organisms are identified within the plurality of organisms S that respectively represent an independent extreme with respect to the complex trait. The set of cellular constituents G associated with the single species is determined. The set of cellular constituents G is able to discriminate between the two or more groups of organisms within the plurality of organisms S. For each cellular constituent i in the set of cellular constituents G, QTL analysis is performed with the cellular constituent i using, as the quantitative trait, an amount of the cellular constituent i respectively measured from each organism in at least a portion of the plurality of organisms S. This results in the identification of one or more cellular constituents that have a QTL that interacts with or overlaps with a first QTL that is linked to the complex trait. The plurality of organisms S is clustered based on measured amounts of each identified cellular constituent. The measured amounts of each cellular constituent are respectively measured from each organism in at least a portion of the plurality of organisms S, thereby deriving the plurality of subpopulations. In some embodiments, the method further comprises performing a series of QTL analyses on a subpopulation in the plurality of subpopulations in order to identify a QTL for the complex trait. Each QTL analysis in the series of QTL analyses uses measured amounts of a cellular constituent in the set of cellular constituents G as a quantitative trait. Furthermore, the measured amounts of the cellular constituent are respectively measured from each organism in at least a portion of the plurality of organisms S.

4. BRIEF DESCRIPTION OF THE DRAWINGS

FIG. 6 illustrates a quantitative trait locus results database in accordance with one embodiment of the present invention.

FIG. 13 illustrates a data structure that comprises that data used to identify cellular constituents that discriminate a trait under study.

Like reference numerals refer to corresponding parts throughout the several views of the drawings.

5. DETAILED DESCRIPTION

The present invention provides computer systems, computer program products, and methods for associating a gene with a trait exhibited by one or more organisms in a plurality of organisms of a single species. Exemplary organisms include, but are not limited to, plants and animals. In specific embodiments, exemplary organisms include, but are not limited to, plants such as corn, beans, rice, tobacco, potatoes, tomatoes, cucumbers, fruit trees, cabbage, lettuce, and wheat. In specific embodiments, exemplary organisms include, but are not limited to animals such as mammals, primates, humans, mice, rats, dogs, cats, chickens, horses, cows, pigs, and monkeys. In yet other specific embodiments, organisms include, but are not limited to, *Drosophila*, yeast, viruses, and *C. elegans*. In some instances, the gene is associated with the trait by identifying a biological pathway in which the gene product participates. In some embodiments of the present invention, the trait of interest is a complex trait such as a human disease. Exemplary human diseases and traits of interest are described in Section 5.14, infra.

The present invention uses quantitative traits to help identify regions of a genome that influence a complex trait. In one embodiment, a quantitative trait is the expression level of a cellular constituent. Cellular constituents include, but are not limited to, gene expression levels, abundance of mRNA, protein expression levels, and metabolite levels in a biological system. More complex examples of quantitative traits are provided below. A quantitative trait may be a continuous trait (e.g., lipid level) or a discontinuous trait (e.g., presence of a disease state). The present invention makes uses of QTL analysis. Examples of QTL analysis include but are not limited to linkage analysis as described in Section 5.2, QTL analysis using cellular constituent levels as described in Section 5.3, and association analysis, as described in Section 5.4.

5.1. Overview of the Invention

Figure 1:
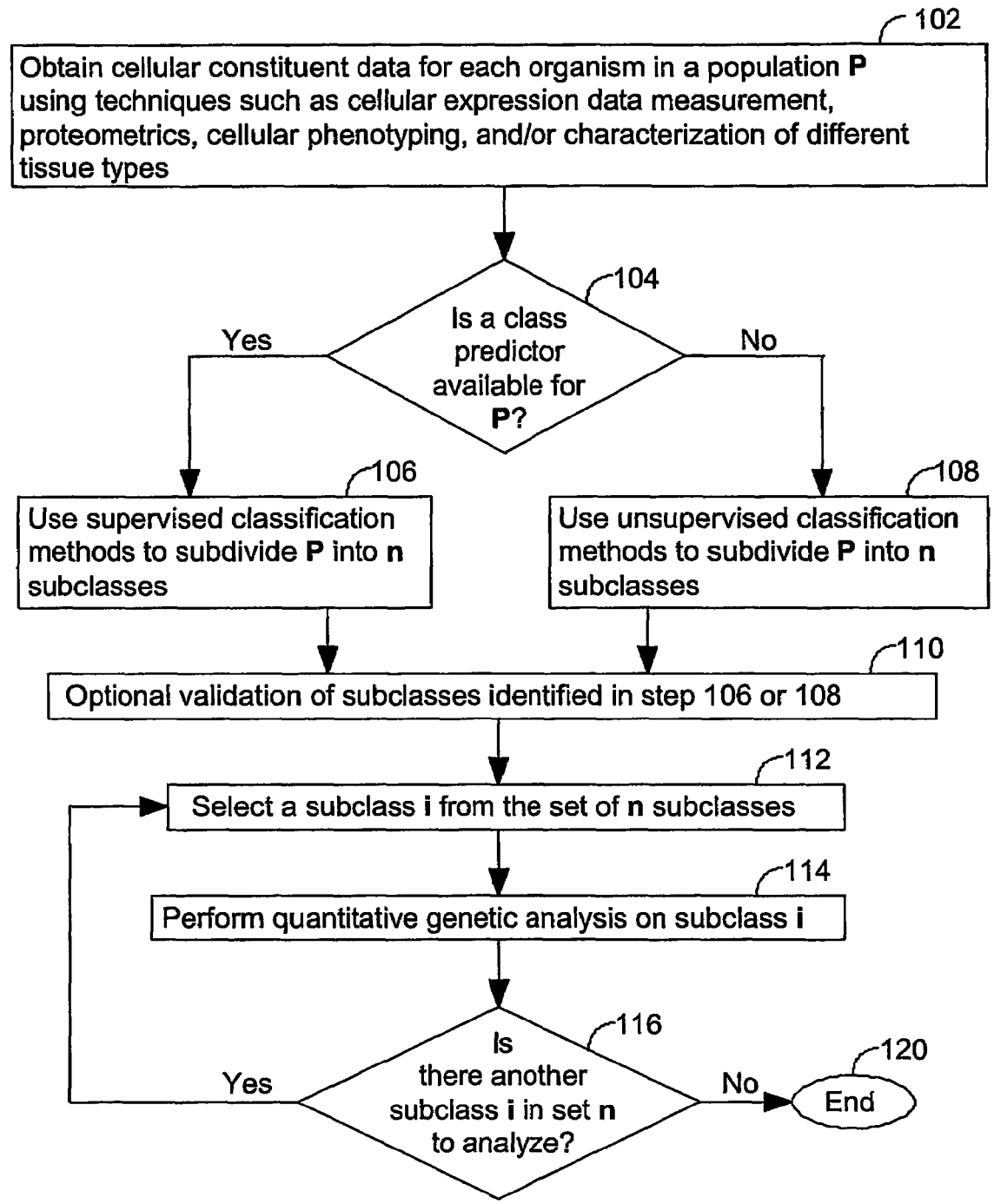
FIG. 1 illustrates processing steps for subdividing a population P into n subgroups and then subjecting one or more of the n subgroups to quantitative genetic analysis in accordance with an embodiment of the present invention.
Figure 2:
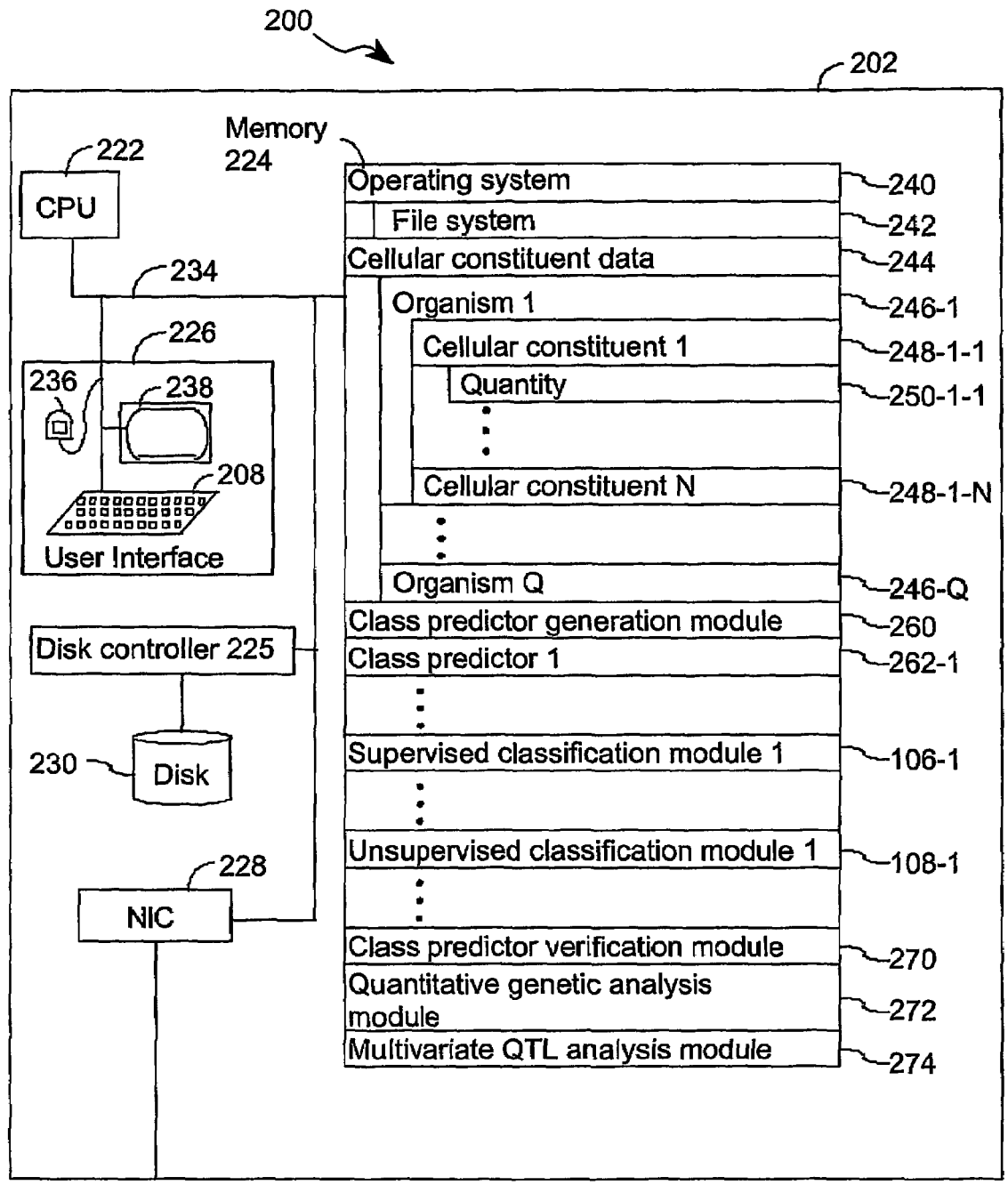
FIG. 2 illustrates a computer system for subdividing a population P into n subgroups and then subjecting one or more of the n subgroups to quantitative genetic analysis in accordance with a preferred embodiment of the present invention.

The general steps taken in accordance with one aspect of the present invention may be understood by using FIGS. 1 and 2 as a reference. FIG. 1 illustrates the processing steps that are performed in accordance with one embodiment of the present invention. In addition, FIG. 2 illustrates a system 200 that is operated in accordance with one embodiment of the present invention. System 200 comprises at least one computer 202 (FIG. 2). Computer 202 comprises standard components including a central processing unit 222, memory 224 for storing program modules and data structures, user input/output device 226, a network interface 228 for coupling server 202 to other computers via a communication network (not shown), a disk controller 225 for controlling non-volatile storage 230, and one or more busses 234 that interconnect these components. User input/output device 226 comprises one or more user input/output components such as a mouse 236, display 238, and keyboard 208.

Memory 224 comprises a number of modules and data structures that are used in accordance with the present invention. It will be appreciated that, at any one time during operation of the system, a portion of the modules and/or data structures stored in memory 224 is stored in random access memory 224 while another portion of the modules and/or data structures is stored in non-volatile storage 230. In a typical embodiment, memory 224 comprises an operating system 240. Operating system 240 comprises procedures for handling various basic system services and for performing hardware dependent tasks. Memory 224 further comprises a file system 242 for file management. In some embodiments, file system 242 is a component of operating system 240.

In the embodiment illustrated in FIGS. 1 and 2, a population P exhibiting a complex trait, such as a complex disease, is subdivided. Then, each subdivided population is subjected to genetic analysis in order to identify genes that are useful drug discovery targets. The process begins with the step of obtaining cellular constituent measurements, such as gene or protein expression measurements, from each organism in population P (FIG. 1, step 102). Population P is defined herein as any population of a single species that exhibits a complex trait, such as a complex disease. In some embodiments, the population comprises five, twenty-five, fifty, one hundred, five hundred, one thousand or more organisms. The cellular constituent measurements can be derived from transcriptional state measurements (see Section 5.11), translational data measurements, (see Section 5.12), or other measurements, such as cellular phenotypic techniques or the characterization of differences in cellular constituent levels between different tissue types (see Section 5.13). Cellular phenotypic techniques include metabolomic techniques in which a plurality of metabolites are measured. Cellular constituents include, but are not limited to, gene expression levels, abundance of mRNA, protein expression levels, and metabolite levels in a biological system. Levels of various constituents of a cell, such as mRNA encoding genes and/or protein expression levels, are known to change in response to drug treatments and other perturbations of the cell's biological state. Measurements of a plurality of such "cellular constituents" therefore contain a wealth of information about the affect of perturbations on the cell's biological state. The collection of such measurements is generally referred to as the "profile" of the cell's biological state. In alternative and non-limiting embodiments, the profile of the cell's biological state may be formed of mixed aspects of the biological state of a cell. Response data can be constructed from, e.g., changes in certain mRNA abundances, changes in certain protein abundances, and changes in certain protein activities.

In some embodiments of the present invention, the levels of five or more cellular constituents in each organism in population P are measured in step 102. In other embodiments of the present invention the levels of ten, twenty, thirty, forty, fifty, one hundred, two hundred, or more cellular constituents in each organism in population P are measured in step 102. In some embodiments of the present invention the cellular constituent levels of 300, 400, 500, 800, 1200, 1500 or more cellular constituents in each organism in population P are measured in step 102. In some embodiments of the present invention the cellular constituent levels of one thousand, two thousand, five thousand, ten thousand or more cellular constituents are measured in each organism in population P in step 102. In some embodiments, the levels of $2 \times 10^4$, $3 \times 10^4$, $4 \times 10^4$, $5 \times 10^4$, $6 \times 10^4$ or more cellular constituents are measured from each organism in population P in processing step 102.

In one embodiment, the cellular constituent measurements obtained in processing step 102 are stored as cellular constituent data 244 in memory 224 (FIG. 2). In particular, each organism in population P receives an entry 246 in data structure 244. Each entry 246 includes a plurality of cellular constituents 248. For each cellular constituent 248 in each entry 246, there is a quantity entry 250 that stores the quantity of the corresponding cellular constituent 248 as measured in step 102 (FIG. 1).

In step 104 (FIG. 1), the determination is made as to whether a class predictor is available to divide population P into a collection of subgroups. A class predictor is defined herein as a construct that is capable of assigning a sample (e.g., a patient or specimen in population P) to a patient sub-class. In some embodiments, a class predictor is generated by class predictor generation module 260 (FIG. 2) from a collection of known samples (e.g., patients) that have already been subdivided into defined subgroups in accordance with underlying biological processes associated with the complex trait exhibited by population P. To illustrate this embodiment, consider a population P' that is a subset of population P. Population P' comprises subgroups "A" and "B" based on a distinction in the underlying biology associated with the complex trait exhibited by population P. That is, each member of P' is classified into either subgroup "A" or "B" based on the distinction in the underlying biology. In this situation, subgroups "A" and "B" are used to form a class predictor by identifying cellular constituents that are present in large quantities in one group ("A" or "B") but not the other group. For instance, genes that strongly express in subgroup "A" but not in subgroup "B" may be identified from the cellular constituent measurements taken for each member of each subgroup. Likewise, genes that express strongly in subgroup "B" but not subgroup "A" may be identified. These patterns of differential expression are used to construct a set of test cellular constituents. Cellular constituents measurements for patients (specimens) not in population P' may be compared to the set of test cellular constituents in order to classify the patient (specimen) into subgroup "A" or "B". Thus, in this way, the set of test cellular constituents derived from analysis of P' serves as a class predictor. For an illustration of this approach, see Golub et al. 1999, *Science* 286: 531. In some embodiments of the present invention, class predictors, such as those generated by class predictor generation module 260, are stored as class predictor data structures 262 (FIG. 2).

In some embodiments, a class predictor 262 is derived from a collection of informative genes that are differentially expressed in the various subdivisions of the complex trait exhibited by population P. In this context, informative genes are those genes that are strongly or weakly expressed in one of the subgroups of the complex trait of interest. For example, consider the case where population P is corn and the complex trait under study is average yield. Two subpopulations may be drawn from P. One subpopulation has an extremely high average yield while the other subpopulation has an extremely low average yield. By analyzing the gene expression data for the two subgroups, a class of genes that are differentially expressed in the two subgroups can be determined. Then, the entire population P can be clustered on this class of genes. Such clustering will group plants that express the class of genes in a similar manner into clusters (i.e. subgroups). Such subgroups, in turn, can be subjected to quantitative genetic analysis. Because of the more homogenous nature of the subgroups, quantitative genetic analysis of the subgroups may reveal more information on which genes are linked with the trait of interest than quantitative genetic analysis on the entire population P. In still other embodiments, a class predictor is derived from any form of biological data that can be used to sub-divide a population exhibiting a complex trait, such as a complex disease. In some embodiments, a class predictor is identified using techniques described in Section 5.16.

If a class predictor is available (FIG. 1, 104-Yes), then supervised classification methods 106 (FIG. 1) are used to subdivide population P, as disclosed in more detail below. If a class predictor is not available (104-No), then unsupervised classification methods 108 (FIG. 1) are used to subdivide population P, as disclosed in more detail below. It will be appreciated that, in some embodiments of the present invention, unsupervised classification methods 108 are used even in instances where a class predictor is available. Unsupervised classification methods 108 can be used, for example, to validate a class predictor 262. In some embodiments of the present invention, system 200 (FIG. 200) provides one or more supervised classification modules 106 and/or one or more unsupervised classification modules 108 in order to classify a population P into a set of n subgroups, where n is an integer such as 1, 2, 3, 4, 5, 6, 7, 8, or greater.

One supervised classification method 106 is illustrated by Golub et al., 1999, *Science* 286: 531. These workers defined an idealized expression pattern c that corresponds to a gene that is uniformly high in one subclass of a complex trait and uniformly low in other subclasses. Next, the expression patterns of a plurality of genes in a series of specimens were examined to identify genes that correlate to expression pattern c by more than would be expected by chance. Specifically, Golub et al. found, using expression data of 6817 genes in 38 acute leukemia samples, roughly 1100 genes that were more highly correlated with a particular leukemia type distinction than would be expected by chance. This correlation demonstrates that classification can be based on expression data. Golub et al. used 50 of the 1100 genes to construct a class predictor capable of distinguishing whether a given patient has acute myeloid leukemia (AML) versus acute lymphoblastic leukemia (ALL). Twenty-five of the fifty genes are more highly expressed in ALL patients whereas the other twenty-five genes are more highly express in ALL patients. Golub et al. demonstrated that the set of fifty genes serves as a reliable predictor for identifying new samples as AML or ALL. One of skill in the art will appreciate that the supervised classification method of Golub et al. is not limited to gene expression data but is, in fact, applicable to any form of cellular constituent data obtained in step 102 (FIG. 1).

Another supervised classification method 106 is linear discriminant analysis. Linear discriminant analysis is reviewed in Ripley, 1996, *Pattern Recognition and Neural Networks*, Cambridge University Press, New York, as well as Hastie et al., 1995, Penalized Discriminant Analysis, *The Annals of Statistics* 23: 73-102. In this approach, a score is given to a gene depending on how consistent its expression profile is with the profiles of genes belonging to one of two pre-specified categories. A positive score is given to a gene that is more similar to the genes in one category, whereas a negative scores is given to a gene that is more similar to genes in the other category. In determining similarity, certain measurements are more important than others. More weight is placed on more important measurements. This approach is used for data sets that have a large number of irrelevant measurements in the expression profile. In particular, the linear discriminant analysis approach may be successfully applied to a leukemia data set that includes measurements of certain ubiquitously expressed genes that are useless for typing. One of skill in the art will appreciate that the linear discriminant analysis classification method is applicable to any form of cellular constituent data obtained in step 102 (FIG. 1). Additional supervised classification methods are described in Section 5.15, supra.

When a class predictor 262 is not available to subdivide population P, an unsupervised classification method 108 is used to perform the task of subdividing P. One such unsupervised classification method 108 is cluster analysis. In general, cluster analysis can be used to explore the underlying structure of cellular constituent data in order to generate hypotheses. Because cluster analysis is an exploration of the internal structural organization of observed data, there may be no single "best" set of clusters, where each cluster represents a real or useful subdivision of a complex trait. One form of clustering uses algorithms that comprehensively compare all objects against each other to build either phylogenetic-type hierarchical trees (Eisen et al., 1997, Proc Natl Acad Sci USA 998: 14863-14868; Iyer et al., 1999, *Science* 283: 83-87) or other graphical representation of clusters, such as relevance networks using a variety of similarity or distance metrics, including Euclidean distance, correlation coefficients, or mutual information. See, for example, Jain & Dubes, 1988, *Algorithms for Clustering Data*, "Partitional Clustering", Prentice Hall, N.J., pp. 89-133. With respect to processing step 108, the objects that are clustered are one or more cellular constituent measurements from each organism in population P. Hierarchical tree clustering joins similar objects (sets of cellular constituent expression measurements from individuals in population P) together into successively larger clusters in a bottom-up manner (i.e., from the leaves to the root of the tree), by successively relaxing the threshold of joining objects or sets. Relevance networks take the opposite strategy. It starts with a completely connected graph with vertices representing each object and the edges representing a measure of association and then links are increasingly deleted to reveal 'naturally emerging' clusters at certain thresholds. Clustering techniques are further described in Section 5.8.1, infra.

Other forms of unsupervised classification methods 108 include partitional clustering algorithms, such as K-means analysis (See Section 5.8.2), nearest neighbor clustering, which minimize within-cluster scatter or maximize between-cluster scatter, and Jarvis-Patrick clustering (See Section 5.8.3). See also, Jain & Dubes, 1988, *Algorithms for Clustering Data*, "Partitional Clustering", Prentice Hall, N.J., pp. 89-133. Additional unsupervised classification methods 108 include artificial neural network learning algorithms, such as self-organizing maps. See, for example, Kohonen, 1982, *Biological Cybernetics* 43: 59-69. Self-organizing maps (SOMs) are well suited to the task of identifying a small number of classes (simple traits) in a data set. See, for example, Tamayo et al., 1999, *Proc Natl Acad Sci USA* 96: 2907. SOMs are described in further detail in Section 5.8.5, infra. In the SOM approach, the user specifies the number of clusters to be identified. The SOM finds an optimal set of "centroids" around which the data points appear to aggregate. It then partitions the data set, with each centroid defining a cluster consisting of the nearest data points. Golub et al. applied a two-cluster SOM to group 38 initial leukemia samples into two classes (A1 and A2) on the basis of the expression patterns of 6817 genes in each sample. The 38 member patient population comprised a heterogeneous population of acute myeloid leukemia (AML) and acute lymphoblastic leukemia (ALL) patients. That is, each patient in the 38 member patient population had either AML or ALL. The SOM was constructed using GENECLUSTER software (Tamayo et al., 1999, *Proc Natl Acad Sci USA* 96: 2907), with a variation filter excluding genes with less than fivefold variation across the collection of samples. SOM classes A1 and A2 were analyzed and found to correspond to the classes AML and ALL. Thus, Golub et al. demonstrated that gene expression data from patients exhibiting a complex trait (leukemia) can be clustered using a SOM in order to subdivide the patient population into subclasses that correspond to actual subclasses of leukemia (AML and ALL). Additional unsupervised classification methods include Kohonen artificial neural networks (Kohonen, 1989, *Self-Organization and Associative Memory*, Springer-Verlag, Berlin) and auto-associative neural networks (Kramer, 1992, *Comput Chem Eng* 16: 313-328).

Once supervised classification methods 106 or unsupervised classification methods 108 have been used to subdivide patient population P into a set of n classes, the validity of the n subclasses can optionally be verified in step 110 (FIG. 1) using class predictor verification module 270. Verification is of particular importance in instances where the "right" answers, corresponding to real components of a complex disease, are not known. Verification 110 may be conducted in many different ways. In one approach, putative subclasses n identified by methods 106 or 108 are used to create a class predictor 262 using methods such as those described above. If the right classifications are known, corresponding to known differences in the underlying biological processes associated with the complex trait, then the samples that are subdivided into each of the n subclasses can be used to form this class predictor 262. The class predictor can then be used, in turn, to classify new samples into the identified n subclasses. Because the true classification for each sample is known in this case, the ability of the newly generated class predictor to classify genes into n subclasses can be verified.

In the case where the true subclasses n are not known (i.e., unsupervised techniques were used to classify population P into n novel subsets), a class predictor for novel subclasses n cannot be independently assessed for accuracy on new samples. This is because the "right" way to classify the independent samples in not known. In this case, verification step 110 can be used to assess whether the new samples are assigned a high prediction strength. See, for example, Golub et al. 1999, *Science* 286: 531. High prediction strengths indicate that the structure seen in the initial data set is also seen in the independent data set. The predictive strength of a class predictor derived from the n subsets derived by methods 106 or 108 can be compared to a randomly generated class predictor. A class predictor 262 derived from the n subsets found using methods 106 or 108 (derived class predictor) is considered meaningful if the predictive strength of the derived class predictor is significantly greater than the predictive strength of a randomly generated class predictor.

Processing steps 112 through 120 provide an iterative process in which each subclass i in the set of n subclasses is subjected to quantitative genetic analysis. In some embodiments, processing steps 112 through 120 are performed by quantitative genetic analysis module 272 (FIG. 2). In processing step 112, a subclass i from the set of subclasses n is selected for quantitative genetic analysis. In step 114, the subclass i selected from the set of n subclasses in step 112 is subjected to quantitative genetic analysis. In some embodiments, quantitative genetic analysis 114 of subclass i comprises linkage analysis of phenotypic traits of specimens or patients in subclass i. Linkage analysis is described in Section 5.2, infra. In other embodiments, quantitative genetic analysis 114 of subclass i comprises a novel form of QTL analysis in which the transcription levels of a plurality of genes in each patient or specimen in subclass i is treated as a phenotypic trait. This novel form of quantitative genetic analysis is described in more detail in Section 5.3, infra. In still another embodiment of the present invention, quantitative genetic analysis of subclass i comprises association analysis, as described in Section 5.4, infra. Regardless of what form of quantitative genetic analysis is used, the goal of step 114 (FIG. 2) is to identify drug discovery targets in each subgroup n.

In processing step 116 (FIG. 1), the question is asked whether there is any remaining subclass that has not been subjected to quantitative genetic analysis. If subgroups remain (116-Yes), process control returns to processing step 112 and another subclass i is selected from the set of subclasses n. If, however, each subclass i in the set of subclasses n has been subjected to quantitative genetic analysis, the process ends 120.

In one embodiment in accordance with the present invention, the degree to which each QTL making up a group identified by the quantitative genetic analysis module belongs with other QTLs within the group is tested by fitting a multivariate statistical model to the group. As used herein, a quantitative trait locus (QTL) is a region of a genome that has an influence on a quantitative trait. Multivariate statistical models have the capability to consider multiple quantitative traits simultaneously, model epistatic interactions between the QTLs and test other variations that determine whether genes in a candidate pathway group belong to the same or related biological pathway. Specific tests can be done to determine if the traits under consideration are actually controlled by the same QTL (pleiotropic effects) or if they are independent. Exemplary multivariate statistical models that may be used in accordance with the present invention are found in Section 5.9, infra. In some embodiments of the present invention, such multivariate statistical models are performed using multivariate QTL analysis module 274 (FIG. 2).

Now that processing steps in accordance with one embodiment of the present invention have been disclosed, those of skill in the art will see a number of advantages that the techniques of the present invention provide. By performing quantitative genetic analysis on a subclass n rather than the entire population P, the problems associated with the quantitative genetic analysis of complex traits, such as incomplete penetrance, phenocopy, genetic heterogeneity, polygenic inheritance, and high frequency of disease-causing alleles, is minimized. In addition, in cases where the complex trait under study in population P is a complex disease, such as cancer, or even a type of cancer, the methods of the present invention can be used to parse the population into a series of subpopulations n, where each subpopulation has a particular form of cancer. For example, consider the case of leukemia. Although the distinction between AML and ALL has been well established, no single test is currently sufficient to establish the diagnosis between AML and ALL. Rather, clinical practice involves an experienced hematopathologist's interpretation of the tumor's morphology, histochemistry, immunotyping, and cytogenetic analysis, each performed in a separate, highly specialized laboratory. Despite this, leukemia classification remains imperfect and error prone. Using the methods of the present invention, cellular constituent measurement data can be used to classify a leukemia population into AML and ALL subpopulations. In fact, the methods of the present invention can be used to segregate a leukemia population into AML, B-lineage ALL, and T-lineage ALL by setting n in processing steps 106/108 to three. Further subdivision of leukemia may be performed in order to classify population P in a larger number of classifications that differentiate various aspects of the tumor biology. Then, subsequent quantitative genetic analysis can be used to identify genes associated with the various aspects of the underlying tumor biology.

In a more general example, the methods of the present invention can be used to subdivide a population P based on distinguishing aspects of the underlying biology associated with the complex trait. Then, advantageously, each subdivided population is individually studied using quantitative genetic analysis. By subdividing the population, the population subjected to quantitative genetic analysis is effectively filtered. The use of filtered sub-populations rather than, or in addition to, a general population P improves the ability of the subsequent quantitative genetic analysis to identify genes associated with a trait found in a subpopulation. It will further be appreciated that a given population P may be subdivided more than once in order to achieve the necessary level of homogeneity for subsequent quantitative genetic analysis.

In some embodiments, population P is a segregating population for which pedigree data is available. In such embodiments, linkage analysis can be used to create a set of informative genes that can be used to subdivide population P. Such embodiments begin with the identification of a set of genes that are able to discriminate between subgroups in population P exhibiting extreme phenotypes for a trait of interest. Then, a QTL is identified for the trait of interest using preliminary linkage analysis. The preliminary linkage analysis uses the pedigree information available for the entire population P as well as the phenotypic information available for entire population to identify one or more QTL that is linked to the quantitative trait. More details on linkage analysis is described in Section 5.2 infra. In addition to the preliminary linkage analysis, a series of QTL analyses is performed. In each QTL analysis in the series of analyses, the expression level of a gene, selected from among the set of discriminating genes, serves as a quantitative phenotype. More details on this form of QTL analysis is described in Section 5.3, infra. Those genes that produce a QTL that is linked with or overlaps with the QTL identified for the trait of interest are retained in the set of discriminating genes. Population P is clustered based on expression levels of the genes remaining in the set of discriminating genes. Any form of clustering can be used in this step, including any of the clustering methods found in Section 5.8, infra. The clustering produces a set of subgroups (clusters). Linkage analysis, as described in Section 5.2, is then performed on each subgroup using the trait of interest as the quantitative trait. By subdividing the population, some of the subgroups should have significantly enhanced genetic signature for the trait of interest. Such subgroups that have an increased signal for the trait of interest are subjected to a series of QTL analyses in accordance with Section 5.3. In each QTL analysis in this series of analyses, a gene, selected from among the set of discriminating genes, serves as the quantitative phenotype. The linkage data derived from the series of QTL analyses reveals which QTL are linked to the set discriminating genes. Multivariate analysis of the such QTL, in turn, leads to the identification of which QTL are linked with the trait of interest. This embodiment is illustrated in Section 5.17. In embodiments where pedigree information is not available, a preliminary association analysis, as described in Section 5.4 can be used in place of linkage analyses to help identify a set of genes that can be used to cluster population P into subgroups.

5.1.1 Subdividing Using Clustering

In the following method a species is studied. The species can be, for example, a plant, animal, human, or bacteria. In some embodiments, the species is human, cat, dog, mouse, rat, monkey, pigs, *Drosophila*, or corn. In some embodiments, a plurality of organisms representing the species is studied. The number of organisms in the species can be any number. In some embodiments, the plurality of organisms studied is between 5 and 100, between 50 and 200, between 100 and 500, or more than 500 organisms. In some embodiments, the plurality of organisms are an $F_2$ intercross, a $F_t$ population (formed by randomly mating $F_1$s for t-1 generations), an $F_{2:3}$ design ($F_2$ individuals are genotyped and then selfed), or a Design III ($F_2$ from two inbred lines are backcrossed to both parental lines). Thus, in some embodiments of the present invention, organisms 246 (FIG. 2) represent a population, such as an $F_2$ population, an $F_t$ population, an $F_{2:3}$ population or a Design III population.

In some embodiments, a portion of the organisms under study are subjected to a perturbation. The perturbation can be environmental or genetic. Examples of environmental perturbations include, but are not limited to, exposure of an organism to a test compound, an allergen, pain, and hot or cold temperatures. Additional examples of environmental perturbations include diet (e.g. a high fat diet or low fat diet), sleep deprivation, isolation, and quantifying natural environmental influences (e.g., smoking, diet, exercise). Examples of genetic perturbations include, but are not limited to, the use of gene knockouts, introduction of an inhibitor of a predetermined gene or gene product, N-Ethyl-N-nitrosourea (ENU) mutagenesis, siRNA knockdown of a gene, or quantifying a trait exhibited by a plurality of organisms of a species. Various siRNA knock-out techniques (also referred to as RNA interference or post-transcriptional gene silencing) are disclosed, for example, in Xia, et al:, 2002, Nature Biotechnology 20, p. 1006; Hannon, 2002, Nature 418, p. 244; Carthew, 2001, Current Opinion in Cell Biology 13, p. 244; Paddison, 2002, Genes & Development 16, p. 948; Paddison & 1-lannon, 2002, Cancer Cell 2, p. 17; Jang et al., 2002, Proceedings of the National Academy of Sciences USA 99, p. 1984; Martinez et al., 2002, Proceedings of the National Academy of Sciences USA 99, p. 14849.

Figure 15:
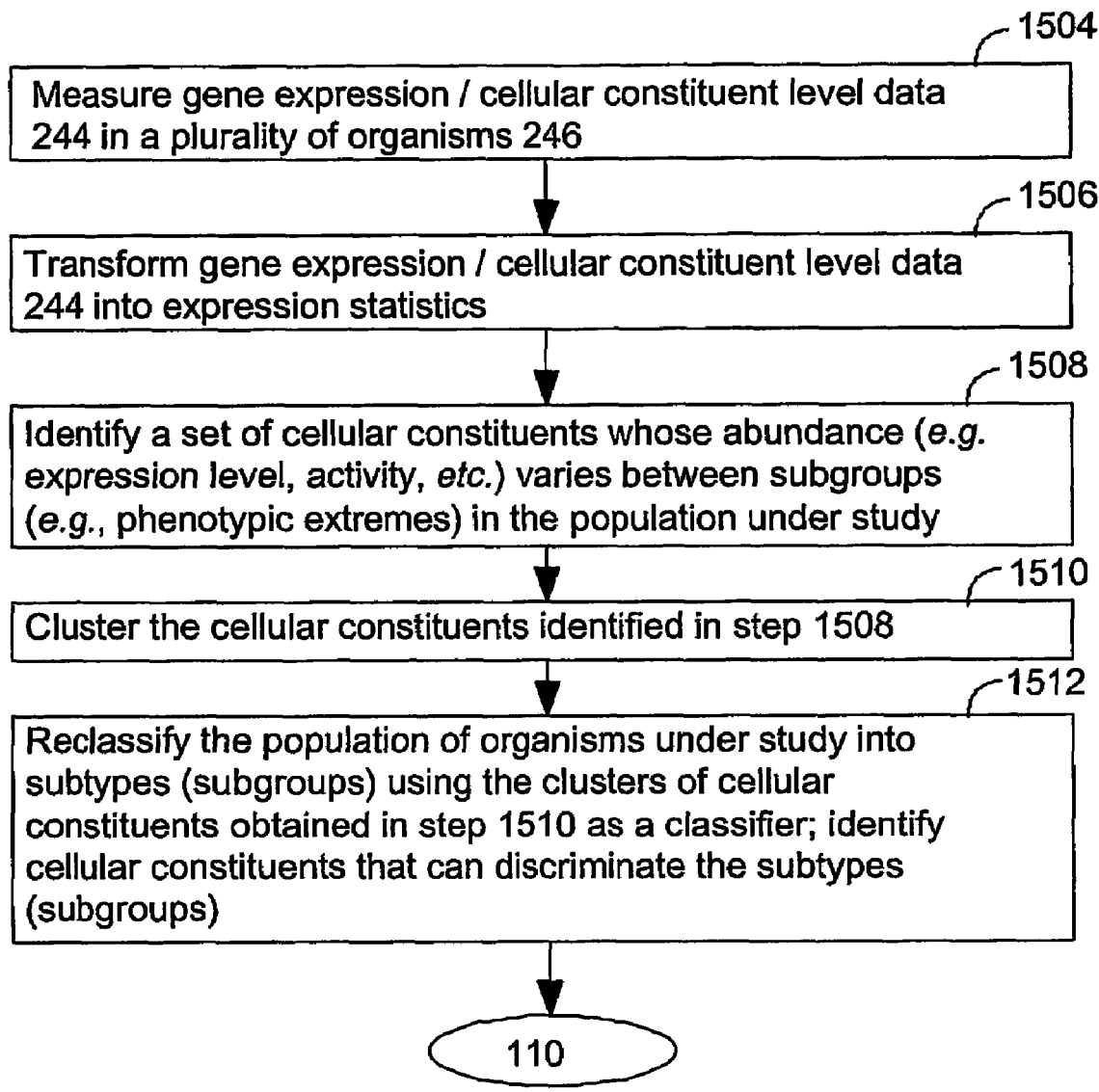
FIG. 15 illustrates processing steps for subdividing a population into subgroups in accordance with one embodiment of the present invention.

Step 204. In step 1504 (FIG. 15), the levels of cellular constituents in tissue selected from the organism are measured from the plurality of organisms 246 in order to derive gene expression/cellular constituent data 244. In some embodiments cellular constituent data from only one tissue type is collected. In other embodiments, cellular constituent data from multiple tissue types are collected.

Generally, the plurality of organisms 246 exhibit a genetic variance with respect to some trait of interest. In some embodiments, the trait is quantifiable. For example, in instances where the trait is a disease, the trait can be quantified in a binary form (e.g. "1" if the organism has contracted the disease and "0" if the organism has not contracted the disease). In some embodiments, the trait can be quantified as a spectrum of values and the plurality of organisms 46 will represent several different values in such a spectrum. In some embodiments, the plurality of organisms 246 comprise an untreated (e.g., unexposed, wild type, etc.) population and a treated population (e.g. exposed, genetically altered, etc.). In some embodiments, for example, the untreated population is not subjected to a perturbation whereas the treated population is subjected to a perturbation. In some embodiments, the tissue that is measured in step 1504 is blood, white adipose tissue, or some other tissue that is easily obtained from organisms 246.

In varying embodiments, the levels of between 5 cellular constituents and 100 cellular constituents, between 50 cellular constituents and 100 cellular constituents, between 300 and 1000 cellular constituents, between 800 and 5000 cellular constituents, between 4000 and 15,000 cellular constituents, between 10,000 and 40,000 cellular constituents, or more than 40,000 cellular constituents are measured.

In one embodiment, gene expression/cellular constituent data 244 comprises the processed microarray images for each individual (organism) 246 in a population under study. In some embodiments, such data comprises, for each individual 246, quantity (intensity) information 250 for each gene/cellular constituent 248 represented on the microarray, optional background signal information, and associated annotation information describing the gene probe. In some embodiments, cellular constituent data 244 is, in fact, protein expression levels for various proteins in a particular tissue in organisms 246 under study.

In one aspect of the present invention, cellular constituent levels are determined in step 1504 by measuring an amount of the cellular constituent in a predetermined tissue of the organism. As used herein, the term "cellular constituent" comprises individual genes, proteins, mRNA, metabolites and/or any other cellular components that can affect the trait under study. The level of a cellular constituent other than a gene can be measured in a wide variety of methods. Cellular constituent levels, for example, can be amounts or concentrations in the organisms, their activities, their states of modification (e.g., phosphorylation), or other measurements relevant to the trait under study.

In one embodiment, step 1504 comprises measuring the transcriptional state of cellular constituents 248 in one or more tissues of organisms 246. The transcriptional state includes the identities and abundances of the constituent RNA species, especially mRNAs. In this case, the cellular constituents are RNA, cRNA, cDNA, or the like. The transcriptional state of the cellular constituents can be measured by techniques of hybridization to arrays of nucleic acid or nucleic acid mimic probes, or by other gene expression technologies. Transcript arrays are discussed in Section 5.11, below.

In another embodiment, step 1504 comprises measuring the translational state of cellular constituents 248 in tissues. In this case, the cellular constituents are proteins. The translational state includes the identities and abundances of the proteins in the tissue. In one embodiment, whole genome monitoring of protein (e.g., the "proteome," Goffeau et al., 1996, Science 274, p. 546) can be carried out by constructing a microarray in which binding sites comprise immobilized, preferably monoclonal, antibodies specific to a plurality of protein species. Preferably, antibodies are present for a substantial fraction (e.g. 30%, 40%, 50%, 60%, or more) of the encoded proteins. Methods for making monoclonal antibodies are well known. See, for example, Harlow and Lane, 1998, *Antibodies: A Laboratory Manual*, Cold Spring Harbor, N.Y. In one embodiment, monoclonal antibodies are raised against synthetic peptide fragments designed based on genomic sequences. With such an antibody array, proteins from the organisms are contacted with the array and their binding is assayed with assays known in the art. In some embodiments, antibody arrays for high-throughput screening of antibody-antigen interactions are used. See, for example, Wildt et al., Nature Biotechnology 18, p. 989.

Alternatively, large scale quantitative protein expression analysis can be performed using radioactive (e.g., Gygi et al., 1999, Mol. Cell. Biol 19, p. 1720) and/or stable iostope ($^{15}N$) metabolic labeling (e.g., Oda et al. Proc. Natl. Acad. Sci. USA 96, p. 6591) followed by two-dimensional (2D) gel separation and quantitative analysis of separated proteins by scintillation counting or mass spectrometry. Two-dimensional gel electrophoresis is well-known in the art and typically involves focusing along a first dimension followed by SDS-PAGE electrophoresis along a second dimension. See, e.g., Hames et al., 1990, *Gel Electrophoresis of proteins: A Practical Approach*, IRL Press, New York; Shevchenko et al., 1996, Proc Nat'l Acad. Sci. USA 93, p. 1440; Sagliocco et al., 1996, Yeast 12, p. 1519; Lander 1996, Science 274, p. 536; and Naaby-Haansen et al., 2001, TRENDS in Pharmacological Science 22, p. 376. Electropherograms can be analyzed by numerous techniques, including mass spectrometric techniques, western blotting and immunoblot analysis using polyclonal and monoclonal antibodies, and internal and N-terminal micro-sequencing. See, for example, Gygi, et al., 1999, Nature Biotechnology 17, p. 994. In some embodiments, fluorescence two-dimensional difference gel electrophoresis (DIGE) is used. See, for example, Beaumont et al., Life Science News 7, 2001. In some embodiments, quantities of proteins in tissues of organisms 246 are determined using isotope-coded affinity tags (ICATs) followed by tandem mass spectrometry. See, for example, Gygi et al., 1999, Nature Biotech 17, p. 994. Using such techniques, it is possible to identify a substantial fraction of the proteins expressed in a predetermined tissue in organisms 246.

In other embodiments, step 1504 comprises measuring the activity or post-translational modifications of the cellular constituents in predetermined tissues of the plurality of organisms 246. See for example, Zhu and Snyder, Curr. Opin. Chem. Biol 5, p. 40; Martzen et al., 1999, Science 286, p. 1153; Zhu et al., 2000, Nature Genet. 26, p. 283; and Caveman, 2000, J. Cell. Sci. 113, p. 3543. In some embodiments, measurement of the activity of the cellular constituents is facilitated using techniques such as protein microarrays. See, for example, MacBeath and Schreiber, 2000, Science 289, p. 1760; and Zhu et al., 2001, Science 293, p. 2101. In some embodiments, post-translational modifications or other aspects of the state of cellular constituents are analyzed using mass spectrometry. See, for example, Aebersold and Goodlett, 2001, Chem Rev 101, p. 269; Petricoin III, 2002, The Lancet 359, p. 572.

In some embodiments, the proteome of tissue from organisms 246 is analyzed in step 1504. The analysis of the proteome of cells in the organisms (e.g. the quantification of all proteins and the determination of their post-translational modifications) typically involves the use of high-throughput protein analysis methods such as microarray technology. See, for example, Templin et al., 2002, TRENDS in Biotechnology 20, p. 160; Albala and Humphrey-Smith, 1999, Curr. Opin. Mol. Ther. 1, p. 680; Cahill, 2000, *Proteomics: A Trends Guide*, p. 47-51; Emili and Cagney, 2000, Nat. Biotechnol., 18, p. 393; and Mitchell, Nature Biotechnology 20, p. 225.

In still other embodiments, "mixed" aspects of the amounts cellular constituents are measured in step 1504. In one example, the amounts or concentrations of one set of cellular constituents in tissues from organisms 246 are combined with measurements of the activities of certain other cellular constituents in such tissues in step 1504.

In some embodiments, different allelic forms of a cellular constituent in a given organism are detected and measured in step 1504. For example, in a diploid organism, there are two copies of any given gene, one descending from the "father" and the other from the "mother." In some instances, it is possible that each copy of the given gene is expressed at different levels. This is of significant interest since this type of allelic differential expression could associate with the trait under study, particularly in instances where the trait under study is complex.

Step 1506. Once gene expression/cellular constituent data 244 has been obtained, the data is transformed (FIG. 15, step 1506) into expression statistics. In some embodiments, cellular constituent data 244 (FIG. 1) comprises transcriptional data, translational data, activity data, and/or metabolite abundances for a plurality of cellular constituents. In one embodiment, the plurality of cellular constituents comprises at least five cellular constituents. In another embodiment, the plurality of cellular constituents comprises at least one hundred cellular constituents, at least one thousand cellular constituents, at least twenty thousand cellular constituents, or more than thirty thousand cellular constituents.

The expression statistics commonly used as quantitative traits in the analyses in one embodiment of the present invention include, but are not limited to, the mean log ratio, log intensity, and background-corrected intensity derived from transcriptional data. In other embodiments, other types of expression statistics are used as quantitative traits.

In one embodiment, the expression level of each of a plurality of genes in each organism under study is normalized. Any normalization routine can be used to accomplish this normalization. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be run. Exemplary normalization routines in accordance with the present invention are disclosed in more detail in Section 5.6, below.

Step 1508. In step 1508, patterns of cellular constituent levels (e.g., gene expression levels, protein abundance levels, etc.) are identified that associate with a trait under study and/or the perturbation that is optionally applied to the population prior to cellular constituent measurement. There are several ways that step 1508 can be carried out, and all such ways are included within the scope of the present invention. One such method first identifies those cellular constituents 248 that discriminate the trait.

In one example, a perturbation is applied to the population prior to cellular constituent measurement in step 1504. The perturbation can be, for example, exposure of the organism to a compound. Exposure of the organism to a compound can be effected by a variety of means, including but not limited to, administration, injection, etc. In this example, the population of organisms 246 is divided into two classes. Those organisms 246 that have been exposed to the compound and those organisms 246 that have not been exposed to the compound. In the example, those cellular constituents (e.g. genes, proteins, metabolites, etc.) whose levels (e.g., transcriptional state, translational state, activity state, post-translational modification state, etc.) in the organisms 246 discriminate the treatment group (the group exposed to the organism) from the control group are identified using a statistical technique such as a paired t-test, an unpaired t-test, a Wilcoxon rank test, a signed rank test, or by computation of the correlation between the trait and gene expression values. In some instances, the perturbation optionally applied to the population comprises multiple treatments. In such instances, generalizations to the T-test and ranks tests, such as Anova or Kruskal-Wallis are used in this step.

In another embodiment, a perturbation is not applied to the population under study. In one case, the population under study is divided into those organisms 246 that exhibit the trait and those organisms that do not exhibit the trait. Those cellular constituents (e.g. genes, proteins, metabolites, etc.) whose levels (e.g., transcriptional state, translational state, activity state, post-translational modification state, etc.) in the organisms 246 discriminate the affected group from the unaffected group are identified using a statistical technique.

In still other embodiments, the population under study is divided into groups based on a function of the phenotype for the trait under study. Those cellular constituents whose levels in the organisms 246 discriminate between the various groups are identified using a statistical technique. For more details on the statistical techniques that can be used in step 1508, see Section 5.19, below.

In another example, the population under study exhibits a broad spectrum of phenotypes for the trait. Those cellular constituents whose levels in the organism 246 that can differentiate at least some of these phenotypes are then identified using statistical techniques. Generally speaking, in this step, the population is divided into phenotypically distinct groups and cellular constituents that distinguish between these phenotypically distinct groups are identified using statistical tests such as a t-tests (for two groups) or ANOVA (for greater than two groups).

In various embodiments, the set of cellular constituents 248 identified in step 1508 comprises between 5 and 100 cellular constituents, between 50 and 500 cellular constituents, between 400 and 1000 cellular constituents, between 800 and 4000 cellular constituents, between 3000 and 8000 cellular constituents, 8000 to 15000 cellular constituents, more 15000 cellular constituents, or less than 30000 cellular constituents.

In some embodiments, the phenotypic extremes within the population are identified. For example, in one case, the trait of interest is obesity. In such an example, very obese and very skinny organisms 246 are selected as the phenotypic extremes in this step. In one embodiment of the present invention, a phenotypic extreme is defined as the top or lowest $40^{th}$, $30^{th}$, $20^{th}$, or $10^{th}$ percentile of the population with respect to a given phenotype exhibited by the population. In some embodiments, cellular constituent levels 250 (measured in phenotypically extreme organisms) for a given cellular constituent 246 are subjected to a t-test or some other test such as a multivariate test to determine whether the given cellular constituent 246 can discriminate between phenotypic groups identified (e.g., treated versus untreated) for the population under study. A cellular constituent 246 will discriminate between phenotypic groups when the cellular constituent is found at characteristically different levels in each of the phenotypic groups. For example, in the case where there are two phenotypic groups, a cellular constituent will discriminate between the two groups when levels 250 of the cellular constituent (measured in phenotypically extreme organisms) are found at a first level in the first phenotypic group and are found at a second level in the second phenotypic group, where the first and second level are distinctly different.

Step 1510. Once the set of cellular constituents 248 that discriminate the trait or, optionally, the perturbation, have been identified (e.g., using organisms in the population that represent phenotypic extremes), they can be clustered. In one embodiment of the present invention, each cellular constituent 248 in the set of cellular constituents that discriminates the trait (or the perturbation applied to the population prior to measurement in step 1504) between two or more classes (e.g., afflicted versus nonafflicted, perturbed versus nonperturbed) is treated as a cellular constituent vector. For example, the $n^{th}$ cellular constituent 248 in the set of cellular constituents that discriminates the perturbation (e.g., complex trait) between two or more classes is represented as:

$$C_n = (A_1^n, A_2^n, \ldots, A_m^n)$$

where each A is the level (e.g., transcriptional state, translational state, activity, etc.) of cellular constituent n in a tissue of an organism 246 in the plurality of organisms under study, and m is the number of organisms considered. Cellular constituent vectors $C_n$ can be clustered based on similarities in the values of corresponding levels A in each cellular constituent vector. Cellular constituent vector $C_n$ will cluster into the same group (cellular constituent vector cluster) if the corresponding levels in such cellular constituent vectors are correlated. To illustrate, consider hypothetical cellular constituent vectors $C_n$ that are obtained by measuring three different cellular constituents in five different organisms 246. Each cellular constituent vector will therefore have five values. Each of the five values will be a level (e.g., activity, transcriptional state, translational state, etc.) of the corresponding cellular constituent n in a tissue of one of the five organisms 246:

| Exemplary cellular constituent vector $C_1$: | {0, 5, 5.5, 0, 0} |
|---|---|
| Exemplary cellular constituent vector $C_2$: | {0, 4.9, 5.4, 0, 0} |
| Exemplary cellular constituent vector $C_3$: | {6, 0, 3, 3, 5} |

Thus, for vector $C_1$, there is a level of cellular constituent "$C_1$" of 0 arbitrary units in the first organism, 5 arbitrary units in the second organism, 5.5 arbitrary units in the third organism, and 0 arbitrary units in the fourth and fifth organisms. Clustering of exemplary cellular constituent vectors $C_1$, $C_2$, and $C_3$ will result in two clusters (cellular constituent vector clusters). The first cluster will include cellular constituent vectors $C_1$ and $C_2$ because there is a correlation in the levels within each vector (0 versus 0 in organism 246-1, 5 versus 4.9 in organism 246-2, 5.5 versus 5.4 in organism 246-3, 0 versus 0 in organism 246-4, and 0 versus 0 in organism 246-5). The second cluster will include exemplary cellular constituent vector $C_3$ because the pattern of levels in vector $C_3$ is not similar to the pattern of levels in $C_1$ and $C_2$. This illustration serves to describe certain aspects of clustering using hypothetical cellular constituent level data. However, in the present invention, the cellular constituents used in this step are selected because they discriminate trait extremes. Thus, unlike the hypothetical data shown above, the cellular constituent levels should reflect that they were selected over phenotypic extremes. When this is the case, the clustering in this step will help to identify subgroups of cellular constituents within the group of cellular constituents that discriminate trait extremes. An example of this form of two-dimensional clustering is provided in Section 5.20.2, below.

In one embodiment of the present invention, agglomerative hierarchical clustering is applied to the cellular constituent vectors in step 1510. In such clustering, similarity is determined using Pearson correlation coefficients between the cellular constituent vector pairs. In other embodiments, the clustering of the cellular constituent vectors comprises application of a hierarchical clustering technique, application of a k-means technique, application of a fuzzy k-means technique, application of a Jarvis-Patrick clustering technique, application of a self-organizing map or application of a neural network. In some embodiments, the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In still other embodiments, the hierarchical clustering technique is a divisive clustering procedure. Illustrative clustering techniques that can be used to cluster gene analysis vectors are described in Section 5.8, below. In preferred embodiments, nonparametric clustering algorithms are applied to the cellular constituent vectors. In some embodiments, Spearman R, Kendall Tau, or Gamma coefficients are used to cluster the cellular constituent vectors.

Step 1512. In step 1512, the population is reclassified into subtypes using the clustering information from step 1510. The goal of step 1512 is to construct a classifier that comprises those cellular constituents that can distinguish between these subtypes. In one embodiment, a respective phenotypic vector is constructed for each organism in the population. Each phenotypic vector comprises the cellular constituent levels for all or a portion of the set of cellular constituents that were used in step 1510. In some embodiments, the order of the elements in the phenotypic vectors is determined by the clustering patterns achieved in step 1510.

The phenotypic vectors are clustered using any of the techniques described in Section 5.8. In embodiments where the order of the elements in each phenotypic vector is determined based on the clustering in step 1510, the clustering in step 1512 produces a two-dimensional cluster. In one dimension, cellular constituents are clustered based on similarities in their abundance across the population of organisms. For example, two cellular constituents would cluster together if they are expressed at similar levels throughout the population. On the other dimension, organisms are clustered based on similarity across the set of cellular constituents. For example, two organisms will cluster together if corresponding cellular constituents in each organism express at comparable levels.

The present invention provides many alternative pattern classification techniques that can be used instead of the clustering techniques that are described in steps 1510 and 1512. These alternative pattern classification techniques can be used to build classifiers from discriminating cellular constituents. Such classifiers can then be used to differentiate the general population into distinct subgroups. Such alternative techniques are described in Section 5.18.

In essence, the clustering in steps 1510 and 1512 order the population into new subgroups (e.g., phenotypic clusters). Each subgroup (phenotypic cluster) is characterized by a distinctive cellular constituent expression (or level) pattern. To illustrate, consider the case in which the clustering performed in step 1510 produces three groups of cellular constituents, namely groups A, B and C. Next, in step 1512, a phenotypic vector is constructed for each organism in the population under study. The elements in the phenotypic vectors are the measured cellular constituent levels for the respective organisms arranged in the order specified by the cellular constituent clustering results of step 1510. For illustration, suppose there are ten cellular constituents, (1, 2, 3, 4, 5, 6, 7, 8, 9, and 10), where constituents 8-10 fall into group A, constituents 4-7 fall into group B, and constituents 1-3 fall into group C. In this instance, a phenotypic vector $V_M$ for an organism M in the population could have the form:

$V_M = \{8, 9, 10, 4, 5, 6, 7, 1, 2, 3\}$ where each respective cellular constituent in the vector is represented by the level of the cellular constituent in the organism represented by the vector. Each vector $V_M$ is clustered based on these levels. Consider the hypothetical vectors for four such organisms, where cellular constituent levels are merely represented as "+" for high level and "−" for low level:

$V_1 = \{+, -, +, +, +, -, -, -, -, -\}$
$V_2 = \{-, -, -, -, -, +, +, +, +, +\}$
$V_3 = \{+, +, +, +, +, -, -, -, -, -\}$
$V_4 = \{-, -, -, -, -, +, +, +, -, +\}$

Clustering $V_1$ through $V_4$ will result in two groups (I and II):
Group I:
$V_1 = \{+, -, +, +, +, -, -, -, -, -\}$
$V_3 = \{+, +, +, +, +, -, -, -, -, -\}$
Group II:
$V_2 = \{-, -, -, -, -, +, +, +, +, +\}$
$V_4 = \{-, -, -, -, -, +, +, +, -, +\}$ It is apparent that each organism in group I has a similar cellular constituent expression (or level) pattern. Further, this similar pattern distinguishes group I from group II. Likewise, each organism in group II has a similar cellular constituent (or level) pattern and this pattern distinguishes group II from group I. In this example, the ordered set of cellular constituents from step 1510 serves as a classifier that reclassifies the organisms into subtypes.

In some embodiments the clustering of step 1510 is not performed and only phenotypic vectors are clustered in order to identify such phenotypic clusters. However, it will be appreciated from the example above that the identification of cellular constituents that can discriminate the phenotypic clusters will be more easily identifiable in cases where the clustering of step 1510 is performed because the clustering of step 1510 will tend to group discriminating cellular constituents within each phenotypic vector.

It is noted that each of the subtypes (subgroups) obtained in this step are not obtained using classical phenotypic observations. Rather, each of the subtypes are identified using an ordered set of cellular constituents levels that discriminate between phenotypically distinguishable groups. As such, each of the subtypes identified in step 1512 may well represent distinct biochemical forms of the trait under study. For example, in the case where perturbations are applied in the preceding steps, each of the subtypes identified in this step could represent a different biochemical response associated with the trait.

In step 1512, the cellular constituents that can discriminate between the newly identified subgroups (subtypes) are determined. For example, consider the example above in which the following clusters were obtained:
Group I:
$V_1 = \{+, -, +, +, +, -, -, -, -, -\}$
$V_3 = \{+, +, +, +, +, -, -, -, -, -\}$
Group II:
$V_2 = \{-, -, -, -, -, +, +, +, +, +\}$
$V_4 = \{-, -, -, -, -, +, +, +, -, +\}$ where the order of the elements in each vector is
$V_M = \{8, 9, 10, 4, 5, 6, 7, 1, 2, 3\}$ It can be seen that cellular constituents 8, 10, 4, 5, 6, 7, 1, and 3 discriminate between groups I and II whereas cellular constituents 9 and 2 do not discriminate. For example, cellular constituent 9 has the values (−/+) in group I and (−/−) in group II and cellular constituent 2 has the values (−/−) in group I and (+/−) in group II.

The set of cellular constituents that discriminate between subtypes (subgroups) identified in step 1512 serve as a classifier for the population under study. This classifier is capable of differentiating the general population into subtypes. While select organisms (e.g., phenotypically extreme organisms) were used in previous steps in order to identify and order the discriminating set of cellular constituents (the classifier), the cellular constituents identified in step 1512 are capable of classifying all the organisms in the general population into subgroups.

Step 102. Step 1512 serves to break a population down into subtypes. After step 1512, steps 110 through 120 are performed as described above and as illustrated in FIG. 1 to analyze each of these population subtypes using quantitative genetic methods.

5.2. LINKAGE ANALYSIS

This section describes a number of standard quantitative trait locus (QTL) linkage analysis algorithms that can be used in processing step 114 (FIG. 1). Such linkage analysis is also sometimes referred to as QTL analysis. See, for example, Lynch and Walsch, 1998, *Genetics and Analysis of Quantitative Traits*, Sinauer Associates, Sunderland, Mass. The primary aim of linkage analysis is to determine whether there exist pieces of the genome that are passed down through each of several families with multiple afflicted organisms in a pattern that is consistent with a particular inheritance model and that is unlikely to occur by chance alone. In other words, the purpose of these algorithms is to identify a loci (e.g., a QTL) for a phenotypic trait exhibited by one or more organisms 46. A QTL is a region of a genome of a species that is responsible for a percentage of variation in a phenotypic trait in the species under study.

The recombination fraction can be denoted by $\theta$ and is bounded between 0 and 0.5. If $\theta = 0.5$ for two loci, then alleles at the two loci are transmitted independently with half of the gametes being recombinant, for the two loci, and half parental. In this case, the loci are unlinked. If $\theta < 0.5$, then alleles are not transmitted independently, and the two loci are linked. The extreme scenario is when $\theta = 0$, so that the two loci are completely linked, and there will be no recombination between the two loci during meiosis, i.e. all gametes are parental. Linkage analysis tests whether a marker locus, of known location, is linked to a locus of unknown location, that influences the phenotype under study. In other words, a QTL is identified by comparing genotypes of organisms in a group to a phenotype exhibited by the group using pedigree data. The genotype of each organism at each marker in a plurality of markers in a genetic map produced by marker genotypic data is compared to a given phenotype of each organism. The genetic map is created by placing genetic markers in genetic (linear) map order so that the positional relationships between markers are understood. The information gained from knowing the relationships between markers that is provided by a marker map provides the setting for addressing the relationship between QTL effect and QTL location.

In some embodiments of the present invention, linkage analysis is based on any of the QTL detection methods disclosed or referenced in Lynch and Walsch, 1998, *Genetics and Analyis of Quantitative Traits*, Sinauer Associates, Inc., Sunderland, Mass.

5.2.1. Phenotypic Data Used

It will be appreciated that the present invention provides no limitation on the type of phenotypic data that can be used to perform QTL analysis. The phenotypic data can, for example, represent a series of measurements for a quantifiable phenotypic trait in a collection of organisms. Such quantifiable phenotypic traits can include, for example, tail length, life span, eye color, size and weight. Alternatively, the phenotypic data can be in a binary form that tracks the absence or presence of some phenotypic trait. As an example, a "1" can indicate that a particular species of the organism of interest possesses a given phenotypic trait and a "0" can indicate that a particular species of the organism of interest lacks the phenotypic trait. The phenotypic trait can be any form of biological data that is representative of the phenotype of each organism in the population under study. In some embodiments, the phenotypic traits are quantified and are often referred to as quantitative phenotypes.

5.2.2. Genotypic Data Used

In order to provide the necessary genotypic data for linkage analysis, the genotype of each marker in the genetic marker map is determined for each organism in a population under study. Genotypic information is derived from polymorphisms in the genome of organisms in the population. Such polymorphisms include, but are not limited to, single nucleotide polymorphisms, microsatellite markers, restriction fragment length polymorphisms, short tandem repeats, sequence length polymorphisms, and DNA methylation patterns.

Linkage analyses use the genetic map derived from marker genotypic data as the framework for location of QTL for any given quantitative trait. In some embodiments, the intervals that are defined by ordered pairs of markers are searched in increments (for example, 2 cM), and statistical methods are used to test whether a QTL is likely to be present at the location within the interval. In one embodiment, linkage analysis statistically tests for a single QTL at each increment across the ordered markers in a genetic map. The results of the tests are expressed as lod scores, which compares the evaluation of the likelihood function under a null hypothesis (no QTL) with the alternative hypothesis (QTL at the testing position) for the purpose of locating probable QTL. More details on lod scores are found in Section 5.4, as well as in Lander and Schork, 1994, Science 265, p. 2037-2048. Interval mapping searches through the ordered genetic markers in a systematic, linear (one-dimensional) fashion, testing the same null hypothesis and using the same form of likelihood at each increment.

5.2.3. Pedigree Data Used

Linkage analysis requires pedigree data for organisms in the population under study in order to statistically model the segregation of markers. The various forms of linkage analysis can be categorized by the type of population used to generate the pedigree data (inbred versus outbred).

Some forms of linkage analysis use pedigree data for populations that originate from inbred parental lines. The resulting $F_1$ lines will tend to be heterozygous at all markers and QTL. From the $F_1$ population, crosses are made. Exemplary crosses include backcrosses, $F_2$ intercrosses, $F_t$ populations (formed by randomly mating $F_1$s for t–1 generations), $F_{2:3}$ design ($F_2$ individuals are genotyped and then selfed), Design III ($F_2$ from two inbred lines are backcrossed to both parental lines). Thus, in some embodiments of the present invention, organisms represent a population, such as an $F_2$ population, and pedigree data for the $F_2$ population is known. This pedigree data is used to compute logarithm of the odds (lod) scores, as discussed in further detail below.

For many organisms, including humans, inbred lines that can be manipulated are not available and outbred populations must be used to perform linkage analysis. Linkage analysis using outbred populations detect QTLs responsible for within-population variation whereas linkage analysis using inbred populations detect QTLs responsible for fixed differences between lines, or even different species. Using within-population variation (outbred population), as opposed to fixed differences between populations (inbred population) results in decreased power in QTL detection. With inbred lines, all $F_1$ parents have identical genotypes (including the same linkage phase), so all individuals are informative, and linkage disequilibrium is maximized. As with inbred lines, a variety of designs have been proposed for obtaining samples with linkage disequilibrium required for linkage analysis. Typically, collections of relatives are relied upon.

The major difference between QTL analysis using inbred-line crosses versus outbred populations is that while the parents in the former are genetically uniform, parents in the latter are genetically variable. This distinction has several consequences. First, only a fraction of the parents from an outbred population are informative. For a parent to provide linkage information, it must be heterozygous at both a marker and a linked QTL, as only in this situation can a marker-trait association be generated in the progeny. Only a fraction of random parents from an outbred population are such double heterozygotes. With inbred lines, $F_1$'s are heterozygous at all loci that differ between the crossed lines, so that all parents are fully informative. Second, there are only two alleles segregating at any locus in an inbred-line cross design, while outbred populations can be segregating any number of alleles. Finally, in an outbred population, individuals can differ in marker-QTL linkage phase, so that an M-bearing gamete might by associated with QTL allele Q in one parent, and with q in another. Thus, with outbred populations, marker-trait associations might be examined separately for each parent. With inbred-line crosses, all $F_1$ parents have identical genotypes (including linkage phase), so one can average marker-trait associations over all off-spring, regardless of their parents. See Lynch and Walsh, *Genetics and Analysis of Quantitative Traits*, Sinauer Associates, Sunderland, Mass.

5.2.4. Model Free Versus Model Based Linkage Analysis

Linkage analyses can generally be divided into two classes: model-based linkage analysis and model-free linkage analysis. Model-based linkage analysis assumes a model for the mode of inheritance whereas model-free linkage analysis does not assume a mode of inheritance. Model-free linkage analyses are also known as allele-sharing methods and nonparametric linkage methods. Model-based linkage analyses are also known as "maximum likelihood" and "lod score" methods. Either form of linkage analysis can be used in the present invention.

Model-based linkage analysis is most often used for dichotomous traits and requires assumptions for the trait model. These assumptions include the disease allele frequency and penetrance function. For a disease trait, particularly those of interest to public health, the true underlying model is complex and unknown, so that these procedures are not applicable. The other form of linkage analysis (model-free linkage analysis) makes use of allele-sharing. Allele-sharing methods rely on the idea that relatives with similar phenotypes should have similar genotypes at a marker locus if and only if the marker is linked to the locus of interest. Linkage analyses are able to localize the locus of interest to a specific region of a chromosome and the scope of resolution is typically limited to no less than 5 cM or roughly 5000 kb. For more information on model-based and model-free linkage analysis, see Olson et al., 1999, Statistics in Medicine 18, p. 2961-2981; Lander and Schork 1994, Science 265, p. 2037; and Elston, 1998, Genetic Epidemiology 15, p. 565, as well as the sections below.

5.2.5. Known Programs for Performing Linkage Analysis

Many known programs can be used to perform linkage analysis in accordance with this aspect of the invention. One such program is MapMaker/QTL, which is the companion program to MapMaker and is the original QTL mapping software. MapMaker/QTL analyzes $F_2$ or backcross data using standard interval mapping. Another such program is QTL Cartographer, which performs single-marker regression, interval mapping (Lander and Botstein, 1989. *"Mapping Mendelian factors underlying Quantitative traits using RFLP linkage maps,"* Genetics 121: 185-199), multiple interval mapping and composite interval mapping (Zeng, 1993, *Proceedings of the National Academy of Sciences USA* 90: 10972-10976; and Zeng, 1994, Genetics 136: 1457-1468). QTL Cartographer permits analysis from $F_2$ or backcross populations. QTL Cartographer is available from statgen.ncsu.edu/qtlcart/cartographer.html (North Carolina State University). Another program that can be used by processing step 114 is Qgene, which performs QTL mapping by either single-marker regression or interval regression (Martinez and Curnow, 1994, Heredity 73:198-206). Using Qgene, eleven different population types (all derived from inbreeding) can be analyzed. Qgene is available from qgene.org. Yet another program is MapQTL, which conducts standard interval mapping (Lander and Botstein, Id), multiple QTL mapping (MQM) (Jansen, 1993, Genetics 135: 205-211; Jansen, 1994, Genetics 138: 871-881), and nonparametric mapping (Kruskal-Wallis rank sum test). MapQTL can analyze a variety of pedigree types including outbred pedigrees (cross pollinators). MapQTL is available from Plant Research International, Plant Research International, P.O. Box 16, 6700 AA Wageningen, The Netherlands; plant.wageningen-ur.nl/default.asp?section=products. Yet another program that may be used in some embodiments of processing step 210 is Map Manager QT, which is a QTL mapping program (Manly and Olson, 1999, Mammalian Genome 10: 327-334). Map Manager QT conducts single-marker regression analysis, regression-based simple interval mapping (Haley and Knott, 1992, Heredity 69, 315-324), composite interval mapping (Zeng 1993, *Proceedings of the National Academy of Sciences USA PNAS* 90: 10972-10976), and permutation tests. A description of Map Manager QT is provided by the reference Manly and Olson, 1999, Overview of QTL mapping software and introduction to Map Manager QT, Mammalian Genome 10: 327-334.

Yet another program that may be used to perform linkage analysis is MultiCross QTL, which maps QTL from crosses originating from inbred lines. MultiCross QTL uses a linear regression-model approach and handles different methods such as interval mapping, all-marker mapping, and multiple QTL mapping with cofactors. The program can handle a wide variety of simple mapping populations for inbred and outbred species. MultiCross QTL is available from Unitéde Biométrie et Intelligence Artificielle, INRA, 31326 Castanet Tolosan, France.

Still another program that can be used to perform linkage analysis is QTL Café. The program can analyze most populations derived from pure line crosses such as $F_2$ crosses, backcrosses, recombinant inbred lines, and doubled haploid lines. QTL Café incorporates a Java implementation of Haley & Knotts' flanking marker regression as well as Marker regression, and can handle multiple QTLs. The program allows three types of QTL analysis single marker ANOVA, marker regression (Kearsey and Hyne, 1994, *Theoretical Applied Genetics*, 89: 698-702), and interval mapping by regression, (Haley and Knott, 1992, Heredity 69: 315-324).

Yet another program that can be used to perform linkage analysis is MAPL, which performs QTL analysis by either interval mapping (Hayashi and Ukai, 1994, *Theoretical Applied Genetics* 87:1021-1027) or analysis of variance. Different population types including $F_2$, back-cross, recombinant inbreds derived from $F_2$ or back-cross after a given generations of selfing can be analyzed. Automatic grouping and ordering of numerous markers by metric multidimensional scaling is possible.

Another program that can be used for linkage analysis is R/qtl. This program provides an interactive environment for mapping QTLs in experimental crosses. R/qtl makes use of the hidden Markov model (HMM) technology for dealing with missing genotype data. R/qtl has implemented many HMM algorithms, with allowance for the presence of genotyping errors, for backcrosses, intercrosses, and phase-known four-way crosses. R/qtl includes facilities for estimating genetic maps, identifying genotyping errors, and performing single-QTL genome scans and two-QTL, two-dimensional genome scans, by interval mapping with Haley-Knott regression, and multiple imputation. R/qtl is available from Karl W. Broman, Johns Hopkins University, biosun01.biostat.jhsph.edu/~kbroman/qtl/.

Those of skill in the art will appreciate that there are several other programs and algorithms that can be used in the steps of the methods of the present invention where quantitative genetic analysis is needed, and all such programs and algorithms are within the scope of the present invention.

5.2.6. Model-Based Parametric Linkage Analysis

In model-based linkage analysis, (also termed "LOD score" methods or parametric methods), the details of a traits mode of inheritance is being modeled. Typically, particular values of the allele frequencies and the penetrance function are specified.

5.2.6.1. Interval Mapping Via Maximum Likelihood/Inbred Population

In one embodiment of the present invention, linkage analysis comprises QTL interval mapping in accordance with algorithms derived from those first proposed by Lander and Botstein, 1989, "Mapping Mendelian factors underlying quantitative traits using RFLP linkage maps," Genetics 121: 185-199. The principle behind interval mapping is to test a model for the presence of a QTL at many positions between two mapped marker loci. The model is fit, and its goodness is tested using a technique such as the maximum likelihood method. Maximum likelihood theory assumes that when a QTL is located between two biallelic markers, the genotypes (i.e. AABB, AAbb, aaBB, aabb for doubled haploid progeny) each contain mixtures of quantitative trait locus (QTL) genotypes. Maximum likelihood involves searching for QTL parameters that give the best approximation for quantitative trait distributions that are observed for each marker class. Models are evaluated by computing the likelihood of the observed distributions with and without fitting a QTL effect.

In some embodiments of the present invention, linkage analysis is performed using the algorithm of Lander, as implemented in programs such as GeneHunter. See, for example, Kruglyak et al., 1996, Parametric and Nonparametric Linkage Analysis: A Unified Multipoint Approach, American Journal of Human Genetics 58:1347-1363; Kruglyak and Lander, 1998, Journal of Computational Biology 5:1-7; and Kruglyak, 1996, American Journal of Human Genetics 58, 1347-1363. In such embodiments, unlimited markers may be used but pedigree size is constrained due to computational limitations. In other embodiments, the MENDEL software package is used. (See bimas.dcrt.nih.gov/linkage/ltools.html). In such embodiments, the size of the pedigree can be unlimited but the number of markers that can be used in constrained due to computation limitations. The techniques described in this Section typically require an inbred population.

5.2.6.2. Interval Mapping Using Linear Regression/Inbred Population

In some embodiments of the present invention, interval mapping is based on regression methodology and gives estimates of QTL position and effect that are similar to those given by the maximum likelihood method. Since the QTL genotypes are unknown in mapping based on regression methodology, genotypes are replaced by probabilities estimated using genotypes at the nearest flanking markers or for all linked markers. See, e.g., Haley and Knott, 1992, Heredity 69, 315-324; Jiang and Zeng, 1997, Genetica 101:47-58. The techniques described in this section typically require an inbred population.

5.2.7. Model-Free Nonparametric Linkage Analysis

Model-based linkage analysis (classical linkage analysis) calculates a lod score that represents the chance that a given loci in the genome is genetically linked to a trait, assuming a specific mode of inheritance for the trait. Namely the allele frequencies and penetrance values are included as parameters and are subsequently estimated. In the case of complex diseases, it is often difficult to model with any certainty all the causes of familial aggregation. In other words, when the trait exhibits non-mendelian segregation it can be difficult to obtain reliable estimates of penetrance values, including phenocopy risks, and the allele frequency of the disease mutation. Indeed it can be the case that different mutations at different loci have different kinds of effect on susceptibility, some major and some minor, some dominant and some recessive. If different modes of transmission are operative in different families, or if different loci interact in the same family, then no one transmission model may be appropriate. It is conceivable that if the transmission model for a linkage analysis is specified incorrectly the results produced from it will not be valid nor interpretable.

As a result of the difficulties described above, a variety of methods have been developed to test for linkage without the need to specify values for the parameters defining the transmission model, and these methods are termed model-free linkage analyses (meaning that they can be applied without regard to the true transmission model). Such methods are based on the premise that relatives who are similar with respect to the phenotype of interest will be similar at a marker locus, sharing identical marker alleles, only if a locus underlying the phenotype is linked to the marker.

Model-free linkage analyses (allele-sharing methods) are not based on constructing a model, but rather on rejecting a model. Specifically, one tries to prove that the inheritance pattern of a chromosomal region is not consistent with random Mendelian segregation by showing that affected relatives inherit identical copies of the region more often then expected by chance. Affected relatives should show excess allele sharing in regions linked to the QTL even in the presence of incomplete penetrance, phenocopy, genetic heterogeneity, and high-frequency disease alleles.

5.2.7.1. Identical by Descent—Affected Pedigree Member (IBD-APM) Analysis/Outbred Population In one embodiment, nonparametric linkage analysis involves studying affected relatives 246 (FIG. 1) in a pedigree 310 to see how often a particular copy of a chromosomal region is shared identical-by descent (IBD), that is, is inherited from a common ancestor within the pedigree. The frequency of IBD sharing at a locus can then be compared with random expectation. An identity-by-descent affected-pedigree-member (IBD-APM) statistic can be defined as:

$$T(s) = \sum_{i,j} x_{ij}(s).$$

where $x_{ij}(s)$ is the number of copies shared IBD at position s along a chromosome, and where the sum is taken over all distinct pairs (i,j) of affected relatives 246 in a pedigree 310. The results from multiple families can be combined in a weighted sum T(s). Assuming random segregation, T(s) tends to a normal distribution with a mean μ and a variance a that can be calculated on the basis of the kinship coefficients of the relatives compared. See, for example, Blackwelder and Elston, 1985, Genet. Epidemiol. 2, p. 85; Whittemore and Halpern, 1994, Biometrics 50, p. 118; Weeks and Lange, 1988, Am. J. Hum. Genet. 42, p. 315; and Elston, 1998, Genetic Epidemiology 15, p. 565. Deviation from random segregation is detected when the statistic (T-μ)/σ exceeds a critical threshold. The techniques in this section typically use an outbred population.

5.2.7.2. Affected Sib Pair Analysis/Outbred Population

Affected sib pair analysis is one form of IBD-APM analysis (Section 5.5.7.1). For example, two sibs can show IBD sharing for zero, one, or two copies of any locus (with a 25%-50%-25% distribution expected under random segregation). If both parents are available, the data can be partitioned into separate IBD sharing for the maternal and paternal chromosome (zero or one copy, with a 50%-50% distribution expected under random segregation). In either case, excess allele sharing can be measured with a $\chi^2$ test. In the ASP approach, a large number of small pedigrees (affected siblings and their parents) are used. DNA samples are collected from each organism and genotyped using a large collection of markers (e.g., microsatellites, SNPs). Then a check for functional polymorphism is performed. See, for example, Suarez et al., 1978, Ann. Hum. Genet. 42, p. 87; Weitkamp, 1981, N. Engl. J. Med. 305, p. 1301; Knapp et al., 1994, Hum. Hered. 44, p. 37; Holmans, 1993, Am. J. Hum. Genet. 52, p. 362; Rich et al., 1991, Diabetologica 34, p. 350; Owerbach and Gabbay, 1994, Am. J. Hum. Genet. 54, p. 909; and Berrettini et al., Proc. Natl. Acad. Sci. USA 91, p. 5918. For more information on Sib pair analysis, see Hamer et al., 1993, Science 261, p. 321.

In some embodiments, ASP statistics that test whether affected siblings pairs have a mean proportion of marker genes identical-by-descent that is >0.50 were computed. See, for example, Blackwelder and Elston, 1985, Genet. Epidemiol. 2, p. 85. In some embodiments, such statistics are computed using the SIBPAL program of the SAGE package. See, for example, Tran et al. 1991, (SIB-PAL) Sib-pair linkage program (Elston, New Orleans), Version 2.5. These statistics are computed on all possible affected pairs. In some embodiments the number of degrees of freedom of the t test is set at the number of independent affected pairs (defined per sibship as the number of affected individuals minus 1) in the sample instead of the number of all possible pairs. See, for example, Suarez and Eerdewegh, 1984, Am. J. Med. Genet. 18, p. 135. The techniques in this section typically use an outbred population.

5.2.7.3. Identical by State—Affected Pedigree Member (IBS-APM) Analysis/Outbred Population In some instances, it is not possible to tell whether two relatives inherited a chromosomal region IBD, but only whether they have the same alleles at genetic markers in the region, that is, are identical by state (IBS). IBD can be inferred from IBS when a dense collection of highly polymorphic markers has been examined, but the early stages of genetic analysis can involve sparser maps with less informative markers so that IBD status can not be determined exactly. Various methods are available to handle situations in which IBD cannot be inferred from IBS. One method infers IBD sharing on the basis of the marker data (expected identity by descent affected-pedigree-member; IBD-APM). See, for example, Suarez et al., 1978, Ann. Hum. Genet. 42, p. 87; and Amos et al., 1990, Am J. Hum. Genet. 47, p. 842. Another method uses a statistic that is based explicitly on IBS sharing (an IBS-APM method). See, for example, Weeks and Lange, 1988, Am J. Hum. Genet. 42, p. 315; Lange, 1986, Am. J. Hum. Genet. 39, p. 148; Jeunemaitre et al., 1992, Cell 71, p. 169; and Pericak-Vance et al., 1991, Am. J. Hum. Genet. 48, p. 1034.

In one embodiment the IBS-APM techniques of Weeks and Lange, 1988, Am J. Hum. Genet. 42, p. 315; and Weeks and Lange, 1992, Am. J. Hum. Genet. 50, p. 859 are used. Such techniques use marker information of affected individuals to test whether the affected persons within a pedigree are more similar to each other at the marker locus than would be expected by chance. In some embodiments, the marker similarity is measured in terms of identity by state. In some embodiments, the APM method uses a marker allele frequency weighting function, $f(p)$, where p is the allele frequency, and the APM test statistics are presented separately for each of three different weighting functions, $f(p)=1$, $f(p)=1/\sqrt{p}$, and $f(p)=1/p$. Whereas the second and third functions render the sharing of a rare allele among affected persons a more significant event, the first weighting function uses the allele frequencies only in calculation of the expected degree of marker allele sharing. The third function, $f(p)=1/p$, can lead (more frequently than the first two) to a non-normal distribution of the test statistic. The second function is a reasonable compromise for generating a normal distribution of the test statistic while incorporating an allele frequency function. In some instances, the APM test statistics are sensitive to marker locus and allele frequency misspecification. See, for example, Babron, et al, 1993, Genet. Epidemiol. 10, p. 389. In some embodiments, allele frequencies are estimated from the pedigree data using the method of Boehnke, 1991, Am J. Hum. Genet. 48, p. 22, or by studying alleles. See, also, for example, Berrettini et al., 1994, Proc. Natl. Acad. Sci. USA 91, p. 5918.

In some embodiments, the significance of the APM test statistics is calculated from the theoretical (normal) distribution of the statistic. In addition, numerous replicates (e.g., 10,000) of these data, assuming independent inheritance of marker alleles and disease (i.e., no linkage), are simulated to assess the probability of observing the actual results (or a more extreme statistic) by chance. This probability is the empirical P value. Each replicate is generated by simulating an unlinked marker segregating through the actual pedigrees. An APM statistic is generated by analyzing the simulated data set exactly as the actual data set is analyzed. The rank of the observed statistic in the distribution of the simulated statistics determines the empirical P value. The techniques in this section typically use an outbred population.

5.2.7.4. Quantitative Traits

Model-free linkage analysis can also be applied to quantitative traits. An approach proposed by Haseman and Elston, 1972, Behav. Genet 2, p. 3, is based on the notion that the phenotypic similarity between two relatives should be correlated with the number of alleles shared at a trait-causing locus. Formally, one performs regression analysis of the squared difference $\Delta^2$ in a trait between two relatives and the number x of alleles shared IBD at a locus. The approach can be suitably generalized to other relatives (Blackwelder and Elston, 1982, Commun. Stat. Theor. Methods 11, p. 449) and multivariate phenotypes (Amos et al., 1986, Genet. Epidemiol. 3, p. 255). See also, Marsh et al., 1994, Science 264, p. 1152, and Morrison et al., 1994, Nature 367, p. 284; Amos, 1994, Am. J. Hum Genet. 54, p. 535; and Elston, Am J. Hum. Genet. 63, p. 931.

5.3. QTL ANALYSIS USING CELLULAR CONSTITUENT LEVELS

This section describes an aspect of the present invention that uses a form of quantitative genetic analysis 114 (FIG. 1) in which subclass i is analyzed using a novel form of QTL analysis. In this form of QTL analysis, the transcription levels of a plurality of genes in each patient or specimen in subclass i are each treated as a phenotypic trait. The expression level measurement of each gene in each organism in subclass i is transformed into a corresponding expression statistic. An "expression level measurement" of a gene can be, for example, a measurement of the level of its encoded RNA (or cDNA) or proteins or activity levels of encoded proteins. In some embodiments, this transformation is a normalization routine in which raw gene expression data is normalized to yield a mean log ratio, a log intensity, and a background-corrected intensity.

Figure 3:
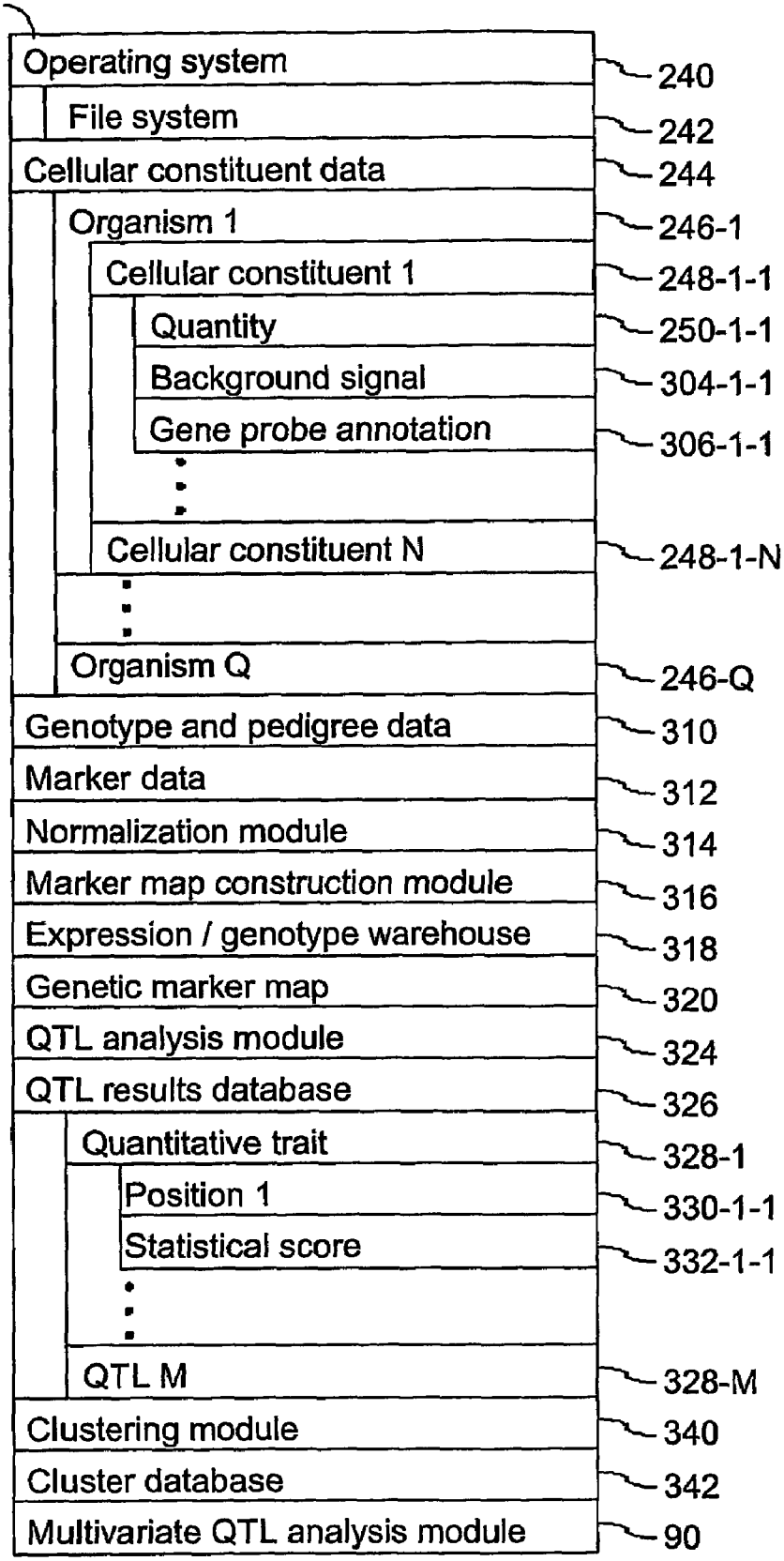
FIG. 3 illustrates a memory in a computer system that includes the data structures and modules that facilitate quantitative trait loci analysis using cellular constituent levels in accordance with a preferred embodiment of the present invention.
Figure 4:
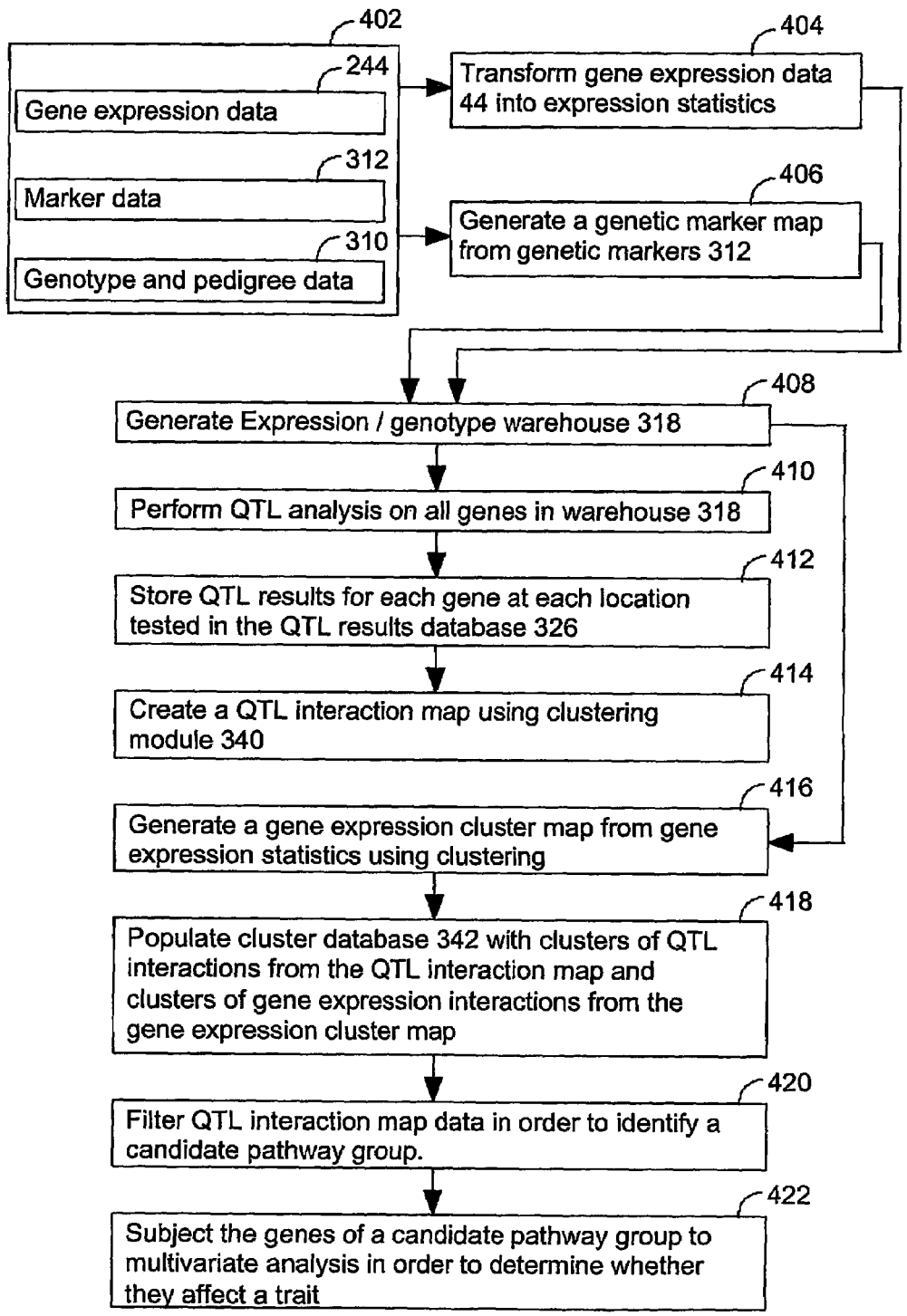
FIG. 4 illustrates processing steps for a quantitative trait loci analysis algorithm using cellular constituent levels in accordance with a preferred embodiment of the present invention.

To further illustrate the aspects of quantitative genetic analysis 114 (FIG. 1) in accordance with this aspect of the invention, the data structures and modules found in a particular memory 224 that facilitates this embodiment of the present invention are illustrated in FIG. 3. Further, processing steps in accordance with this aspect of the present invention are illustrated in FIG. 4. In a preferred embodiment in accordance with the aspect of the invention described in this section, cellular constituent data 244 is gene expression data from a gene expression study. However, this aspect of the present invention may be used with other forms of cellular constituent data such as translational state measurements (See, e.g., Section 5.12) or other aspects of the biological states (See Section 5.13). This aspect of the present invention uses genotype data 310 (FIG. 3) from an experimental cross or human cohort under study. In some embodiments, genotype data 310 includes pedigree data. In one embodiment, cellular constituent data 244 (FIG. 3) consists of the processed microarray images for each individual (organism) 246 in a population under study. Such data comprises, for each individual 246, intensity information 250 for each gene 248 represented on the array for each individual profiled, background signal information 304, and associated annotation information 306 describing the gene probe.

Genotype and/or pedigree data 310 comprises the actual alleles for each marker typed in each individual under study, in addition to the relationships between these individuals. The extent of the relationships between the individuals under study may be as simple as an $F_2$ population or as complicated as extended human family pedigrees. Exemplary sources of genotype and pedigree data 310 are described in Section 5.20.1, infra.

Marker data 312 (FIG. 3) at regular intervals across the genome under study or in gene regions of interest is used to monitor segregation or detect associations in a population of interest. Marker data 312 comprises those markers that will be used in the population under study to assess genotype. In one embodiment, marker data 312 comprises the names of the markers, the type of markers (e.g., SNP, microsatellite, etc.), as well as the physical and genetic location of the markers in the genomic sequence. Further, in some embodiments, marker data 312 comprises the different alleles associated with each marker. For example, a particular microsatellite marker consisting of 'CA' repeats may have represented ten different alleles in the population under study, with each of the ten different alleles in turn consisting of some number of repeats. Representative marker data 312 in accordance with one embodiment of the present invention is found in Section 5.5, infra. In one embodiment of the present invention, the genetic markers used comprise single nucleotide polymorphisms (SNPs), microsatellite markers, restriction fragment length polymorphisms, short tandem repeats, DNA methylation markers, or sequence length polymorphisms.

Genetic marker map 320 (FIG. 3) is constructed from a set of genetic markers associated with the plurality of organisms. Then, for each gene G in a plurality of genes expressed by an organism in the population, a quantitative trait locus (QTL) analysis is performed using the genetic marker map 320 in order to produce QTL data. A set of expression statistics represents the quantitative trait used in each QTL analysis. QTL analyses are explain in greater detail, infra, in conjunction with FIG. 4, element 410. This set of expression statistics, for any given gene G, comprises an expression statistic for gene G, for each organism in the plurality of organisms. Next, the QTL data obtained from each QTL analysis is clustered to form a QTL interaction map. Identification of tightly clustered QTLs in the QTL interaction map helps to identify genes that are genetically interacting. This information, in turn, helps to elucidate biological pathways that are affected by complex traits, such as human disease. In some embodiments of the present invention, tightly clustered QTLs in the QTL interaction map are considered candidate pathway groups. These candidate pathway groups are subjected to multivariate analysis in order to verify whether the genes in the candidate pathway group affect a particular complex trait.

Detailed processing steps in accordance with one embodiment of QTL analysis using cellular constituent levels will be described in conjunction with FIG. 4. This embodiment begins with the cellular constituent data 244 from a gene expression study and a genotype data 310 from an experimental cross or human cohort under study (FIG. 3; FIG. 4, step 402). In one embodiment, data 310 comprises genotype data from each organism in the population under study for each of the markers in genetic marker map 320. In some embodiments, genotype data 310 includes phenotype data. However, there is no requirement that data structure 310 include pedigree data if linkage analysis is not used in any of the steps illustrated in FIG. 4. Once starting data are assembled, the first step (FIG. 4, step 404) is to transform gene expression data 244 into expression statistics that are used to treat each gene transcript abundance in gene expression data 244 as a quantitative trait. Gene expression data 244 (FIG. 3) comprises gene expression data for a plurality of genes. In one embodiment, the plurality of genes comprises at least five genes. In another embodiment, the plurality of genes comprises at least one hundred genes, at least one thousand genes, at least twenty thousand genes, or more than thirty thousand genes. The expression statistics commonly used as quantitative traits in the analyses in one embodiment of the present invention include, but are not limited to, the mean log ratio, log intensity, and background-corrected intensity. In other embodiments, other types of expression statistics are used as quantitative traits. In one embodiment, this transformation (FIG. 4, step 404) is performed using normalization module 314 (FIG. 3). In such embodiments, the expression level of a plurality of genes in each organism under study are normalized.

Any normalization routine can be used by normalization module 314. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be run. Exemplary normalization routines in accordance with the present invention are disclosed in more detail in Section 5.6, infra.

The expression statistics formed from the transformation are then stored in Expression/genotype warehouse 318, where they are ultimately matched with the corresponding genotype information. In addition to the generation of expression statistics from gene expression data 244, a genetic marker map 320 is generated from genetic markers 312 (FIG. 3; FIG. 4, step 406). In one embodiment of the present invention, a genetic marker map 320 is created using marker map construction module 316 (FIG. 3). Optionally, genotype probability distributions for the individuals under study are computed. Genotype probability distributions take into account information such as marker information of parents, known genetic distances between markers, and estimated genetic distances between the markers.

Once the expression data has been transformed into corresponding expression statistics and genetic marker map 320 has been constructed, the data is transformed into a structure that associates all marker, genotype and expression data for input into QTL analysis software. This structure is stored in expression/genotype warehouse 318 (FIG. 3; FIG. 4, step 408).

A quantitative trait locus (QTL) analysis is performed using data corresponding to each gene in a plurality of genes as a quantitative trait (FIG. 4, step 410). For 20,000 genes, this results in 20,000 separate QTL analyses. In one embodiment, each QTL analysis is performed by QTL analysis module 324 (FIG. 3). In one example, each QTL analysis steps through each chromosome in the genome of the organism of interest. Linkages to the quantitative trait under consideration are tested at each step or location along the length of the chromosome. In such embodiments, each step or location along the length of the chromosome is at regularly defined intervals. In some embodiments, these regularly defined intervals are defined in Morgans or, more typically, centiMorgans (cM). A Morgan is a unit that expresses the genetic distance between markers on a chromosome. A Morgan is defined as the distance on a chromosome in which one recombinational event is expected to occur per gamete per generation. In some embodiments, each regularly defined interval is less than 100 cM. In other embodiments, each regularly defined interval is less than 10 cM, less than 5 cM, or less than 2.5 cM.

Figure 5:
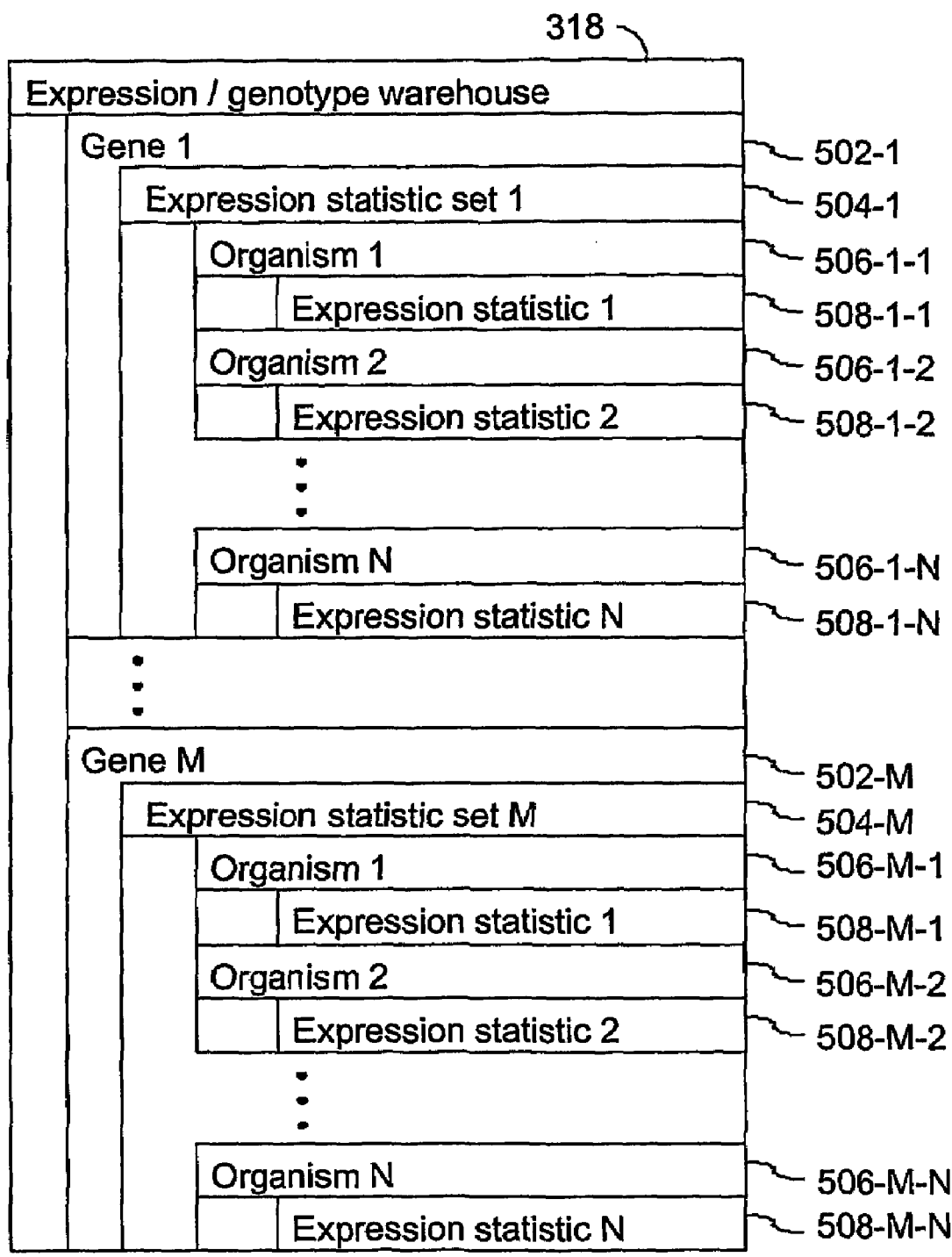
FIG. 5 illustrates an expression/genotype warehouse in accordance with one embodiment of the present invention.

In each QTL analysis, data corresponding to a gene selected from a plurality of genes under study is used as a quantitative trait. More specifically, for any given gene, the quantitative trait used in the QTL analysis is an expression statistic set, such as set 504 (FIG. 5). Expression statistic set 504 (e.g., the quantitative trait) comprises the corresponding expression statistic 508 for the gene 502 from each organism 506 in the population under study. Accordingly, in one embodiment of the present invention, each QTL analysis (FIG. 4, step 410) comprises: (i) testing for linkage between a position in a chromosome and the quantitative trait (expression statistic set 504) used in the quantitative trait locus (QTL) analysis, (ii) advancing the position in the genome by an amount, and (iii) repeating steps (i) and (ii) until all or a portion of the genome has been tested. If the genetic length of a given chromosome is N cM and 1 cM steps are used, then N different tests for linkage are performed on the given chromosome.

In some embodiments, the QTL data produced from each respective QTL analysis comprises a logarithmic of the odds score (LOD) computed at each position tested in the genome under study. A lod score is a statistical estimate of whether two loci are likely to lie near each other on a chromosome and are therefore likely to be genetically linked. In the present case, a lod score is a statistical estimate of whether a given position in the genome under study is linked to the quantitative trait corresponding to a given gene. In Section 5.7, infra, lod scores are further described. The generation of lod scores requires pedigree data. Accordingly, in embodiments in which a lod score is generated, processing step 410 is essentially a linkage analysis, as described in Section 5.2, with the exception that the quantitative trait under study is derived from data such as cellular constituent expression statistics rather than classical phenotypes such as eye color.

In situations where pedigree data is not available, genotypic data from each of the different organisms 246 (FIG. 3) for each marker in genetic marker map 320 can be compared to each quantitative trait (expression statistic set 504) using association analysis, as described in Section 5.4 in order to identify a regions of the genome that have allelic forms associated with differences in expression statistic set 504. In order to provide uniform nomenclature, regions identified by association analysis are referred to herein as QTL.

Regardless of whether linkage analysis or association analysis is used in processing step 410, the results of each QTL analysis are stored in QTL results database 326 (FIG. 3; FIG. 4, step 412). The quantitative trait 328 corresponding to each gene in a plurality of genes analyzed by QTL analysis is found in QTL results database 326. For each quantitative trait 328 (expression statistic set 504), QTL results database 326 comprises all positions 330 in the genome of the organism that were tested for linkage to the quantitative trait. Positions 330 are obtained from genetic marker map 320. Further, for each position 330, genotype data 310 provides the genotype at the position 330, for each organism in the plurality of organisms under study. Provision of such data allows for statistical analysis designed to identify QTL in the genome of the species under study that are associated with particular quantitative traits 328. For each position 330 analyzed by QTL analysis, a statistical measure, such as a maximum lod score between the position and the quantitative trait 328, is listed. Thus, data structure 326 includes all the positions in the genome of the organism of interest that are genetically linked to each quantitative trait 328 tested.

FIG. 6 provides a more detailed illustration of QTL results database 326. Each statistical score 332 measures the degree to which a given position 330 is linked to the corresponding quantitative trait 328. The set of statistical scores 332 for any given quantitative trait 328 may be considered a QTL vector. Thus, in one embodiment of the present invention, a QTL vector is created for each gene tested in the chromosome of the organism studied. In a more typical embodiment, a QTL vector is created for each gene tested in the entire genome of the organism studied. The QTL vector comprises the statistical score 332 at each position tested by the QTL analysis corresponding to the gene. In addition to QTL vectors, gene expression vectors may be constructed from transformed gene expression data stored in warehouse 318. Each gene expression vector represents the transformed expression level of the gene from each organism in the population of interest. Thus, any given gene expression vector comprises the transformed expression level of the gene from a plurality of different organisms in the population of interest.

With the QTL vectors generated, the next step of the present invention involves the generation of QTL interaction maps from the QTL vectors (FIG. 4, step 414). To generate QTL interaction maps, the QTL vectors are clustered into groups of QTLs based on the strength of interaction between the QTL vectors. In some embodiments of the present invention, QTL interaction maps are generated by clustering module 340. In one embodiment of the present invention, agglomerative hierarchical clustering is applied to the QTL vectors. In this clustering, similarity is determined using Pearson correlation coefficients between the QTL vectors pairs. In other embodiments, the clustering of the QTL data from each QTL analysis comprises application of a hierarchical clustering technique, application of a k-means technique, application of a fuzzy k-means technique, application of Jarvis-Patrick clustering technique, application of a self-organizing map or application of a neural network. In some embodiments, the hierarchical clustering technique is an agglomerative clustering procedure. In other embodiments, the agglomerative clustering procedure is a nearest-neighbor algorithm, a farthest-neighbor algorithm, an average linkage algorithm, a centroid algorithm, or a sum-of-squares algorithm. In still other embodiments, the hierarchical clustering technique is a divisive clustering procedure. Illustrative clustering techniques that may be used to cluster QTL vectors are described in Section 5.8, infra.

Since each QTL corresponds to a given gene in a plurality of genes in the population of interest, QTL interaction maps provide information on which QTLs are linked. Such information may be combined with gene expression data to help elucidate biological pathways that affect complex traits. In one embodiment of the present invention, a gene expression cluster map is constructed from gene expression statistics (FIG. 4, step 416). A plurality of gene expression vectors are created. Each gene expression vector in the plurality of gene expression vectors represents the expression level, activity, or degree of modification of a particular cellular constituent, such as a gene or gene product, in a plurality of cellular constituents in the population of interest. Then, a plurality of correlation coefficients is computed. Each correlation coefficient in the plurality of correlation coefficients is computed between a gene expression vector pair in the plurality of gene expression vectors. Then, the plurality of gene expression vectors are clustered based on the plurality of correlation coefficients in order to form the gene expression cluster map. In one embodiment of the present invention, each correlation coefficient in the plurality of correlation coefficients is a Pearson correlation coefficient. In another embodiment of the present invention, clustering of the plurality of gene expression vectors comprises application of a hierarchical clustering technique, application of a k-means technique, application of a fuzzy k-means technique, application of a self-organizing map or application of a neural network. In one embodiment of the present invention, the hierarchical clustering technique is an agglomerative clustering procedure such as a nearest-neighbor algorithm, a farthest-neighbor algorithm, an average linkage algorithm, a centroid algorithm, or a sum of squares algorithm. In another embodiment of the invention, the hierarchical clustering technique is a divisive clustering procedure. Illustrative clustering techniques that may be used to cluster the gene expression vectors are described in Section 5.8, infra.

At this stage, the QTL interaction map provides information on individual genes in gene expression clusters found in gene expression cluster maps. Gene expression clusters found in gene expression cluster maps may be considered to be in the same candidate pathway group. QTL interactions can be used to identify those genes that are "closer" together in a candidate pathway group than other genes. Furthermore, genes in gene expression clusters found in a gene expression map that are not at all genetically interacting may be downweighted with respect to those genes that are genetically interacting. In this way, QTL interaction maps help to refine candidate pathway groups that are identified in gene expression cluster maps.

In one embodiment of the present invention, the next step involves mapping all probes used to generate gene expression data 244 (FIG. 3) to their respective genomic and genetic coordinates. This information aids in establishing the potential for a given gene to correspond directly to a particular QTL (e.g., that a gene actually was the QTL).

In one embodiment of the present invention, clusters of QTL interactions from the QTL interaction maps and clusters of gene expression interactions from the gene expression cluster maps are represented in cluster database 342 (FIG. 3; FIG. 4, step 418). Cluster database 342 is used to identify the patterns that feed a multivariate QTL analyses. In addition to the QTL and gene expression cluster information, the physical locations of the QTLs and genes are represented in cluster database 342.

In some embodiments of the present invention, a gene is identified in the QTL interaction map by filtering the QTL interaction map in order to obtain a candidate pathway group. In one embodiment, this filtering comprises selecting those QTL for the candidate pathway group that interact most strongly with another QTL in the QTL interaction map. In some embodiments, the QTL that interact most strongly with another QTL in the QTL interaction map are all QTL, represented in the QTL interaction map, that share a correlation coefficient with another QTL in the QTL interaction map that is higher than 75%, 85%, or 95% of all correlation coefficients computed between QTLs in the QTL interaction map.

In one embodiment of the present invention, cluster database 342 is used to associate a gene with a trait. Representative traits include, but are not limited to, disease status, tumor stage, triglyceride levels, blood pressure, and/or diagnostic test results. In this embodiment, the QTL interaction map and/or data stored in cluster database 342 is filtered in order to obtain a candidate pathway group (FIG. 4, step 420). This filtering comprises identifying a QTL in the candidate pathway group in the gene expression cluster map. In one example in accordance with this embodiment of the present invention, the QTL interaction map is filtered by identifying groups of QTL within the QTL interaction map that interact closely with one another. The genes associated with each QTL in the groups of QTL that interact closely with one another in a QTL interaction map are considered candidate pathway groups. In some embodiments, the filtering further comprises looking up the genes in each of the candidate pathway groups in the gene expression interaction map. Of interest is whether the genes in the candidate pathway groups identified in the QTL interaction map interact closely with each other in the gene expression interaction map.

In general, patterns of interest can be identified by querying cluster database 342. Such groups can be identified by filtering on strength of QTL-QTL interactions, which identifies those genes that are most strongly genetically interacting, and then combining this information with genes that are the most tightly clustered within these groups. The size of these groups is easily adjusted by scaling the threshold parameters used to identify QTL and/or genes that are interacting. Such groups could themselves be considered putative pathway groups. However, another approach is to fit the groups to genetic models in order to test whether the genes are actually part of the same pathway.

In one embodiment in accordance with the present invention, the degree to which each QTL making up a candidate pathway group belongs with other QTLs within the candidate pathway group is tested by fitting a multivariate statistical model to the candidate pathway group (FIG. 4; step 422). Multivariate statistical models have the capability of simultaneously considering multiple quantitative traits, modeling epistatic interactions between the QTL, and testing other interesting variations that determine whether genes in a candidate pathway group belong to the same or related biological pathway. Specific tests can be done to determine if the traits under consideration are actually controlled by the same QTL (pleiotropic effects) or if they are independent. Exemplary multivariate statistical models that may be used in accordance with the present invention are found in Section 5.9, infra.

The results of the multivariate QTL analysis are used to "validate" the candidate pathway groups. These validated groups are then represented in a database and made available for the final stage of analysis, which involves reconstructing the pathway. At this stage the database comprises genes that are under some kind of common genetic control, interact to some degree at the expression level, and that have been shown to interact strongly enough at these different levels to perhaps belong to the same or related pathways. Thus, in some instances, the association of a gene with a trait exhibited by one or more organisms in a population of interest results in the placement of the gene in a pathway group that comprises genes that are part of the same or related pathway.

A subsequent step involves an attempt to partially reconstruct the pathways within a given pathway group. For each candidate pathway group, the interactions between the representative QTL vectors and gene expression vectors can be examined. Furthermore, QTL and probe location information can be used to begin to piece together causal pathways. In addition, graphical models can be fit to the data using the interaction strengths, QTL overlap and physical location information accumulated from the previous steps to weight and direct the edges that link genes in a candidate pathway group. Application of such graphical models is used to determine which genes are more closely linked in a candidate pathway group and therefore suggests models for constraining the topology of the pathway. Thus, such models test whether it is more likely that the candidate pathway proceeds in a particular direction, given the evidence provided by the interactions, QTL overlaps, and physical QTL/probe location. The end result of this process, after starting with expression data, genotype data, and marker data, is a set of pathway groups consisting of genes that are supported as being part of the same or related pathway, and causal information that indicates the exact relationship of genes in the pathway (or of a partial set of genes in the pathway).

5.4. ASSOCIATION ANALYSIS

This section describes a number of association tests that can be used in the present invention. Association studies can be done with samples of pedigrees or samples of unrelated individuals. Further, association studies can be done for a dichotomous trait (e.g., disease) or a quantitative trait. See, for example, Nepom and Ehrlich, 1991, Annu. Rev. Immunol. 9, p. 493; Strittmatter and Roses, 1996, Annu. Rev. Neurosci. 19, p. 53; Vooberg et al., 1994, Lancet 343, p. 1535; Zoller et al., Lancet 343, p. 1536; Bennet et al., 1995, Nature Genet. 9, p. 284; Grant et al., 1996, Nature Genet. 14, p. 205; and Smith et al., 1997, Science 277, p. 959. As such, association studies test whether a disease and an allele show correlated occurrence across the population, whereas linkage studies determine whether there is correlated transmission within pedigrees.

Whereas linkage analysis involves the pattern of transmission of gametes from one generation to the next, association is a property of the population of gametes. Association exists between alleles at two loci if the frequency, with which they occur within the same gamete, is different from the product of the allele frequencies. If this association occurs between two linked loci, then utilizing the association will allow for fine localization, since the strength of association is in large part due to historical recombinations rather than recombination within a few generations of a family. In the simplest scenario, association arises when a mutation, which causes disease, occurs at a locus at some time, $t_o$. At that time, the disease mutation occurs on a specific genetic background composed of the alleles at all other loci; thus, the disease mutation is completely associated with the alleles of this background. As time progresses, recombination occurs between the disease locus and all other loci, causing the association to diminish. Loci that are closer to the disease locus will generally have higher levels of association, with association rapidly dropping off for markers further away. The reliance of association on evolutionary history can provide localization to a region as small as 50-75 kb. Association is also called linkage disequilibrium. Association (linkage disequilibrium) can exist between alleles at two loci without the loci being linked.

Two forms of association analysis are discussed in the sections below, population based association analysis and family based association analysis. More generally, those of skill in the art with appreciate that there are several different forms of association analysis, and all such forms of association analysis can be used in step 114 of FIG. 1 and/or step 410 of FIG. 4.

In some embodiments, whole genome association studies are performed in accordance with the present invention. Two methods can be used to perform whole-genome association studies, the "direct-study" approach and the "indirect-study" approach. In the direct-study approach, all common functional variants of a given gene are catalogued and tested directly to determine whether there is an increased prevalence (association) of a particular functional variant in affected individuals within the coding region of the given gene. The "indirect-study" approach uses a very dense marker map (derived from marker genotype data 80 of FIG. 1, for example) that is arrayed across both coding and noncoding regions. A dense panel of polymorphisms (e.g., SNPs) from such a map can be tested in controls to identify associations that narrowly locate the neighborhood of a susceptibility or resistance gene. This strategy is based on the hypothesis that each sequence variant that causes disease must have arisen in a particular individual at some time in the past, so the specific alleles for polymorphisms (haplotype) in the neighborhood of the altered gene in that individual (organism 246, FIG. 2) can be inherited in all of his or her descendants. The presence of a recognizable ancestral haplotype therefore becomes an indicator of the disease-associated polymorphism. In actuality, some of the alleles will be in association while others will not due to recombination occurring between the mutation and other polymorphisms.

5.4.1. Population-Based (Model-Free) Association Analysis

In population-based (model-free) association studies, allele frequencies in afflicted organisms are contrasted with allele frequencies in control organisms in order to determine if there is an association between a particular allele and a complex trait. Population-based association studies for dichotomous traits are also referred to as case-control studies. A case-control study is based on the comparison of unrelated affected and unaffected individuals from a population. An allele A at a gene of interest is said to be associated with the phenotype if it occurs at significantly higher frequency among affected compared with control individuals. Statistical significance can be tested by a number a methods, including, but not limited to, logistic regression. Association studies are discussed in Lander, 1996, Science 274, 536; Lander and Schork, 1994, Science 265, 2037; Risch and Merikangas, 1996, Science 273, 1516; and Collins et al., 1997, Science 278, 1533.

As is true for case-control studies generally, confounding is a problem for inferring a causal relationship between a disease and a measured risk factor using population-based association analysis. One approach to deal with confounding is the matched case-control design, where individual controls are matched to cases on potential confounding factors (for example, age and sex) and the matched pairs are then examined individually for the risk factor to see if it occurs more frequently in the case than in its matched control. In some embodiments, cases and controls are ethnically comparable. In other words, homogeneous and randomly mating populations are used in the association analysis. In some embodiments, the family-based association studies described below are used to minimize the effects of confounding due to genetically heterogeneous populations. See, for example, Risch, 2000, Nature 405, p. 847.

5.4.2. Family-Based Association Analysis

Family-based association analysis is used in some embodiments of the invention. In some embodiments, each affected organism is matched with one or more unaffected siblings (see, for example, Curtis, 1997, Ann. Hum. Genet. 61, p. 319) or cousins (see, for example, Witte, et al., 1999, Am J. Epidemiol. 149, p. 693) and analytical techniques for matched case-control studies is used to estimate effects and to test a hypotheses. See, for example, Breslow and Day, 1989, Statistical methods in cancer research I, The analysis of case-control studies 32, Lyon: IARC Scientific Publications. The following subsections describe some forms of family-based association studies. Those of skill in the art will recognize that there are numerous forms of family-based association studies and all such methodologies can be used in the present invention, including during step 114 (FIG. 1) and step 410 (FIG. 4).

5.4.2.1. Haplotype Relative Risk Test

In some embodiments, the haplotype relative risk test is used. In the haplotype relative risk method, all marker alleles compared arise from the same person. The marker alleles that parents transmit to an affected offspring (case alleles) are compared with those that they do not transmit to such an offspring (control alleles). One can also compare transmitted and nontransmitted genotypes. Consider the 2n parents of n affected persons. This population can be classified into a fourfold table according to whether the transmitted allele is a marker allele (M) or some other allele $\overline{M}$ and according to whether the nontransmitted allele is similarly M or $\overline{M}$:

|                   | Nontransmitted allele | | |
| --- | --- | --- | --- |
| Transmitted allele | M | $\overline{M}$ | Total |
| M | a | b | a + b |
| $\overline{M}$ | c | d | c + d |
|  | a + c | b + d | 2n = a + b + c + d |

To test for association, a determination is made as to whether the proportion of M alleles that are transmitted, a/(a+b), differs significantly from the proportion of M alleles that are nontransmitted, a/(a+c). One appropriate statistical test for this determination is comparison of $(b-c)^2/(b+c)$ to a chi-square distribution with one degree of freedom when the sample is large.

The row totals for the table above are the numbers of transmitted alleles that are M and $\overline{M}$, while the column totals are the numbers of nontransmitted alleles that are M and $\overline{M}$. These four totals can be put into a fourfold table that classifies the 4n parental alleles, rather than the 2n parents:

| Marker allele | Transmitted | Non-transmitted | Total |
| --- | --- | --- | --- |
| M | a + b | a + c | 2a + b + c |
| $\overline{M}$ | c + d | b + d | b + c + 2d |
| Total | 2n | 2n | 4n |

The haplotype relative risk ratio is defined as (a+b)(c+d)/(a+c)(c+d). A chi-square distribution using one degree of freedom can be used to determine whether the haplotype relative risk ratio differs significantly from one. See, for example, Rudorfer, et al., 1984, Br. J. Clin. Pharmacol. 17, 433; Mueller and Young, 1997, *Emery's Elements of Medical Genetics*, Kalow ed., p. 169-175, Churchill Livingstone, Edinburgh; and Roses, 2000, Nature 405, p. 857, Elson, 1998, Genetic Epidemilogy, 15, p. 565.

5.4.2.2. Transmission Equilibrium Test

In some embodiments, the transmission equilibrium test (TDT) is used. TDT considers parents who are heterozygous for an allele and evaluates the frequency with which that allele is transmitted to affected offspring. By restriction to heterozygous parents, the TDT differs from other model-free tests for association between specific alleles of a polymorphic marker and a disease locus. The parameters of that locus, genotypes of sampled individuals, linkage phase, and recombination frequency are not specified. Nevertheless, by considering only heterozygous parents, the TDT is specific for association between linked loci.

TDT is a test of linkage and association that is valid in heterogeneous populations. It was originally proposed for data consisting of families ascertained due to the presence of a diseased child. The genetic data consists of the marker genotypes for the parents and child. The TDT is based on transmissions, to the diseased child, from heterozygous parents, or parents whose genotypes consist of different alleles. In particular, consider a biallelic marker with alleles $M_1$ and $M_2$. The TDT counts the number of times, $n_{12}$, that $M_1M_2$ parents transmit marker allele $M_1$ to the diseased child and the number of times, $n_{21}$, that $M_2$ is transmitted. If the marker is not linked to the disease locus, i.e. $\theta=0.5$, or if there is no association between $M_1$ and the disease mutation, then conditional on the number of heterozygous parents, and in the absence of segregation distortion, $n_{12}$ is distributed binomially: $B(n_{12}+n_{21}, 0.5)$. The null hypothesis of no linkage or no association can be tested with the statistic $$T_{TDT} = \frac{(n_{12} - n_{21})^2}{n_{12} + n_{21}}$$

with statistical significance level approximated using the $\chi 2$ distribution with one df or computed exactly with the binomial distribution. When transmissions from more than one diseased child per family are included in the TDT statistic, the test is valid only as a test of linkage.

Several extensions of the TDT test have been proposed and all such extensions are within the scope of the present invention. See, for example, Mortin and Collins, 1998, Proc. Natl. Acad. Sci. USA 95, p. 11389; Terwilliger, 1995, Am J Hum Genet 56, p. 777. See also, for example, Mueller and Young, 1997, Emery's Elements of Medical Genetics, Kalow ed., p. 169-175, Churchill Livingstone, Edinburgh; Zhao et al., 1998, Am. J. Hum. Genet. 63, p. 225; Roses, 2000, Nature 405, p. 857; Spiehnan et al., 1993, Am J. Hum. Genet. 52, p. 506; and Ewens and Spielman; Am. H. Hum. Genet. 57, p. 455.

5.4.2.3. Sibship-Based Test

In some embodiments, the sibship-based test is used. See, for example, Wiley, 1998, Cur. Pharmaceut. Des. 4, p. 417; Blackstock and Weir, 1999, Trends Biotechnol. 17, p. 121; Kozian and Kirschbaum, 1999, Trends Biotechnol. 17, p. 73;

Rockett et al., Xenobiotica 29, p. 655; Roses, 1994, J. Neuropathol. Exp. Neurol 53, p. 429; and Roses, 2000, Nature 405, p. 857.

5.5. SOURCES OF MARKER DATA

Several forms of genetic markers that are used as marker genotype data 312 (a marker map) are known in the art. A common genetic marker is single nucleotide polymorphisms (SNPs). SNPs occur approximately once every 600 base pairs in the genome. See, for example, Kruglyak and Nickerson, 2001, Nature Genetics 27, 235. The present invention contemplates the use of genotypic databases such as SNP databases as a source of marker genotype data 312. Alleles making up blocks of such SNPs in close physical proximity are often correlated, resulting in reduced genetic variability and defining a limited number of "SNP haplotypes" each of which reflects descent from a single ancient ancestral chromosome. See Fullerton et al., 2000, Am. J. Hum. Genet. 67, 881. Such haplotype structure is useful in selecting appropriate genetic variants for analysis. Patil et al. found that a very dense set of SNPs is required to capture all the common haplotype information. Once common haplotype information is available, it can be used to identify much smaller subsets of SNPs useful for comprehensive whole-genome studies. See Patil et al., 2001, Science 294, 1719-1723.

Other suitable sources of genetic markers include databases that have various types of gene expression data from platform types such as spotted microarray (microarray), high-density oligonucleotide array (HDA), hybridization filter (filter) and serial analysis of gene expression (SAGE) data. Another example of a genetic database that can be used is a DNA methylation database. For details on a representative DNA methylation database, see Grunau et al., 2001, MethDB- a public database for DNA methylation data, *Nucleic Acids Research* 29, 270-274; or the URL: genome.imb-jena.de/public.html.

In one embodiment of the present invention, a set of genetic markers (marker genotype data 312) is derived from any type of genetic database that tracks variations in the genome of an organism of interest. Information that is typically represented in such databases is a collection of loci within the genome of the organism of interest. For each locus, strains for which genetic variation information is available are represented. For each represented strain, variation information is provided. Variation information is any type of genetic variation information. Representative genetic variation information includes, but is not limited to, single nucleotide polymorphisms, restriction fragment length polymorphisms, microsatellite markers, restriction fragment length polymorphisms, and short tandem repeats. Therefore, suitable genotypic databases include, but are not limited to those disclosed in Table 1.

TABLE 1

Exemplary suitable genotypic databases

| Genetic variation type | Uniform resource location |
|---|---|
| SNP | bioinfo.pal.roche.com/usuka_bioinformatics/cgi-bin/msnp/msnp.pl |
| SNP | snp.cshl.org/ |
| SNP | ibc.wustl.edu/SNP/ |
| SNP | www-genome.wi.mit.edu/SNP/mouse/ |
| SNP | ncbi.nlm.nih.gov/SNP/ |
| Microsatellite markers | informatics.jax.org/searches/polymorphism_form.shtml |

TABLE 1-continued

Exemplary suitable genotypic databases

| Genetic variation type | Uniform resource location |
|---|---|
| Restriction fragment length polymorphisms | informatics.jax.org/searches/polymorphism_form.shtml |
| Short tandem repeats | cidr.jhmi.edu/mouse/mmset.html |
| Sequence length polymorphisms | mcbio.med.buffalo.edu/mit.html |
| DNA methylation database | genome.imb-jena.de/public.html |
| Short tandem-repeat polymorphisms | Broman et al., 1998, Comprehensive human genetic maps: Individual and sex-specific variation in recombination, American Journal of Human Genetics 63, 861-869 |
| Microsatellite markers | Kong et al., 2002, A high-resolution recombination map of the human genome, Nature Genetics 31, 241-247 |

In addition, the genetic variations used by the methods of the present invention may involve differences in the expression levels of genes rather than actual identified variations in the composition of the genome of the organism of interest. Therefore, genotypic databases within the scope of the present invention include a wide array of expression profile databases such as the one found at the URL: ncbi.nlm.nih.gov/geo/.

Another form of genetic marker that may be used as marker genotype data 312 (e.g., as a marker map) is restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction endonuclease. Generally, the resulting fragments are separated according to size and hybridized with a probe; single copy probes are preferred. As a result, restriction fragments from homologous chromosomes are revealed. Differences in fragment size among alleles represent an RFLP (see, for example, Helentjaris et al., 1985, Plant Mol. Bio. 5:109-118, and U.S. Pat. No. 5,324,631). Another form of genetic marker that can be used as marker genotype data 312 (e.g., as a marker map) is random amplified polymorphic DNA (RAPD). The phrase "random amplified polymorphic DNA" or "RAPD" refers to the amplification product of the distance between DNA sequences homologous to a single oligonucleotide primer appearing on different sites on opposite strands of DNA. Mutations or rearrangements at or between binding sites will result in polymorphisms as detected by the presence or absence of amplification product (see, for example, Welsh and McClelland, 1990, Nucleic Acids Res. 18:7213-7218; Hu and Quiros, 1991, Plant Cell Rep. 10:505-511). Yet another form of genetic marker map that can be used as marker genotype data 312 is amplified fragment length polymorphisms (AFLP). AFLP technology refers to a process that is designed to generate large numbers of randomly distributed molecular markers (see, for example, European Patent Application No. 0534858 A1). Still another form of marker genotype data 312 that can be used to construct a marker map is "simple sequence repeats" or "SSRs". SSRs are di-, tri- or tetra-nucleotide tandem repeats within a genome. The repeat region can vary in length between genotypes while the DNA flanking the repeat is conserved such that the same primers will work in a plurality of genotypes. A polymorphism between two genotypes represents repeats of different lengths between the two flanking conserved DNA sequences (see, for example, Akagi et al., 1996, Theor. Appl. Genet. 93, 1071-1077; Bligh et al., 1995, Euphytica 86:83-85; Struss et al., 1998, Theor. Appl. Genet. 97, 308-315; Wu et al., 1993, Mol. Gen. Genet. 241, 225-235; and U.S. Pat. No. 5,075,217). SSRs are also known as satellites or microsatellites.

As described above, many genetic markers suitable for use with the present invention are publicly available. Those skilled in the art can also readily prepare suitable markers. For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., 7-21.

5.6. EXEMPLARY NORMALIZATION ROUTINES

A number of different normalization protocols can be used by normalization module 314 (FIG. 3) to normalize cellular constituent data 248. Exemplary normalization protocols are described in this section. Typically, the normalization comprises normalizing the expression level measurement of each gene in a plurality of genes that is expressed by an organism in a population of interest. Many of the normalization protocols described in this section are used to normalize microarray data. It will be appreciated that there are many other suitable normalization protocols that may be used in accordance with the present invention. All such protocols are within the scope of the present invention. Many of the normalization protocols found in this section are found in publicly available software, such as Microarray Explorer (Image Processing Section, Laboratory of Experimental and Computational Biology, National Cancer Institute, Frederick, Md. 21702, USA).

One normalization protocol is Z-score of intensity. In this protocol, raw expression intensities are normalized by the (mean intensity)/(standard deviation) of raw intensities for all spots in a sample. For microarray data, the Z-score of intensity method normalizes each hybridized sample by the mean and standard deviation of the raw intensities for all of the spots in that sample. The mean intensity $mnI_i$ and the standard deviation $sdI_i$ are computed for the raw intensity of control genes. It is useful for standardizing the mean (to 0.0) and the range of data between hybridized samples to about −3.0 to +3.0. When using the Z-score, the Z differences ($Z_{diff}$) are computed rather than ratios. The Z-score intensity (Z-score$_{ij}$) for intensity $I_{ij}$ for probe i (hybridization probe, protein, or other binding entity) and spot j is computed as:

$$Z\text{-score}_{ij}=(I_{ij}-mnI_i)/sdI_i,$$

and $$Z\text{diff}_j(x,y)=Z\text{-score}_{xj}-Z\text{-score}_{yj}$$

where x represents the x channel and y represents the y channel.

Another normalization protocol is the median intensity normalization protocol in which the raw intensities for all spots in each sample are normalized by the median of the raw intensities. For microarray data, the median intensity normalization method normalizes each hybridized sample by the median of the raw intensities of control genes (median$I_i$) for all of the spots in that sample. Thus, upon normalization by the median intensity normalization method, the raw intensity $I_{ij}$ for probe i and spot j, has the value $Im_{ij}$ where, $$Im_{ij}=(I_{ij}/\text{median}I_i).$$

Another normalization protocol is the log median intensity protocol. In this protocol, raw expression intensities are normalized by the log of the median scaled raw intensities of representative spots for all spots in the sample. For microarray data, the log median intensity method normalizes each hybridized sample by the log of median scaled raw intensities of control genes (median$I_i$) for all of the spots in that sample. As used herein, control genes are a set of genes that have reproducible accurately measured expression values. The value 1.0 is added to the intensity value to avoid taking the log(0.0) when intensity has zero value. Upon normalization by the median intensity normalization method, the raw intensity $I_{ij}$ for probe i and spot j, has the value $Im_{ij}$ where, $Im_{ij} = \log(1.0 + (I_{ij}/\text{median}I_i))$.

Yet another normalization protocol is the Z-score standard deviation log of intensity protocol. In this protocol, raw expression intensities are normalized by the mean log intensity (mnLI$_i$) and standard deviation log intensity (sdLI$_i$). For microarray data, the mean log intensity and the standard deviation log intensity is computed for the log of raw intensity of control genes. Then, the Z-score intensity ZlogS$_{ij}$ for probe i and spot j is:

$Z \log S_{ij} = (\log(I_{ij}) - mnLI_i)/sdLI_i$.

Still another normalization protocol is the Z-score mean absolute deviation of log intensity protocol. In this protocol, raw expression intensities are normalized by the Z-score of the log intensity using the equation (log(intensity)-mean logarithm)/standard deviation logarithm. For microarray data, the Z-score mean absolute deviation of log intensity protocol normalizes each bound sample by the mean and mean absolute deviation of the logs of the raw intensities for all of the spots in the sample. The mean log intensity mnLI$_i$ and the mean absolute deviation log intensity madLI$_i$ are computed for the log of raw intensity of control genes. Then, the Z-score intensity ZlogA$_{ij}$ for probe i and spot j is:

$Z \log A_{ij} = (\log(I_{ij}) - mnLI_i)/madLI_i$.

Another normalization protocol is the user normalization gene set protocol. In this protocol, raw expression intensities are normalized by the sum of the genes in a user defined gene set in each sample. This method is useful if a subset of genes has been determined to have relatively constant expression across a set of samples. Yet another normalization protocol is the calibration DNA gene set protocol in which each sample is normalized by the sum of calibration DNA genes. As used herein, calibration DNA genes are genes that produce reproducible expression values that are accurately measured. Such genes tend to have the same expression values on each of several different microarrays. The algorithm is the same as user normalization gene set protocol described above, but the set is predefined as the genes flagged as calibration DNA.

Yet another normalization protocol is the ratio median intensity correction protocol. This protocol is useful in embodiments in which a two-color fluorescence labeling and detection scheme is used. (see Section 5.11.1.5.). In the case where the two fluors in a two-color fluorescence labeling and detection scheme are Cy3 and Cy5, measurements are normalized by multiplying the ratio (Cy3/Cy5) by medianCy5/medianCy3 intensities. If background correction is enabled, measurements are normalized by multiplying the ratio (Cy3/Cy5) by (medianCy5-medianBkgdCy5)/(medianCy3-medianBkgdCy3) where medianBkgd means median background levels.

In some embodiments, intensity background correction is used to normalize measurements. The background intensity data from a spot quantification programs may be used to correct spot intensity. Background may be specified as either a global value or on a per-spot basis. If the array images have low background, then intensity background correction may not be necessary.

5.7. LOGARITHMIC OF THE ODDS SCORES

Denoting the joint probability of inheriting all genotypes P(g), and the joint probability of all observed data x (trait and marker species) conditional on genotypes P(x|g), the likelihood L for a set of data is $L = \Sigma P(g) P(x|g)$ where the summation is over all the possible joint genotypes g (trait and marker) for all pedigree members. What is unknown in this likelihood is the recombination fraction θ, on which P(g) depends.

The recombination fraction θ is the probability that two loci will recombine during meioses. The recombination fraction θ is correlated with the distance between two loci. By definition, the genetic distance is defined to be infinity between the loci on different chromosomes (nonsyntenic loci), and for such unlinked loci, θ=0.5. For linked loci on the same chromosome (syntenic loci), θ<0.5, and the genetic distance is a monotonic function of θ. See, e.g., Ott, 1985, *Analysis of Human Genetic Linkage*, first edition, Baltimore, Md., John Hopkins University Press. The essence of linkage analysis described in Section 5.13, is to estimate the recombination fraction θ and to test whether θ=0.5. When the position of one locus in the genome is known, genetic linkage can be exploited to obtain an estimate of the chromosomal position of a second locus relative to the first locus. In linkage analysis described in Section 5.2, linkage analysis is used to map the unknown location of genes predisposing to various quantitative phenotypes relative to a large number of marker loci in a genetic map. In the ideal situation, where recombinant and nonrecombinant meioses can be counted unambiguously, θ is estimated by the frequency of recombinant meioses in a large sample of meioses. If two loci are linked, then the number of nonrecombinant meioses N is expected to be larger than the number of recombinant meioses R. The recombination fraction between the new locus and each marker can be estimated as:

$$\hat{\theta} = \frac{R}{N+R}$$

The likelihood of interest is:

$L = \Sigma P(g|\theta) P(x|g)$ and inferences are based about a test recombination fraction θ on the likelihood ratio $\Lambda = L(\theta)/L(1/2)$ or, equivalently, its logarithm.

Thus, in a typical clinical genetics study, the likelihood of the trait and a single marker is computed over one or more relevant pedigrees. This likelihood function L(θ) is a function of the recombination fraction θ between the trait (e.g., classical trait or quantitative trait) and the marker locus. The standardized log likelihood $Z(\theta) = \log_{10}[L(\theta)/L(1/2)]$ is referred to as a lod score. Here, "lod" is an abbreviation for "logarithm of the odds." A lod score permits visualization of linkage evidence. As a rule of thumb, in human studies, geneticists provisionally accept linkage if $Z(\hat{\theta}) \geq 3$ at its maximum θ on the interval [0,1/2], where θ̂ represents the maximum θ on the interval. Further, linkage is provisionally rejected at a particular θ if $Z(\hat{\theta}) \leq -2$.

However, for complex traits, other rules have been suggested. See, for example, Lander and Kruglyak, 1995, Nature Genetics 11, p. 241.

Acceptance and rejection are treated asymmetrically because, with 22 pairs of human autosomes, it is unlikely that a random marker even falls on the same chromosome as a trait locus. See Lange, 1997, *Mathematical and Statistical Methods for Genetic Analysis*, Springer-Verlag, New York; Olson, 1999, Tutorial in Biostatistics: Genetic Mapping of Complex Traits, Statistics in Medicine 18, 2961-2981.

When the value of L is large, the null hypothesis of no linkage, L(1/2), to a marker locus of known location can be rejected, and the relative location of the locus corresponding to the quantitative trait can be estimated by θ̂. Therefore, lod scores provide a method to calculate linkage distances as well as to estimate the probability that two genes (and/or QTLs) are linked.

Those of skill in the art will appreciate that lod score computation is species dependent. For example, methods for computing the lod score in mouse is different from those described in this section. However, methods for computing lod scores are known in the art and the methods described in this section are only by way of illustration and not by limitation.

5.8. CLUSTERING TECHNIQUES

The subsections below describe exemplary methods for clustering. Such techniques may be used to cluster QTL vectors in order to form QTL interaction maps. The same techniques can be applied to gene expression vectors in order to form gene expression cluster maps. Further, these techniques may be used to perform unsupervised or supervised classification in accordance with processing step 106 and/or step 108 (FIG. 2). In these techniques, QTL vectors, gene expression vectors, or sets of cellular constituent measurements from different organisms in a population are clustered based on the strength of interaction between the data (e.g., QTL vectors, gene expression vectors, or sets of cellular constituents). More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; Backer, 1995, *Computer-Assisted Reasoning in Cluster Analysis*, Prentice Hall, Upper Saddle River, N.J.; and Duda et al., 2001, *Pattern Classification*, John Wiley & Sons, New York, N.Y.

5.8.1. Hierarchical Clustering Techniques

Hierarchical cluster analysis is a statistical method for finding relatively homogenous clusters of elements based on measured characteristics. Consider a sequence of partitions of n samples into c clusters. The first of these is a partition into n clusters, each cluster containing exactly one sample. The next is a partition into n-1 clusters, the next is a partition into n-2, and so on until the $n^{th}$, in which all the samples form one cluster. Level k in the sequence of partitions occurs when c=n−k+1. Thus, level one corresponds to n clusters and level n corresponds to one cluster. Given any two samples x and x*, at some level they will be grouped together in the same cluster. If the sequence has the property that whenever two samples are in the same cluster at level k they remain together at all higher levels, then the sequence is said to be a hierarchical clustering. Duda et al., 2001, *Pattern Classification*, John Wiley & Sons, New York, 2001: 551.

5.8.1.1. Agglomerative Clustering

In some embodiments, the hierarchical clustering technique used to cluster gene analysis vectors is an agglomerative clustering procedure. Agglomerative (bottom-up clustering) procedures start with n singleton clusters and form a sequence of partitions by successively merging clusters. The major steps in agglomerative clustering are contained in the following procedure, where c is the desired number of final clusters, $D_i$ and $D_j$ are clusters, $x_i$ is a gene analysis vector, and there are n such vectors:

```
1   begin initialize c, ĉ ← n, D_i ← {x_i}, i = 1, ..., n
2       do ĉ ← ĉ − 1
3           find nearest clusters, say, D_i and D_j
4           merge D_i and D_j
5       until c = ĉ
6       return c clusters
7   end
```

In this algorithm, the terminology a←b assigns to variable a the new value b. As described, the procedure terminates when the specified number of clusters has been obtained and returns the clusters as a set of points. A key point in this algorithm is how to measure the distance between two clusters $D_i$ and $D_j$. The method used to define the distance between clusters $D_i$ and $D_j$ defines the type of agglomerative clustering technique used. Representative techniques include the nearest-neighbor algorithm, farthest-neighbor algorithm, the average linkage algorithm, the centroid algorithm, and the sum-of-squares algorithm.

Nearest-neighbor algorithm. The nearest-neighbor algorithm uses the following equation to measure the distances between clusters:

$$d\min(Di, Dj) = \min_{\substack{x \in Di \\ x' \in Dj}} \|x - x'\|.$$

This algorithm is also known as the minimum algorithm. Furthermore, if the algorithm is terminated when the distance between nearest clusters exceeds an arbitrary threshold, it is called the single-linkage algorithm. Consider the case in which the data points are nodes of a graph, with edges forming a path between the nodes in the same subset $D_i$. When dmin( ) is used to measure the distance between subsets, the nearest neighbor nodes determine the nearest subsets. The merging of $D_i$ and $D_j$ corresponds to adding an edge between the nearest pair of nodes in $D_i$ and $D_j$. Because edges linking clusters always go between distinct clusters, the resulting graph never has any closed loops or circuits; in the terminology of graph theory, this procedure generates a tree. If it is allowed to continue until all of the subsets are linked, the result is a spanning tree. A spanning tree is a tree with a path from any node to any other node. Moreover, it can be shown that the sum of the edge lengths of the resulting tree will not exceed the sum of the edge lengths for any other spanning tree for that set of samples. Thus, with the use of dmin( ) as the distance measure, the agglomerative clustering procedure becomes an algorithm for generating a minimal spanning tree. See Duda et al., id, pp. 553-554.

Farthest-neighbor algorithm. The farthest-neighbor algorithm uses the following equation to measure the distances between clusters:

$$d\max(Di, Dj) = \max_{\substack{x \in Di \\ x' \in Dj}} \|x - x'\|.$$

This algorithm is also known as the maximum algorithm. If the clustering is terminated when the distance between the nearest clusters exceeds an arbitrary threshold, it is called the complete-linkage algorithm. The farthest-neighbor algorithm discourages the growth of elongated clusters. Application of this procedure can be thought of as producing a graph in which the edges connect all of the nodes in a cluster. In the terminology of graph theory, every cluster contains a complete subgraph. The distance between two clusters is terminated by the most distant nodes in the two clusters. When the nearest clusters are merged, the graph is changed by adding edges between every pair of nodes in the two clusters.

Average linkage algorithm. Another agglomerative clustering technique is the average linkage algorithm. The average linkage algorithm uses the following equation to measure the distances between clusters:

$$d_{avg}(Di, Dj) = \frac{1}{n_i n_j} \sum_{x \in Di} \sum_{x' \in Dj} \|x - x'\|.$$

Hierarchical cluster analysis begins by making a pair-wise comparison of all gene analysis vectors in a set of such vectors. After evaluating similarities from all pairs of elements in the set, a distance matrix is constructed. In the distance matrix, a pair of vectors with the shortest distance (i.e. most similar values) is selected. Then, when the average linkage algorithm is used, a "node" ("cluster") is constructed by averaging the two vectors. The similarity matrix is updated with the new "node" ("cluster") replacing the two joined elements, and the process is repeated n−1 times until only a single element remains. Consider six elements, A-F having the values:

A{4.9}, B{8.2}, C{3.0}, D{5.2}, E{8.3}, F{2.3}.

In the first partition, using the average linkage algorithm, one matrix (sol. 1) that could be computed is:

(sol. 1) A {4.9}, B-E{8.25}, C{3.0}, D{5.2}, F{2.3}.

Alternatively, the first partition using the average linkage algorithm could yield the matrix:

(sol. 2) A {4.9}, C{3.0}, D{5.2}, E-B{8.25}, F{2.3}.

Assuming that solution 1 was identified in the first partition, the second partition using the average linkage algorithm will yield:

(sol. 1-1) A-D{5.05}, B-E{8.25}, C{3.0}, F{2.3} or (sol. 1-2) B-E{8.25}, C{3.0}, D-A{5.05}, F{2.3}.

Assuming that solution 2 was identified in the first partition, the second partition of the average linkage algorithm will yield:

(sol. 2-1) A-D{5.05}, C{3.0}, E-B{8.25}, F{2.3} or (sol. 2-2) C{3.0}, D-A{5.05}, E-B{8.25}, F{2.3}.

Thus, after just two partitions in the average linkage algorithm, there are already four matrices. See Duda et al., Pattern Classification, John Wiley & Sons, New York, 2001, p. 551.

5.8.1.2. Clustering with Pearson Correlation Coefficients

In one embodiment of the present invention, QTL vectors and/or gene expression vectors are clustered using agglomerative hierarchical clustering with Pearson correlation coefficients. In this form of clustering, similarity is determined using Pearson correlation coefficients between the QTL vectors pairs, gene expression pairs, or sets of cellular constituent measurements. Other metrics that can be used, in addition to the Pearson correlation coefficient, include but are not limited to, a Euclidean distance, a squared Euclidean distance, a Euclidean sum of squares, a Manhattan metric, and a squared Pearson correlation coefficient. Such metrics may be computed using SAS (Statistics Analysis Systems Institute, Cary, N.C.) or S-Plus (Statistical Sciences, Inc., Seattle, Wash.).

5.8.1.3. Divisive Clustering

In some embodiments, the hierarchical clustering technique used to cluster QTL vectors and/or gene expression vectors is a divisive clustering procedure. Divisive (top-down clustering) procedures start with all of the samples in one cluster and form the sequence by successfully splitting clusters. Divisive clustering techniques are classified as either a polythetic or a monthetic method. A polythetic approach divides clusters into arbitrary subsets.

5.8.2. K-Means Clustering

In k-means clustering, sets of QTL vectors, gene expression vectors, or sets of cellular constituent measurements are randomly assigned to K user specified clusters. The centroid of each cluster is computed by averaging the value of the vectors in each cluster. Then, for each i=1, ..., N, the distance between vector $x_i$ and each of the cluster centroids is computed. Each vector $x_i$ is then reassigned to the cluster with the closest centroid. Next, the centroid of each affected cluster is recalculated. The process iterates until no more reassignments are made. See Duda et al., 2001, *Pattern Classification*, John Wiley & Sons, New York, N.Y., pp. 526-528. A related approach is the fuzzy k-means clustering algorithm, which is also known as the fuzzy c-means algorithm. In the fuzzy k-means clustering algorithm, the assumption that every QTL vector, gene expression vector, or set of cellular constituent measurements is in exactly one cluster at any given time is relaxed so that every vector (or set) has some graded or "fuzzy" membership in a cluster. See Duda et al., 2001, *Pattern Classification*, John Wiley & Sons, New York, N.Y., pp. 528-530.

5.8.3. Jarvis-Patrick Clustering

Jarvis-Patrick clustering is a nearest-neighbor non-hierarchical clustering method in which a set of objects is partitioned into clusters on the basis of the number of shared nearest-neighbors. In the standard implementation advocated by Jarvis and Patrick, 1973, *IEEE Trans. Comput.*, C-22: 1025-1034, a preprocessing stage identifies the K nearest-neighbors of each object in the dataset. In the subsequent clustering stage, two objects i and j join the same cluster if (i) i is one of the K nearest-neighbors of j, (ii) j is one of the K nearest-neighbors of i, and (iii) i and j have at least $k_{min}$ of their K nearest-neighbors in common, where K and $k_{min}$ are user-defined parameters. The method has been widely applied to clustering chemical structures on the basis of fragment descriptors and has the advantage of being much less computationally demanding than hierarchical methods, and thus more suitable for large databases. Jarvis-Patrick clustering may be performed using the Jarvis-Patrick Clustering Package 3.0 (Barnard Chemical Information, Ltd., Sheffield, United Kingdom).

5.8.4. Neural Networks

A neural network has a layered structure that includes a layer of input units (and the bias) connected by a layer of weights to a layer of output units. In multilayer neural networks, there are input units, hidden units, and output units. In fact, any function from input to output can be implemented as a three-layer network. In such networks, the weights are set based on training patterns and the desired output. One method for supervised training of multilayer neural networks is back-propagation. Back-propagation allows for the calculation of an effective error for each hidden unit, and thus derivation of a learning rule for the input-to-hidden weights of the neural network.

The basic approach to the use of neural networks is to start with an untrained network, present a training pattern to the input layer, and pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum-likelihood estimation of the weight values in the model defined by the network topology. In batch training, all patterns are presented to the network before learning takes place. Typically, in batch training, several passes are made through the training data. In online training, each pattern is presented once and only once to the net.

5.8.5. Self-Organizing Maps

A self-organizing map is a neural-network that is based on a divisive clustering approach. The aim is to assign genes to a series of partitions on the basis of the similarity of their expression vectors to reference vectors that are defined for each partition. Consider the case in which there are two microarrays from two different experiments. It is possible to build up a two-dimensional construct where every spot corresponds to the expression levels of any given gene in the two experiments. A two-dimensional grid is built, resulting in several partitions of the two-dimensional construct. Next, a gene is randomly picked and the identify of the reference vector (node) closest to the gene picked is determined based on a distance matrix. The reference vector is then adjusted so that it is more similar to the vector of the assigned gene. That means the reference vector is moved one distance unit on the x axis and y-axis and becomes closer to the assigned gene. The other nodes are all adjusted to the assigned gene, but only are moved one half or one-fourth distance unit. This cycle is repeated hundreds of thousands times to converge the reference vector to fixed value and where the grid is stable. At that time, every reference vector is the center of a group of genes. Finally, the genes are mapped to the relevant partitions depending on the reference vector to which they are most similar.

5.9. MULTIVARIATE STATISTICAL MODELS

Using the methods of the present invention, candidate pathway groups are identified from the analysis of QTL interaction map data and gene expression cluster maps. Each candidate pathway group includes a number of genes. The methods of the present invention are advantageous because they filter the potentially thousands of genes in the genome of the population of interest into a few candidate pathway groups using clustering techniques. In a typical case, a candidate pathway group represents a group of genes that tightly cluster in a gene expression cluster map. The genes in a candidate pathway group can also cluster tightly in a QTL interaction map. The QTL interaction map serves as a complementary approach to defining the genes in a candidate pathway group. For example, consider the case in which genes A, B, and C cluster tightly in a gene expression cluster map. Furthermore, genes A, B, C and D cluster tightly in the corresponding QTL interaction map. In this example, analysis of the gene expression cluster map alone suggest that genes A, B, C form a candidate pathway group. However, analysis of both the QTL interaction map and the gene expression cluster map suggests that the candidate pathway group comprises genes A, B, C, and D.

Once candidate pathway groups have been identified, multivariate statistical techniques can be used to determine whether each of the genes in the candidate pathway group affect a particular trait, such as a complex disease trait. The form of multivariate statistical analysis used in some embodiments of the present invention is dependent upon on the type of genotype and/or pedigree data that is available.

Typically, more pedigree data is available in cases where the population to be studied is plants or animals. In such instances, the multivariate statistical models such as those of Jiang and Zeng, 1995, *Nature Genetics* 140, pp. 1111-1127, as well as the techniques implemented in QTL Cartographer (Basten and Zeng, 1994, Zmap-a QTL cartographer, *Proceedings of the 5th World Congress on Genetics Applied to Livestock Production: Computing Strategies and Software* 22, Smith et al. eds., pp. 65-66, The Organizing Committee, 5th World Congress on Genetics Applied to Livestock Production, Guelph, Ontario, Canada; Basten et al., 2001, *QTL Cartographer, Version* 1.15, Department of Statistics, North Carolina State University, Raleigh, N.C. In addition, marker regression (joint mapping, marker-difference regression, MDR), interval mapping with marked cofactors, and composite interval mapping can be used. See, for example, Lynch & Walsh, 1998, *Genetics and Analysis of Quantitative Traits*, Sinauer Associates, Inc., Sunderland, Mass.

Jiang and Zeng have developed a multiple-trait extension to composite interval mapping (CIM). See, for example, Jiang and Zeng, 1995, Genetics 140, p. 1111. CIM refers to the general approach of adding marker cofactors to an otherwise standard interval analysis (e.g., QTL detection using linear models or via maximum likelihood). CIM handles multiple QTLs by incorporating mutlilocus marker information from organisms by modifying standard interval mapping to include additional markers as cofactors for analysis. See, for example, Jansen, 1993, Genetics 135, p. 205; Zeng, 1994, Genetics 136, p. 1457. The multiple-trait extension to CIM developed by Jiang and Zeng provides a framework for testing the candidate pathway groups that are constructed using the methods of the present invention in cases where the genes in these candidate pathway groups link to the same genetic region. The methods of Jiang and Zeng allow for the determination as to whether expression values (for the genes in the candidate pathway group) linking to the same region are controlled by a single gene pleiotropy) or by two closely linked genes. If the methods of Jiang and Zeng suggest that multiple genes are actually controlled by closely linked loci (closely linked genes), then there is not support that the genes liking to the same region are in the same pathway. Moreover, the components (hierarchy) of a pathway can be deduced by testing subsets of the pathway group to see which genes have an underlying pleiotropic relationship with respect to other genes. Further, the definition of the candidate pathway group can be refined by eliminating specific genes in the candidate pathway group that do not have a pleiotropic relationship with other genes in the candidate pathway group. The idea is to determine which of the genes linking to given region, have other genes linking to their physical location, indicating the order for hierarchy and control.

Presently, the practical limits are that no more than ten genes can be handled at once using multivariate methods such as the Jiang and Zeng methods. Theoretically, the number of genes is limited by the amount of data available to fit the model, but the particular limitation is that the optimization techniques are not effective for greater than 10 dimensions. However, in some embodiments, more than 10 genes can be handled at once by implementing dimensionality reductions techniques (like principal components).

For human genotype and pedigree data, methods described in Allison, 1998, Multiple Phenotype Modeling in Gene-Mapping Studies of Quantitative Traits: Power Advantages, *Am J Hum. Genetics* 63, pp. 1190-1201, are used, including, but not limited to, those of Amos et al., 1990, *Am J Hum. Genetics* 47, pp. 247-254.

In some embodiments, gene expression data is collected for multiple tissue types. In such instances, multivariate analysis can be used to determine the true nature of a complex disease. Multivariate techniques used in this embodiment of the invention are described, in part, in Williams et al., 1999, *Am J Hum Genet* 65(4): 1134-47; Amos et al., 1990, *Am J Hum Genet* 47(2): 247-54, and Jiang and Zeng, 1995, *Nature Genetics* 140:1111-1127.

Asthma provides one example of a complex disease that can be studied using expression data from multiple tissue types. Asthma is expected to, in part, be influenced by immune system response not only in lungs but also in blood. By measuring expression of genes in the lung and in blood, the following model could be used to dissect the shared genetic effect in a model system, e.g. an F2 mouse cross:

$$y_{j_1} = \alpha_1 + b_1 x_j + d_1 z_j + e_{j_1}$$
$$y_{j_2} = \alpha_2 + b_2 x_j + d_2 z_j + e_{j_2}$$
$$\vdots$$
$$y_{jm} = \alpha_m + b_m x_j + d_m z_j + e_{jm}$$

where, for individual j and a putative QTL:

$y_{j1}, \ldots, y_{jm}$ consists of asthma relevant phenotypes, expression data for gene expression in the lung and expression data for gene expression in blood;

$x_j$ is the number of QTL alleles from a specific parental line;

$z_j$ is 1 if the individual is heterozygous for the QTL and 0 otherwise;

$\alpha_i$ represents the mean for phenotype i;

$b_i$ and $d_i$ represent the additive and dominance effects of the QTL on phenotype i; and $e_{ji}$ is the residual error for individual j and phenotype i.

It is typically assumed that the residuals are uncorrelated between individuals, and the correlation between residuals within an individual are modeled as $Cov(e_{jk}, e_{jl}) = \rho_{kl} \sigma_k \sigma_l$. Assuming a multivariate normal distribution for the residuals, likelihood analysis can be used to test for joint linkage of a QTL to the trait vector and to test for pleiotropic effects versus close linkage. With such information, it would be possible to detect a QTL that influences susceptibility to asthma through causing changes in gene expression for a set of genes expressed in blood and for a set of, potentially overlapping, genes expressed in lung. Such multivariate analyses in accordance with the present invention, combined with high quality phenotypic data that includes expression data across multiple tissues, allows for improved detection of those genes truly influencing susceptibility to complex diseases.

5.10. ANALYTIC KIT IMPLEMENTATION

In a preferred embodiment, the methods of this invention can be implemented by use of kits. Such kits contain microarrays, such as those described in Subsections below. The microarrays contained in these kits comprise a solid phase, e.g. a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more databases described above and in FIG. 2 and/or FIG. 4, encoded on computer readable medium, and/or an access authorization to use the databases described above from a remote networked computer.

In another preferred embodiment, a kit of the invention further contains software capable of being loaded into the memory of a computer system such as the one described supra, and illustrated in FIG. 2 and/or FIG. 4. The software contained in the kit of this invention, is essentially identical to the software described above in conjunction with FIG. 2 and/or FIG. 4.

Alternative kits for implementing the analytic methods of this invention will be apparent to one of skill in the art and are intended to be comprehended within the accompanying claims.

5.11. TRANSCRIPTIONAL STATE MEASUREMENTS

This section provides some exemplary methods for measuring the expression level of genes, which are one type of cellular constituent. One of skill in the art will appreciate that this invention is not limited to the following specific methods for measuring the expression level of cellular constituents (e.g., genes) in each organism in a plurality of organisms.

5.11.1. Transcript Assay Using Microarrays

The techniques described in this section are particularly useful for the determination of the expression state or the transcriptional state of a cell or cell type or any other cell sample by monitoring expression profiles. These techniques include the provision of polynucleotide probe arrays that may be used to provide simultaneous determination of the expression levels of a plurality of genes. These technique further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance rations. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (i.e., the sequence) of each probe can be determined from its position on the array (i.e., on the support or surface). In some embodiments, the arrays are ordered arrays.

Preferably, the density of probes on a microarray or a set of microarrays is about 100 different (i.e., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$ or at least 2,000 probes per 1 cm$^2$. In a particularly preferred embodiment, the microarray is a high density array, preferably having a density of at least about 2,500 different probes per 1 cm$^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence may also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene or exon. However, if desired, the profiling arrays may contain at least 2, 5, 10, 100, or 1000 or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the exon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such instances, an exon is represented by a single binding site on the profiling arrays. In some preferred cases, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 200 bases (see, e.g., Lewin, Genes V, Oxford University Press, Oxford, 1994). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of Saccharomyces cerevisiae has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, Science 274: 546-567). In contrast, the human genome is estimated to contain approximately 30,000 to 130,000 genes (see Crollius et al., 2000, Nature Genetics 25:235-238; Ewing et al., 2000, Nature Genetics 25:232-234). Genome sequences for other organisms, including but not limited to Drosophila, C. elegans, plants, e.g., rice and Arabidopsis, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, *Science* 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g. hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.11.1.1. Preparing Probes for Microarrays

As noted above, the "probe" to which a particular polynucleotide molecule, such an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Inis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g. using N-phosphonate or phosphoramidite chemistries (Froehler et al, 1986, *Nucleic Acid Res*. 14:5399-5407; McBride et at, 1983, *Tetrahedron Lett*. 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Eghohn et al., 1993, *Nature* 363:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.11.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res*. 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al, 1994, *Proc. Natl. Acad. Sci. U.S.A.* 91:5022-5026; Lockhart et al, 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res*. 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic*

*DNA Arrays in Genetic Engineering*, Vol. 20, J. K. Setlow, Ed., Plenum Press, New York at pages 111-123).

5.11.1.3. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g. U.S. Pat. Nos. 5,891,636, 5,716,785; 5,545,522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, 15N and $^{125}$I. Fluorescent molecules suitable for the present invention include, but are not limited to, fluorescein and its derivatives, rhodamine and its derivatives, texas red, 5'carboxy-fluorescein ("FMA"), 2',7'-dimethoxy-4',5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.11.1.4. Hybridization to Microarrays

As described supra, nucleic acid hybridization and wash conditions are chosen so that the polynucleotide molecules to be analyzed by the invention (referred to herein as the target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.11.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, *Science* 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of differences of an order of about 1.5 fold to about 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.11.2. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.12. TRANSLATIONAL STATE MEASUREMENTS

In various embodiments of the present invention, aspects of the biological state other than the transcriptional state, such as the translational state, the activity state, or mixed aspects can be measured. Thus, in such embodiments, cellular constituent data 44 (FIG. 1) may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in the this and following sections.

Measurement of the translational state may be performed according to several methods. For example, whole genome monitoring of protein (i.e., the "proteome," Goffeau et al., supra) can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274: 536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.13. MEASURING OTHER ASPECTS OF THE BIOLOGICAL STATE

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from the organism 46 (FIG. 1) of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes may be recorded as often as several times each hour.

During one incubation, more than 5,000 phenotypes can be tested. See, for example, Bochner et al., 2001, Genome Research 11, 1246-55.

In some embodiments of the present invention, the cellular constituents that are measured (gene expression data 44) are metabolites. Metabolites include, but are not limited to, amino acids, metals, soluble sugars, sugar phosphates, and complex carbohydrates. Such metabolites may be measured, for example, at the whole-cell level using methods such as pyrolysis mass spectrometry (Irwin, 1982, *Analytical Pyrolysis: A Comprehensive Guide, Marcel Dekker, New York; Meuzelaar et al., 1982, Pyrolysis Mass Spectrometry of Recent and Fossil Biomaterials*, Elsevier, Amsterdam), fourier-transform infrared spectrometry (Griffiths and de Haseth, 1986, *Fourier transform infrared spectrometry*, John Wiley, New York; Helm et al., 1991, J. Gen. Microbiol. 137, 69-79; Naumann et al., 1991, Nature 351, 81-82; Naumann et al., 1991, In: *Modern techniques for rapid microbiological analysis*, 43-96, Nelson, W. H., ed., VCH Publishers, New York), Raman spectrometry, gas chromatography-mass spectroscopy (GC-MS) (Fiehn et al., 2000, Nature Biotechnology 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods may be combined with established chemometric methods that make use of artificial neural networks and genetic programming in order to discriminate between closely related samples.

5.14. EXEMPLARY DISEASES

Examples of complex diseases in humans include asthma, ataxia telangiectasia (Jaspers and Bootsma, 1982, *Proc. Natl. Acad. Sci. U.S.A.* 79: 2641), bipolar disorder, common cancers, common late-onset Alzheimer's disease, diabetes, heart disease, hereditary early-onset Alzheimer's disease (George-Hyslop et al., 1990, *Nature* 347: 194), hereditary nonpolyposis colon cancer, hypertension, infection, maturity-onset diabetes of the young (Barbosa et al., 1976, *Diabete Metab.* 2: 160), mellitus, migraine, nonalcoholic fatty liver (NAFL) (Younossi, et al., 2002, Hepatology 35, 746-752), nonalcoholic steatohepatitis (NASH) (James & Day, 1998, *J. Hepatol.* 29: 495-501), non-insulin-dependent diabetes mellitus, obesity, polycystic kidney disease (Reeders et al., 1987, *Human Genetics* 76: 348), psoriases, schizophrenia, steatohepatitis and xeroderma pigmentosum (De Weerd-Kastelein, *Nat. New Biol.* 238: 80). Genetic heterogeneity hampers genetic mapping, because a chromosomal region may cosegregate with a disease in some families but not in others.

5.15. SUPERVISED CLASSIFICATION METHODS

A variety of methods may be used to perform supervised classification in accordance with processing step 106 (FIG. 1), including linear regression methods such as multiple linear regression (MLR), partial least squares regression (PLS) and principal components regression (PCR). Such methods are described, for example in (Brereton, 1992, Multivariate Pattern Recognition in Chemometrics, Elsievier, Amsterdam; Brown et al., 1992, Chemometrics. Anal. Chem. 64, 22R-49R; Martens and Næs, 1989, *Multivariate Calibration*, John Wiley & Sons, New York; and Meloun et al., 1992, *Chemometrics for Analytical Chemistry* Vol 1, PC-aided Statistical Data Analysis, Ellis Horwood, Chichester, UK (1992). Furthermore, non-linear versions of these techniques may be used in processing step 106 (FIG. 1). See, for example, Frank et al., 1990, *Chemom. Intell. Lab. Sys.* 8: 109-119; Höskuldsson, 1992, *J. Chemom.* 6: 307-334; Kvalheim et al., 1985, *Anal. Chem.* 57: 2858-2864; Wold, 1992, *Chemom. Intell. Lab. Sys.* 14: 71-84; and Wythoff, 1993, *Chemom. Intell. Lab. Sys.* 20: 129-148. A related approach that may be used in processing step 106 (FIG. 1) is artificial neural networks (ANNs).

The goal of supervised learning is to find a model or mapping that will correctly associate the inputs with the targets. Thus, the basic idea in these supervised learning techniques is that there are minimally four data sets to be studied. The "training data" consist of (i) a matrix of s rows and n columns in which s is the number of objects and n the number of variables and (ii) a second matrix, again consisting of s rows and typically 1 or two columns, in which the columns represent the variable(s) whose value(s) it is desired to know and which for the training set have actually been determined by some existing, "benchmark" method. This variable is paired with the patterns in the same row in (i). The "test data" also consist of two matrices, (iii) and (iv), corresponding to those in (i) and (ii) above, but the test set contains different objects. As the name suggests, this second pair is used to test the accuracy of the system. Alternatively, they may be used to cross-validate the model. That is to say, after construction of the model using the training set (i, ii) the test data (iii) (these may be new spectra) are then "passed" through the calibration model so as to obtained the model's prediction of results. These may then be compared with the known, expected responses (iv). As in all other data analysis techniques, these supervised learning methods are not immune from sensitivity to badly chosen initial data See, for example, Zupan and Gasteiger, 1993, *Neural Networks for Chemists: An Introduction*, VCH Verlagsgesellschaft, Weinheim. Therefore, the exemplars for the training set must be carefully chosen.

5.16. EXEMPLARY METHOD FOR IDENTIFYING A CLASS PREDICTOR

This section describes a method for finding a class predictor 262 (FIG. 2) for a given complex trait of interest, in accordance with one embodiment of the invention. The class predictor is used to facilitate the division of a population P into a plurality of subpopulations using a supervised classification scheme. Examples of the techniques disclosed in this section may be found in the U.S. provisional application Ser. No. 60/380,710 entitled "Diagnosis and Prognosis of Breast Cancer Patients," filed May 14, 2002. As used in this section, a "marker" means an entire gene, or an EST derived from that gene, the expression or level of which changes between certain conditions. Where the expression of the gene correlates with a certain condition, the gene is a marker for that condition.

The techniques described in this section uses sets of markers for the identification of a class predictor 262 for breast cancer. One of skill in the art will appreciate that the techniques can be used to find a class predictor 262 for other complex traits. Generally, the class predictor 262 is identified by determining which of 25,000 human markers has expression patterns that correlate with the conditions or indications (e.g., phenotype) associated with the complex trait.

In one embodiment, the technique for identifying class predictors 262 is as follows. After extraction and labeling of target polynucleotides, the expression of all markers in a sample X is compared to the expression of all markers in a standard or control. In one embodiment, the standard or control comprises target polynucleotide molecules derived from a sample from a normal individual (e.g., an individual not afflicted with breast cancer). In a preferred embodiment, the standard or control is a pool of target polynucleotide molecules. The pool may derived from collected samples from a number of normal individuals. In a preferred embodiment, the pool comprises samples taken from a number of individuals having sporadic-type tumors. In another preferred embodiment, the pool comprises an artificially-generated population of nucleic acids designed to approximate the level of nucleic acid derived from each marker found in a pool of marker-derived nucleic acids derived from tumor samples. In yet another embodiment, the pool is derived from normal or breast cancer cell lines or cell line samples.

The comparison may be accomplished by any means known in the art. For example, expression levels of various markers may be assessed by separation of target polynucleotide molecules (e.g., RNA or cDNA) derived from the markers in agarose or polyacrylamide gels, followed by hybridization with marker-specific oligonucleotide probes. Alternatively, the comparison may be accomplished by the labeling of target polynucleotide molecules followed by separation on a sequencing gel. Polynucleotide samples are placed on the gel such that patient and control or standard polynucleotides are in adjacent lanes. Comparison of expression levels is accomplished visually or by means of densitometer. In a preferred embodiment, the expression of all markers is assessed simultaneously by hybridization to a microarray. In each approach, markers meeting certain criteria are identified as associated with breast cancer.

A marker is selected based upon significant difference of expression in a sample as compared to a standard or control condition. Selection may be made based upon either significant up- or down regulation of the marker in the patient sample. Selection may also be made by calculation of the statistical significance (i.e., the p-value) of the correlation between the expression of the marker and the condition or indication. Preferably, both selection criteria are used. Thus, in one embodiment of the present invention, markers associated with breast cancer are selected where the markers show both more than two-fold change (increase or decrease) in expression as compared to a standard, and the p-value for the correlation between the existence of breast cancer and the change in marker expression is no more than 0.01 (i.e., is statistically significant).

The expression of the identified breast cancer-related markers is then used to identify markers that can differentiate tumors into clinical types. In a specific embodiment using a number of tumor samples, markers are identified by calculation of correlation coefficients between the clinical category or clinical parameter(s) and the linear, logarithmic or any transform of the expression ratio across all samples for each individual gene. Specifically, the correlation coefficient is calculated as:

$$\rho = (\vec{c} \cdot \vec{r})/(\|\vec{c}\| \cdot \|\vec{r}\|)$$

where $\vec{c}$ represents the clinical parameters or categories and $\vec{r}$ represents the linear, logarithmic or any transform of the ratio of expression between sample and control. Markers for which the coefficient of correlation exceeds a cutoff are identified as breast cancer-related markers specific for a particular clinical type. Such a cutoff or threshold corresponds to a certain significance of discriminating genes obtained from Monte Carlo simulations. The threshold depends upon the number of samples used; the threshold can be calculated as $3 \times 1/\sqrt{n-3}$, where $\sqrt{n-3}$ is the distribution width and n=the number of samples. In a specific embodiment, markers are chosen if the correlation coefficient is greater than about 0.3 or less than about −0.3.

Next, the significance of the correlation is calculated. This significance may be calculated by any statistical means by which such significance is calculated. In a specific example, a set of correlation data is generated using a Monte-Carlo technique to randomize the association between the expression difference of a particular marker and the clinical category. The frequency distribution of markers satisfying the criteria through calculation of correlation coefficients is compared to the number of markers satisfying the criteria in the data generated through the Monte-Carlo technique. The frequency distribution of markers satisfying the criteria in the Monte-Carlo runs is used to determine whether the number of markers selected by correlation with clinical data is significant.

Once a marker set is identified, the markers may be rank-ordered in order of significance of discrimination. One means of rank ordering is by the amplitude of correlation between the change in gene expression of the marker and the specific condition being discriminated. Another preferred means is to use a statistical metric. In a specific embodiment, the metric is a Fisher-like statistic:

$$t = \frac{(\langle x_1 \rangle - \langle x_2 \rangle)}{\sqrt{[\sigma_1^2(n_1 - 1) + \sigma_2^2(n_2 - 1)]/(n_1 + n_2 - 1)/(1/n_1 + 1/n_2)}}$$

In this equation, $\langle x_i \rangle$ is the error-weighted average of the log ratio of transcript expression measurements within a first diagnostic group (e.g., ER(−)), $\langle x_2 \rangle$ is the error-weighted average of log ratio within a second, related diagnostic group (e.g., ER(+)), $\sigma_1$ is the variance of the log ratio within the ER(−) group and $n_1$ is the number of samples for which valid measurements of log ratios are available. $\sigma_2$ is the variance of log ratio within the second diagnostic group (e.g., ER(+)), and $n_2$ is the number of samples for which valid measurements of log ratios are available. The t-value represents the variance-compensated difference between two means.

The rank-ordered marker set may be used to optimize the number of markers in the set used for discrimination. This is accomplished generally in a "leave one out" method as follows. In a first run, a subset, for example 5, of the markers from the top of the ranked list is used to generate a template, where out of X samples, X−1 are used to generate the template, and the status of the remaining sample is predicted. This process is repeated for every sample until every one of the X samples is predicted once. In a second run, additional markers, for example 5, are added, so that a template is now generated from 10 markers, and the outcome of the remaining sample is predicted. This process is repeated until the entire set of markers is used to generate the template. For each of the runs, type 1 error (false negative) and type 2 errors (false positive) are counted; the optimal number of markers is that number where the type 1 error rate, or type 2 error rate, or preferably the total of type 1 and type 2 error rate is lowest.

For prognostic markers, validation of the marker set may be accomplished by an additional statistic, a survival model. This statistic generates the probability of tumor distant metastases as a function of time since initial diagnosis. A number of models may be used, including Weibull, normal, log-normal, log logistic, log-exponential, or log-Rayleigh (Chapter 12 "Life Testing", S-PLUS 2000 GUIDE TO STATISTICS, Vol. 2, p. 368, 2000). For the "normal" model, the probability of distant metastases P at time t is calculated as:

$P = \alpha \times \exp(-t^2/\tau^2)$ where $\alpha$ is fixed and equal to 1, and $\tau$ is a parameter to be fitted and measures the "expected lifetime".

It will be apparent to those skilled in the art that the above methods, in particular the statistical methods, described above, are not limited to the identification of markers associated with breast cancer, but may be used to identify a class predictor (e.g. a set of marker genes) for any phenotype, including a complex trait. The phenotype can, for example, be the presence or absence of a disease such as cancer, or the presence or absence of any identifying clinical condition associated with that cancer. In the disease context, the phenotype may be a prognosis such as a survival time, probability of distant metastases of a disease condition, or likelihood of a particular response to a therapeutic or prophylactic regimen. The phenotype need not be cancer, or a disease; the phenotype may be a nominal characteristic associated with a healthy individual.

5.17. USE OF GENE EXPRESSION PATTERNS TO ENHANCE THE GENETIC SIGNATURE AT A PARTICULAR LOCUS

Complex traits potentially involve many genes (i.e., are polygenic) and complicated environmental interactions. Experimental designs, such as those adopted for a heterosis study, attempt to minimize the extent of genetic heterogeneity by restricting attention to two inbred lines of plants. In addition, environmental variation is reduced in such study designs by growing the plants under controlled, similar conditions. However, in controlled experiments, certain phenotypes are still complex from the standpoint of genetic heterogeneity. Not only is this evidenced in field data traits, but it is seen in gene expression traits as well, where several of the genes have multiple QTL, indicating the expression of the gene is under the control of more than one gene.

Figure 7:
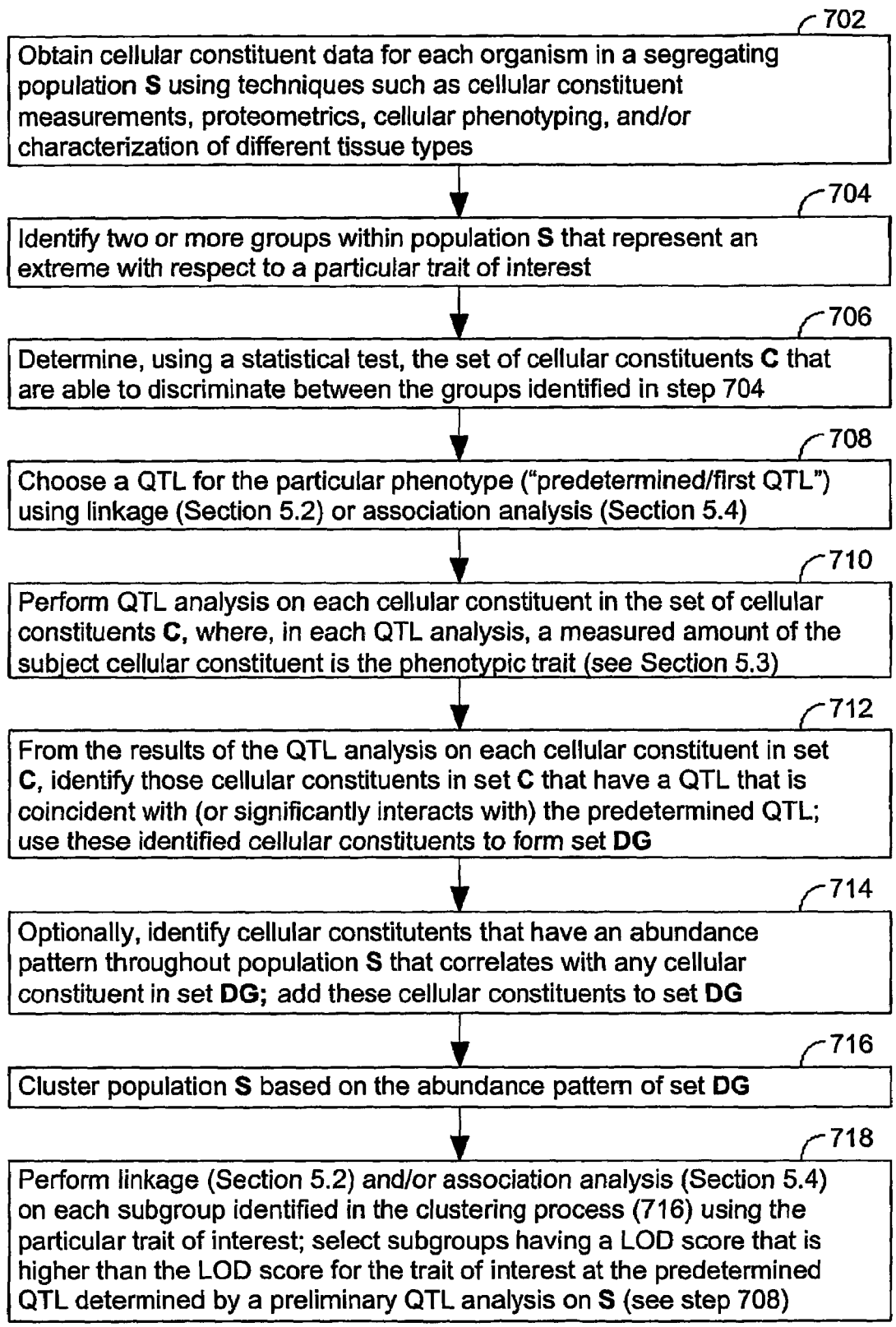
FIG. 7 illustrates processing steps for subdividing a disease population P into n subgroups and then subjecting one or more of the n subgroups to quantitative genetic analysis in accordance with another embodiment of the present invention.

To tease apart pleiotropic pathway effects, the use of cellular constituent abundance patterns (e.g. gene expression patterns) associated with a primary trait of interest (e.g., heterosis, cholesterol levels, body weight, etc.) as a means of subdividing a given population into more homogenous subgroups is described using FIG. 7 as a reference. It will be appreciated that FIG. 7 is just one example of how genetics and cellular constituent abundance data can be combined to subdivide a population in order to perform quantitative genetic analysis on subpopulations.

The exemplary process begins with step 702, in which cellular constituent data is collected for each organism in a segregating population S using techniques such as cellular constituent measurement, proteometrics, cellular phenotyping, or characterization of different phenotypes. See, for example, Sections 5.11, 5.12, and 5.13, supra. Segregating populations S can range from $F_2$ plants or mice derived from two inbred lines, to large human pedigrees. In step 702, the independent extremes of the population with respect to a particular quantifiable phenotype (e.g., complex trait) are identified. In one embodiment, an organism is within the group that represents an independent extreme with respect to a particular phenotype (e.g., complex trait) when the magnitude of the particular phenotype exhibited by the organism is greater than the magnitude of the particular phenotype exhibited by at least seventy percent, seventy-five percent, eighty percent, eighty-five percent, or ninety percent of the organisms in a population under study (e.g., plurality of organisms S). Once the independent extremes have been identified, all cellular constituents (e.g. transcripts of genes) with abundances that are able to discriminate between extreme phenotypic groups (independent extremes) with reasonable accuracy are identified (step 706). In some embodiments, there are two independent extreme phenotypic groups. In other embodiments, there are more than two independent extreme phenotypic groups. The set of cellular constituents that can discriminate between independent extreme phenotypic groups is referred to in this embodiment as the set of cellular constituents C. Many types of statistical analysis, such as a t-test, can be used to identify cellular constituents in the set G.

In step 708, QTL for the primary trait of interest are identified using standard linkage analysis, such as that described in Section 5.2, supra. That is, the pedigree data for population S, the phenotypic data for the trait of interest, and the genetic marker map for the species under study is used to identify QTL that are linked to the trait under study. In embodiments where pedigree information is not available, an association analysis can be used to identify loci that are linked to the trait of interest. Association analyses are described in Section 5.4, supra. FIG. 7 has been simplified to the case in which a single QTL (or loci in the case of association analysis) is identified in step 708. It will be appreciated that, in fact, any number of QTL and/or loci can be identified in processing step 708 and that processing steps 710 through 718 can be repeated for each QTL and/or loci, or group of such QTLs and/or loci, identified in processing step 708. Further, the single QTL (or loci) identified in processing step 710 of FIG. 708 is designated the "predetermined QTL" to distinguish the QTL (or loci) from all other QTLs (or loci) identified in subsequent processing steps.

In step 710, quantitative genetic analysis is performed using each cellular constituent in the set of cellular constituents C. In each analysis, the expression level of a cellular constituent selected from among the set of cellular constituents C serves as a phenotypic trait. Each analysis is performed in accordance with the quantitative genetic analysis described in Section 5.3, supra. Each quantitative genetic analysis that uses the abundance data (e.g., expression data) for a given cellular constituent C in population S identifies the QTL (loci) associated with the cellular constituent. In step 712, this data is used to select which cellular constituents will remain in discriminating set G. In one embodiment, only those cellular constituents C that have a QTL (loci) that is linked with the predetermined QTL or that, in fact, overlap with the predetermined QTL are allowed to stay in set G. Cellular constituents that do not have a QTL that is linked with the predetermined QTL and do not have a QTL that overlaps the predetermined QTL are discarded. For clarity, the refined set of cellular constituents is termed "DG" in step 712.

Step 714 represents an optional step that can be used to increase the number of cellular constituents in set DG. In this optional step, the abundance patterns of several cellular constituents in the organism under study, across the population under study, is compared to the abundance pattern of any cellular constituent in set DG. Cellular constituents having abundance patterns that are highly correlated with the abundance pattern of a cellular constituent in set DG across population S are added to set DG. More information on how this type of correlation may be computed is found in PCT International Publication WO 00/39338 dated Jul. 6, 2000.

In step 716, population S is clustered based on the abundance pattern of cellular constituent set C. Therefore, those organisms in population S that have similar abundance patterns across cellular constituent set C will form clusters. The type of clustering used may be any of the various clustering methods described in Sections 5.1 and/or 5.8, supra. The clustering results in a set of clusters (e.g. subgroups) of population S having similar abundance patterns across cellular constituent set C.

In step 718, linkage analysis (Section 5.2) or association analysis (Section 5.4) on the trait of interest is performed using the different subgroups identified in step 716. Those subgroups leading to a significantly increased lod score, or other form of metric used to quantify linkage, for the trait of interest at the QTL of interest are analyzed further. In particular, such subgroups are subjected to a series of quantitative genetic analyses. In each quantitative genetic analysis in the series, the expression level of a cellular constituent selected from among the cellular constituents in set DG is used as a quantitative trait. Each such quantitative genetic analysis is performed in accordance with Section 5.3, supra. The end result of this analysis is the identification of QTL that are linked with the cellular constituents in set DG. Analysis of these genes using, for example, multivariate techniques such as those described in Section 5.9, supra, leads to the identification of genes that affect the complex trait under study. Analysis of the cellular constituents in set DG is of particular interest because these cellular constituents were able to discriminate between phenotypic extremes for the complex trait under study. Therefore, QTL that are linked to such cellular constituents may lead to genes that affect the complex trait.

5.18. GENERALIZED APPROACH

This section describes additional methods for subdividing a population exhibiting a complex disease into subpopulations.

Step 1202. In step 1202 (FIG. 12A), a trait is selected for study in a species. In some embodiments, the trait is a complex trait. The species can be a plant, animal, human, or bacterial. In some embodiments, the species is human, cat, dog, mouse, rat, monkey, pigs, *Drosophila*, or corn. In some embodiments, a plurality of organisms representing the species are studied. The number of organism in the species can be any number. In some embodiments, the plurality of organisms studied is between 5 and 100, between 50 and 200, between 100 and 500, or more than 500.

In some embodiments, a portion of the organisms under study are subjected to a perturbation that affects the trait. The perturbation can be environmental or genetic. Examples of environmental perturbations include, but are not limited to, exposure of an organism to a test compound, an allergen, pain, hot or cold temperatures. Additional examples of environmental perturbations include diet (e.g. a high fat diet or low fat diet), sleep deprivation, isolation, and quantifying a natural environmental influences (e.g., smoking, diet, exercise). Examples of genetic perturbations include, but are not limited to, the use of gene knockouts, introduction of an inhibitor of a predetermined gene or gene product, N-Ethyl-N-nitrosourea (ENU) mutagenesis, siRNA knockdown of a gene, or quantifying a trait exhibited by a plurality of organisms of a species.

The perturbation optionally used in step 1202 is selected because of some relationship between the perturbation and the trait. For example, the perturbation could be the siRNA knockdown of a gene that is thought to influence the trait under study. Examples of traits that can be studied in the systems and methods of the present invention are disclosed in Section 5.14, above.

Step 1204. In step 1204 (FIG. 12A), the levels of cellular constituents are measured from the plurality of organisms 246 in order to derive gene expression/cellular constituent data 244. The identity of the tissue from which such measurements are made will depend on what is known about the trait under study. In some embodiments, cellular constituent measurements are made from several different tissues.

Generally, the plurality of organisms 246 exhibit a genetic variance with respect to the trait. In some embodiments, the trait is quantifiable. For example, in instances where the trait is a disease, the trait can be quantified in a binary form (e.g., "1" if the organism has contracted the disease and "0" if the organism has not contracted the disease). In some embodiments, the trait can be quantified as a spectrum of values and the plurality of organisms 246 will represent several different values in such a spectrum. In some embodiments, the plurality of organisms 246 comprise an untreated (e.g. unexposed, wild type, etc.) population and a treated population (e.g., exposed, genetically altered, etc.). In some embodiments, for example, the untreated population is not subjected to a perturbation whereas the treated population is subjected to a perturbation. In some embodiments, the tissue that is measured in step 1204 is blood, white adipose tissue, or some other tissue that is easily obtained from organisms 246.

In varying embodiments, the levels of between 5 cellular constituents and 100 cellular constituents, between 50 cellular constituents and 100 cellular constituents, between 300 and 1000 cellular constituents, between 800 and 5000 cellular constituents, between 4000 and 15,000 cellular constituents, between 10,000 and 40,000 cellular constituents, or more than 40,000 cellular constituents are measured.

In one embodiment, gene expression/cellular constituent data 244 comprises the processed microarray images for each individual (organism) 246 in a population under study. In some embodiments, such data comprises, for each individual 246, intensity information 250 for each gene/cellular constituent 248 represented on the microarray. In some embodiments, cellular constituent data 244 is, in fact, protein expression levels for various proteins in a particular tissue in organisms 246 under study.

In one aspect of the present invention, cellular constituent levels are determined in step 1204 by measuring an amount of the cellular constituent in a predetermined tissue of the organism. As used herein, the term "cellular constituent" comprises individual genes, proteins, mRNA, metabolites and/or any other cellular components that can affect the trait under study. The level of a cellular constituent can be measured in a wide variety of methods. Cellular constituent levels, for example, can be amounts or concentrations in tissues of the organisms, their activities, their states of modification (e.g., phosphorylation), or other measurements relevant to the trait under study.

In one embodiment, step 1204 comprises measuring the transcriptional state of cellular constituents 248 in tissues of organisms 246. The transcriptional state includes the identities and abundances of the constituent RNA species, especially mRNAs, in the tissue. In this case, the cellular constituents are RNA, cRNA, cDNA, or the like. The transcriptional state of the cellular constituents can be measured by techniques of hybridization to arrays of nucleic acid or nucleic acid mimic probes, or by other gene expression technologies. Transcript arrays are discussed in Section 5.11, above.

In another embodiment, step 1204 comprises measuring the translational state of cellular constituents 248. In this case, the cellular constituents are proteins. The translational state includes the identities and abundances of the proteins in the organisms 246. In one embodiment, whole genome monitoring of protein (i.e., the "proteome," Goffeau et al., 1996, Science 274, p. 546) can be carried out by constructing a microarray in which binding sites comprise immobilized, preferably monoclonal, antibodies specific to a plurality of protein species found in one or more tissues of the organisms under study. Preferably, antibodies are present for a substantial fraction of the encoded proteins. Methods for making monoclonal antibodies are well known. See, for example, Harlow and Lane, 1998, *Antibodies: A Laboratory Manual*, Cold Spring Harbor, N.Y. In one embodiment, monoclonal antibodies are raised against synthetic peptide fragments designed based on genomic sequences. With such an antibody array, proteins from the organism are contacted with the array and their binding is assayed with assays known in the art. In some embodiments, antibody arrays for high-throughput screening of antibody-antigen interactions are used. See, for example, Wildt et al., Nature Biotechnology 18, p. 989.

Alternatively, large scale quantitative protein expression analysis can be performed using radioactive (e.g., Gygi et al., 1999, Mol. Cell. Biol 19, p. 1720) and/or stable isotope ($^{15}N$) metabolic labeling (e.g., Oda et al. Proc. Natl. Acad. Sci. USA 96, p. 6591) followed by two-dimensional (2D) gel separation and quantitative analysis of separated proteins by scintillation counting or mass spectrometry. Two-dimensional gel electrophoresis is well-known in the art and typically involves focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, Proc Nat'l Acad. Sci. USA 93, p. 1440; Sagliocco et al., 1996, Yeast 12, p. 1519; Lander 1996, Science 274, p. 536; and Naaby-Haansen et al., 2001, TRENDS in Pharmacological Science 22, p. 376. Electropherograms can be analyzed by numerous techniques, including mass spectrometric techniques, western blotting and immunoblot analysis using polyclonal and monoclonal antibodies, and internal and N-terminal microsequencing. See, for example, Gygi, et al., 1999, Nature Biotechnology 17, p. 994. In some embodiments, fluorescence two-dimensional difference gel electrophoresis (DIGE) is used. See, for example, Beaumont et al., Life Science News 7, 2001. In some embodiments, quantities of proteins in organisms 246 are determined using isotope-coded affinity tags (ICATs) followed by tandem mass spectrometry. See, for example, Gygi et al., 1999, Nature Biotech 17, p. 994. Using such techniques, it is possible to identify a substantial fraction of the proteins expressed in one or more predetermined tissues in organisms 246.

In other embodiments, step 1204 comprises measuring the activity or post-translational modifications of the cellular constituents in the plurality of organisms 246. See for example, Zhu and Snyder, Curr. Opin. Chem. Biol 5, p. 40; Martzen et al., 1999, Science 286, p. 1153; Zhu et al., 2000, Nature Genet. 26, p. 283; and Caveman, 2000, J. Cell. Sci. 113, p. 3543. In some embodiments, measurement of the activity of the cellular constituents is facilitated using techniques such as protein microarrays. See, for example, MacBeath and Schreiber, 2000, Science 289, p. 1760; and Zhu et al., 2001, Science 293, p. 2101. In some embodiments, post-translation modifications or other aspects of the state of cellular constituents are analyzed using mass spectrometry. See, for example, Aebersold and Goodlett, 2001, Chem Rev 101, p. 269; Petricoin III, 2002, The Lancet 359, p. 572.

In some embodiments, the proteome of organisms 246 under study is analyzed in step 1204. The analysis of the proteome (e.g., the quantification of all proteins and the determination of their post-translational modifications) typically involves the use of high-throughput protein analysis methods such as microarray technology. See, for example, Templin et al., 2002, TRENDS in Biotechnology 20, p. 160; Albala and Humphrey-Smith, 1999, Curr. Opin. Mol. Ther. 1, p. 680; Cahill, 2000, *Proteomics: A Trends Guide*, p. 47-51; Emili and Cagney, 2000, Nat. Biotechnol., 18, p. 393; and Mitchell, Nature Biotechnology 20, p. 225.

In still other embodiments, "mixed" aspects of the amounts cellular constituents are measured in step 1204. In one example, the amounts or concentrations of one set of cellular constituents in the organisms 246 under study are combined with measurements of the activities of certain other cellular constituents in such organisms.

In some embodiments, different allelic forms of a cellular constituent in a given organism are detected and measured in step 1204. For example, in a diploid organism, there are two copies of any given gene, one descending from the "father" and the other from the "mother." In some instances, it is possible that each copy of the given gene is expressed at different levels. This is of significant interest since this type of allelic differential expression could associate with the trait under study, particularly in instances where the trait under study is complex.

Step 1206. Once gene expression/cellular constituent data 244 has been obtained, the data is transformed (FIG. 12A, step 1206) into expression statistics. In some embodiments, cellular constituent data 244 (FIG. 2) comprises transcriptional data, translational data, activity data, and/or metabolite abundances for a plurality of cellular constituents. In one embodiment, the plurality of cellular constituents comprises at least five cellular constituents. In another embodiment, the plurality of cellular constituents comprises at least one hundred cellular constituents, at least one thousand cellular constituents, at least twenty thousand cellular constituents, or more than thirty thousand cellular constituents.

The expression statistics commonly used as quantitative traits in the analyses in one embodiment of the present invention include, but are not limited to, the mean log ratio, log intensity, and background-corrected intensity derived from transcriptional data. In other embodiments, other types of expression statistics are used as quantitative traits.

In one embodiment, this transformation (FIG. 12A, step 1206) is performed using normalization module (not shown). In such embodiments, the expression level of each of a plurality of genes in each organism under study is normalized. Any normalization routine can be used by the normalization module. Representative normalization routines include, but are not limited to, Z-score of intensity, median intensity, log median intensity, Z-score standard deviation log of intensity, Z-score mean absolute deviation of log intensity calibration DNA gene set, user normalization gene set, ratio median intensity correction, and intensity background correction. Furthermore, combinations of normalization routines can be run. Exemplary normalization routines in accordance with the present invention are disclosed in more detail in Section 5.6, above.

Step 1250. In the preceding steps, a trait is identified, cellular constituent level data is measured, and the cellular constituent data is transformed into expression statistics. In step 1250 (FIG. 12A), one or more phenotypes are measured for all or a portion of the organisms 246 in the population under study. FIG. 13 summarizes the data that is measured as a result of steps 1202-1206 and 1250. For each organism 246 in the population under study there are at least two classes of data collected. The first class of data collected is phenotypic information 1301. Phenotypic information 1301 can be anything related to the trait under study. For example, phenotypic information 1301 can be a binary event, such as whether or not a particular organism exhibits the phenotype (+/−). The phenotypic information can be some quantity, such as the results of an obesity measurement for the respective organism 246. As illustrated in FIG. 13, there can be more than one phenotypic measurement made per organism 246.

Figure 12A:
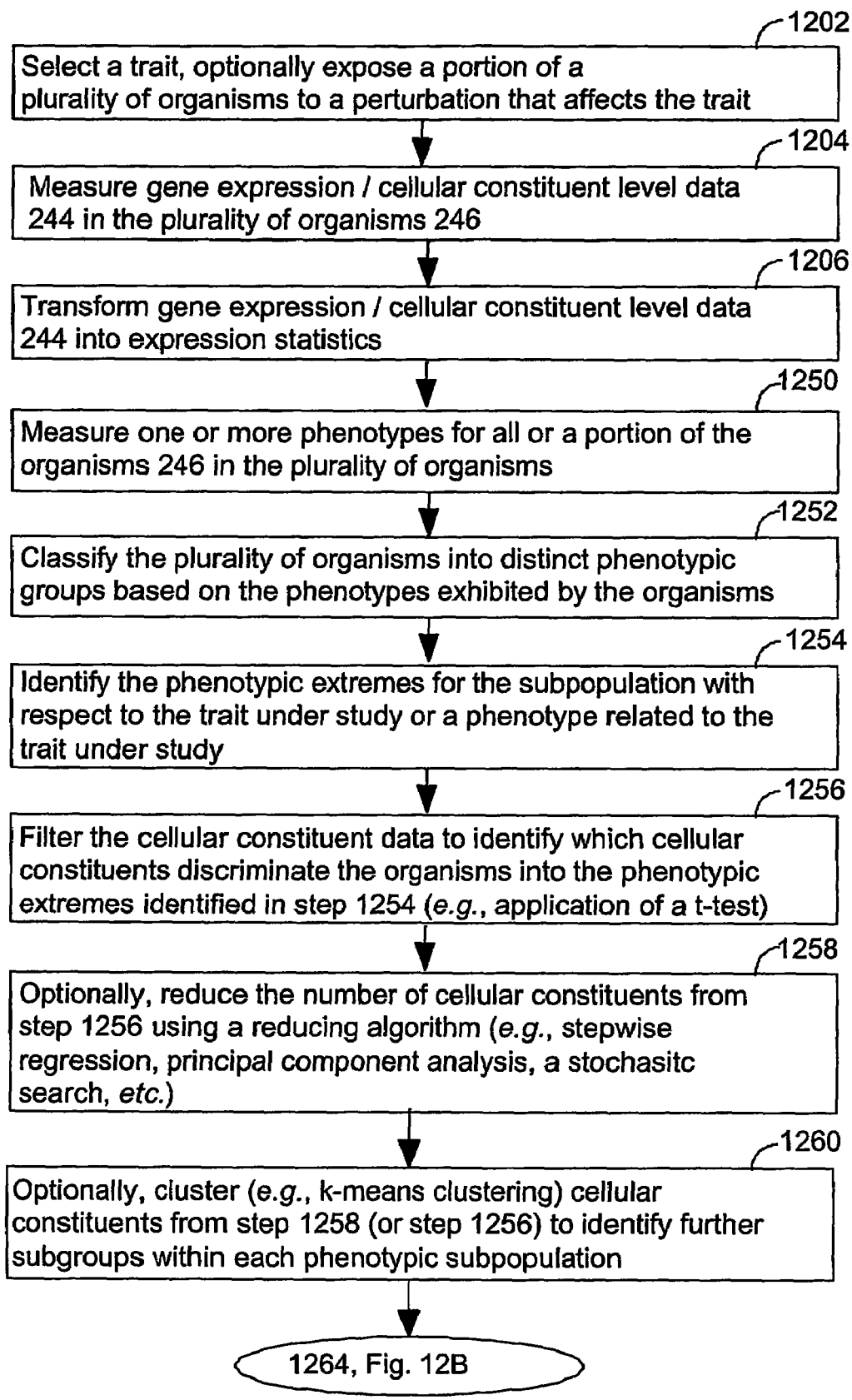
FIG. 12 illustrates processing steps for subdividing a disease population P into n subgroups and then subjecting one or more of the n subgroups to quantitative genetic analysis in accordance with a preferred embodiment of the present invention.

The second class of data collected for each organism 246 in the population under study is cellular constituent levels 250 (e.g., amounts, abundances) for a plurality of cellular constituents (steps 1204-1206, FIG. 12A). Although not illustrated in FIG. 13, there can be several sets of cellular constituent measurements for each organism. Each of these sets could represent cellular constituent measurements measured in the respective organism 246 after the organism has been subjected to a perturbation that affects the trait under study. Representative perturbations include, but are not limited to, exposing the organism 246 to an amount of a compound. Further, each set of cellular constituents for a respective organism 246 could represent measurements taken from a different tissue in the organisms. For example, one set of cellular constituent measurements could be from a blood sample taken from the respective organism while another set of cellular constituent measurements could be from fat tissue from the respective organism.

Figure 14:
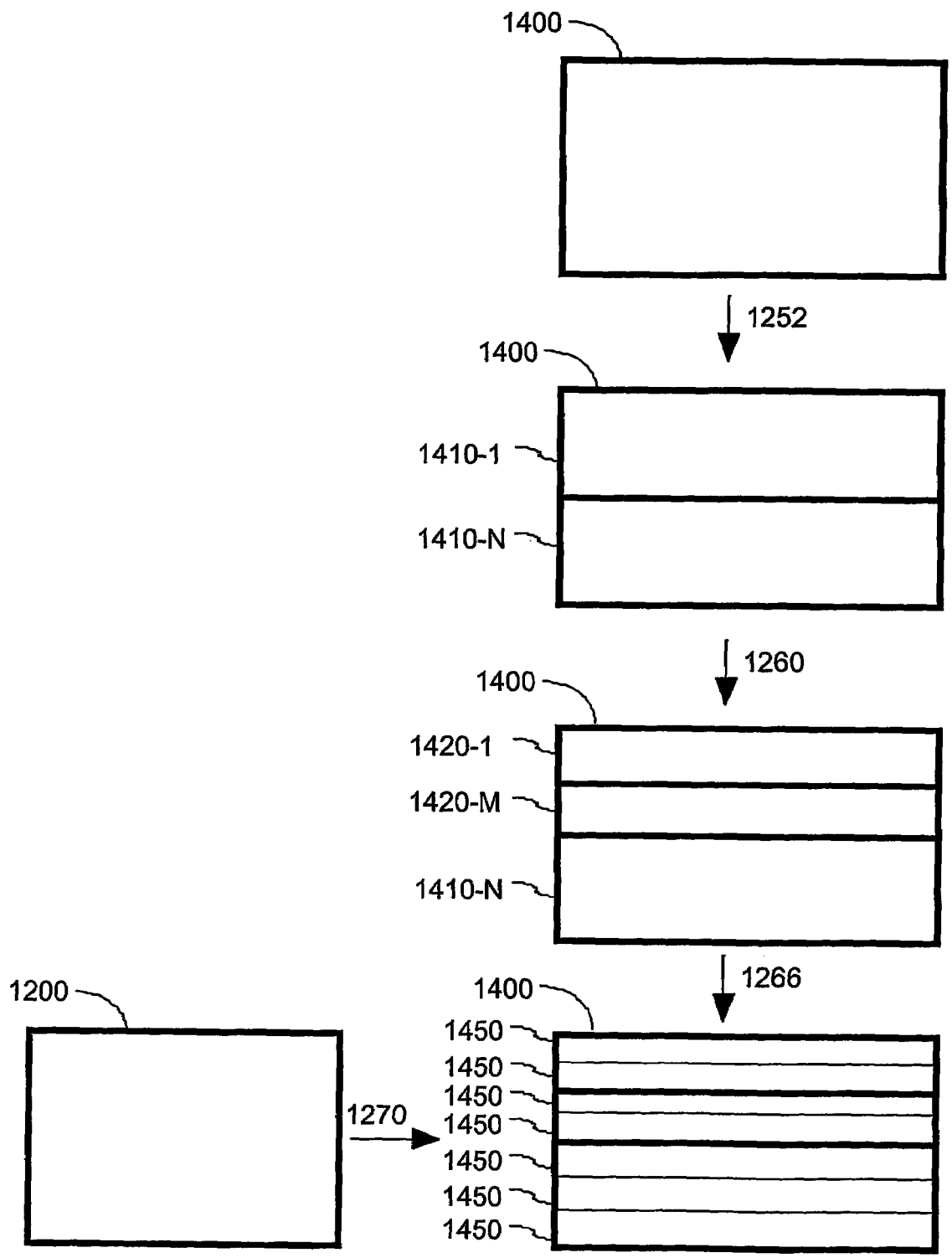
FIG. 14 illustrates the classification of a trait of interests into subtraits in accordance with one embodiment of the present invention.

Step 1252. In step 1252 (FIG. 12A), the phenotypic data 1301 (FIG. 13) collected in step 1250 is used to divide the population into phenotypic groups 1410 (FIG. 14). The method by which step 1252 is accomplished is dependent upon the type of phenotypic data measured in step 1250. For example, in the case where the only phenotypic data is whether or not the organism 246 exhibits a particular trait, step 1252 is straightforward. Those organisms 246 that exhibit the trait are placed in a first group and those organisms 246 that do not exhibit the trait are placed in a second group. A slightly more complex example is where amounts 1301 represent gradations of a quantified trait exhibited by each organism 246. For example, in the case where the trait is obesity, each amount 1301 can correspond to an obesity index (e.g., body mass index, etc.) for the respective organism 246. In this second example, organisms 246 can be binned into phenotypic groups 1410 as a function of the obesity index.

In yet another example in accordance with the invention, a plurality of phenotypic measurements (e.g., 2, 3, 4, 5, 8, 10, 20 or more, between 10 and 20, 20 or more, etc.) can be obtained from a given organism 246. In such embodiments, each phenotypic measurement 1301 for a respective organism 246 can be treated as elements of a phenotypic vector corresponding to the respective organism 246. These phenotypic vectors can then be clustered using, for example, any of the clustering techniques disclosed in Section 5.8 in order to derive phenotypic groups 1410. To illustrate, in one example, the organisms 246 are human and measurements 1301 are derived from a standard 12-lead electrocardiogram graph (ECG). The standard 12-lead ECG is a representation of the heart's electrical activity recorded from electrodes on the body surface. The ECG provides a wealth of phenotypic data including, but not limited to, heart rate, heart rhythm, conduction, wave form description, and ECG interpretation (typically a binary event, e.g., normal, abnormal). Each of these different phenotypes (heart rate, heart rhythm) can be quantified as elements in a phenotypic vector. Further, some elements of the phenotypic vector (e.g., ECG interpretation) can be given more weight during clustering. For instance, the ECG measurements can be augmented by additional phenotypes such as blood cholesterol level, blood triglyceride level, sex, or age in order to derive a phenotypic vector for each respective organism 246. Once suitable phenotypic vectors are constructed, they can be clustered using any of the clustering algorithms in Section 5.8 in order to identify phenotypic groups 1410.

In some embodiments, step 1252 is an iterative process in which various phenotypic vectors are constructed and clustered until a form of phenotypic vector that produces clear, distinct groups is identified. Of particular interest are those phenotypic vectors that are capable of producing phenotypic groups 1410 that are uniquely characterized by certain phenotypes (e.g. an abnormal ECG/high cholesterol subgroup, a normal ECG/low cholesterol subgroup).

Using the example presented above, phenotypic vectors that can be iteratively tested include a vector that has ECG data only, one that has blood measurements only, one that is a combination of the ECG data and blood measurements, one that has only select ECG data, one that has weighted ECG data, and so forth. Furthermore, optimal phenotypic vectors can be identified using search techniques such as stochastic search techniques (e.g., simulated annealing, genetic algorithm). See, for example, Duda et al., 2001, *Pattern Recognition*, second edition, John Wiley & Sons, New York.

Step 1254. In step 1254, the phenotypic extremes within the population are identified. Such phenotypic extremes can be referred to as a set of extreme organisms. For example, in one case, the trait of interest is obesity. In step 1254, very obese and very skinny organisms 246 can be selected as the phenotypic extremes in this step. In various embodiments of the present invention, a phenotypic extreme is defined as the top or lowest $40^{th}$, $30^{th}$, $20^{th}$, or $10^{th}$ percentile of the population with respect to a given phenotype exhibited by the population. In some embodiments, there are more than 5, more than 10, more than 20, more than 100, more than 1000, between 2 and 100, between 25 and 500, less than 100, or less than 1000 organisms in the set of extreme organisms that are referred to as phenotypic extremes.

Step 1256. In step 1256, a plurality of cellular constituents (levels 250, FIG. 13) for the species represented by the set of extreme organisms are filtered. Only levels 250 measured for phenotypically extreme organisms 246 selected in step 1254 (the set of extreme organisms) are used in this filtering. To illustrate using FIG. 13, consider the case in which organism 246-1 and organism 246-N represent phenotypic extremes with respect to some phenotype whereas organism 246-2 does not. Then, in this instance, levels 250 measured for organism 246-6 and 246-N will be considered in the filtering whereas levels 250 measured for organism 246-2 will not be considered in the filtering.

In some embodiments, cellular constituent levels 250 (measured in phenotypically extreme organisms) for a given cellular constituent 248 are subjected to a t-test (or some other test such as a multivariate test to determine whether the given cellular constituent 248 can discriminate between the phenotypic groups 1410 (FIG. 14) that were identified in step 1252, above. A cellular constituent 248 will discriminate between phenotypic groups when the cellular constituent is found at characteristically different levels in each of the phenotypic groups 1410. For example, in the case where there are two phenotypic groups 1410, a cellular constituent will discriminate between the two groups 1410 when levels 250 of the cellular constituent (measured in phenotypically extreme organisms) are found at a first level in the first phenotypic group and are found at a second level in the second phenotypic group, where the first and second level are distinctly different.

In preferred embodiments, each cellular constituent is subjected to a t-test without consideration of the other cellular constituents in the organism. However, in other embodiments, groups of cellular constituents are compared in a multivariate analysis in step 1256 in order to identify those cellular constituents that discriminate between phenotypic groups 1410.

Step 1258. Typically, there will be a large number of cellular constituents expressed in phenotypically extreme organisms that appear to differentiate between the phenotypic groups identified in step 1252. In some instances, this number of cellular constituents 248 can exceed the number of organisms 246 available for study. For instance, in some embodiments, 25,000 genes or more are considered in previous steps. Thus, there may be hundreds if not thousands of genes that discriminate the phenotypically extreme groups. In some instances, these discriminating cellular constituents are analyzed in subsequent steps with statistical models that involve many statistical parameters that cannot accommodate more cellular constituents than organisms as this leads to an overdetermined system. In such instances, it is desirable to reduce the number of cellular constituents using a reducing algorithm. However, in other instances, other forms of statistical analysis are used that do not require reduction in the number of cellular constituents under consideration.

The reducing algorithms that are optionally used in step 1258 use the p-value or other form of metric computed for each cellular constituent in step 1256 as a basis for reducing the dimensionality of the cellular constituent set identified in step 1256. A few exemplary reducing algorithms will be discussed. However, those of skill in the art will appreciate that many reducing algorithms are known in the art and all such algorithms can be used in step 1258.

One reducing algorithm is stepwise regression. The basic procedure in stepwise regression involves (1) identifying an initial model (e.g., an initial set of cellular constituents), (2) iteratively "stepping," that is, repeatedly altering the model at the previous step by adding or removing a predictor variable (cellular constituent) in accordance with the "stepping criteria," and (3) terminating the search when stepping is no longer possible given the stepping criteria, or when a specified maximum number of steps has been reached. Forward stepwise regression starts with no model terms (e.g., no cellular constituents). At each step the regression adds the most statistically significant term until there are none left. Backward stepwise regression starts with all the terms in the model and removes the least significant cellular constituents until all the remaining cellular constituents are statistically significant. It is also possible to start with a subset of all the cellular constituents and then add significant cellular constituents or remove insignificant cellular constituents until a desired dimensionality reduction is achieved.

Another reducing algorithm that can be used in step 1258 is all-possible-subset regression. In fact, all-possible-subset regression can be used in conjunction with stepwise regression. The stepwise regression search approach presumes there is a single "best" subset of cellular constituents and seeks to identify it. In the all-possible-subset regression approach, the range of subset sizes that could be considered to be useful is made. Only the "best" of all possible subsets within this range of subset sizes are then considered. Several different criteria can be used for ordering subsets in terms of "goodness", such as multiple R-square, adjusted R-square, and Mallow's Cp statistics. When all-possible-subset regression is used in conjunction with stepwise methods, the subset multiple R-square statistic allows direct comparisons of the "best" subsets identified using each approach.

Another approach to reducing higher dimensional space into lower dimensional space in accordance with step 1258 (FIG. 12A) of the present invention is the use of linear combinations of cellular constituents. In effect, linear methods project high-dimensional data onto a lower dimensional space. Two approaches for accomplishing this projection include Principal Component Analysis (PCA) and Multiple-Discriminant Analysis (MDA). PCA seeks a projection that best represents the data in a least-squares sense whereas MDA seeks a projection that bests separates the data in a least-squares sense. See, for example, Duda et al., 2001, *Pattern Classification*, Chapters 3 and 10.

The ultimate goal of step 1258 is to identify a classifier derived from the set of cellular constituents identified in step 256 or a subset of the cellular constituents identified in step 1256 that satisfactorily classifies organisms 246 into the phenotypic groups 1410 identified in step 1252. In some embodiments of the present invention, stochastic search methods such as simulated annealing can be used to identify such a classifier or subset. In the simulated annealing approach, for example, each cellular constituent under consideration can be assigned a weight in a function that assesses the aggregate ability of the set of cellular constituents identified in step 1256 to discriminate the organisms 246 into the phenotypic classes identified in step 1252. During the simulated annealing algorithm these weights can be adjusted. In fact, some cellular constituents can be assigned a zero weight and, therefore, be effectively eliminated during the anneal thereby effectively reducing the number of cellular constituents used in subsequent steps. Other stochastic methods that can be used in step 1258 include, but are not limited to, genetic algorithms. See, for example, the stochastic methods in Chapter 7 of Duda et al., 2001, Pattern Classification, second edition, John Wiley & Sons, New York.

Step 1260. In some embodiments, the cellular constituents identified in steps 1256 and/or 1258 are clustered in order to further identify subgroups within each phenotypic subpopulation. To perform such clustering, an expression vector is created for each cellular constituent under consideration. To create an expression vector for a respective cellular constituent, the levels 1301 measured for the respective cellular constituent in each of the phenotypically extreme organisms is used as an element in the vector. For example, consider the case in which an expression vector for cellular constituent 248-1 is to be constructed from organisms 246-1, 246-2, and 246-3. Levels 250-1-1, 250-2-1, and 250-3-1 would serve as the three elements of the expression vector that represents cellular constituent 248-1. Each of the expression vectors are then clustered using, for example, any of the clustering techniques described in Section 5.8, above. In one embodiment, k-means clustering (Section 5.8.2) is used.

Figure 11:
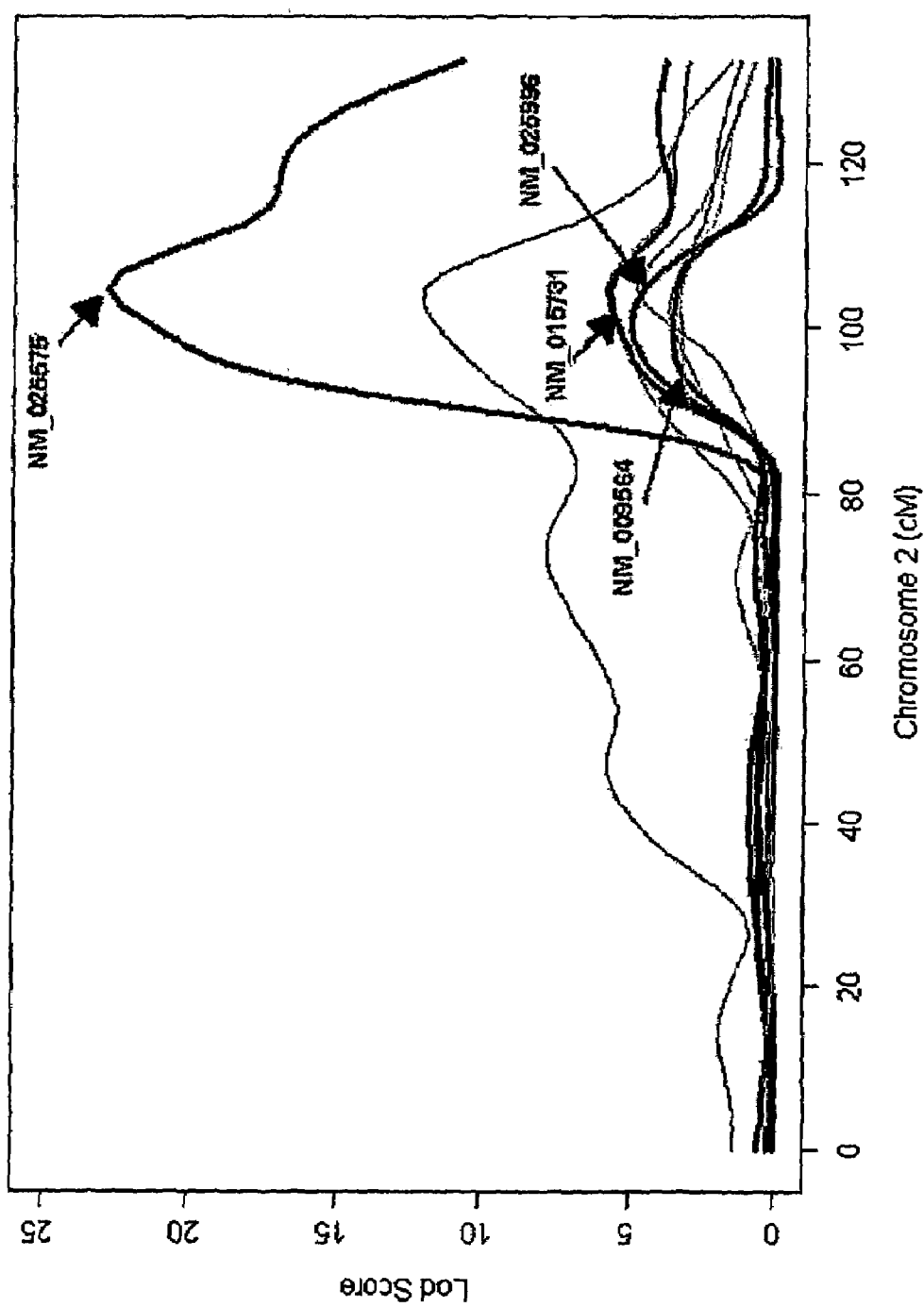
FIG. 11 illustrates the lod scores for various obesity related genes.

A benefit of step 1260 is that the clustering that is performed in the step refines the trait under study into groups 1220 (FIG. 12) that are not distinguishable using gross observable phenotypic data (other than cellular constituent levels) such as amounts 1101 (FIG. 11). As such, optional step 260 provides a way to refine the definition of the clinical trait under study by focusing on those cellular constituents that actually give rise to the clinical trait or well reflect the varied biochemical response to that trait. However, the refinement provided in step 260 can be considered incomplete because it is based on only a select portion of the general population under study, those organisms that represent the phenotypic extremes. For this reason, pattern classification techniques are used in subsequent steps of the instant method to build a robust classifier that is capable of classifying the general population into subgroups in a manner that does not rely upon phenotypic levels 1101 (FIG. 11).

Step 1264. In step 1264, the set of cellular constituents identified as discriminators between phenotypic extremes that were identified in previous steps (or principal components derived from such cellular constituents) are used to build a classifier. This set of cellular constituents actually refines the definition of the clinical phenotype under study. A number of pattern classification techniques can be used to accomplish this task, including, but not limited to, Bayesian decision theory, maximum-likelihood estimation, linear discriminant functions, multilayer neural networks, and supervised as well as unsupervised learning.

In one embodiment in accordance with step 1264, the set of cellular constituents that discriminate the phenotypically extreme organisms into phenotypic groups is used to train a neural network using, for example, a back-propagation algorithm. In this embodiment, the neural network serves as a classifier. First, the neural network is trained with a probability distribution derived from the set of cellular constituents that discriminate the phenotypically extreme organisms into phenotypic groups. For example, in some embodiments, the probability distribution comprises each cellular constituent t-value or other statistic computed in step 1256. Once the neural network has been trained, it is used to classify the general population into phenotypic groups. In some embodiments the neural network that is trained is a multilayer neural network. In other embodiments, a projection pursuit regression, a generalized additive model, or a multivariate adaptive regression spline is used. See, for example, any of the techniques disclosed in Chapter 6 of Duda et al, 2001, *Pattern Classification*, second edition, John Wiley & Sons, Inc., New York.

In another embodiment in accordance with step 1264, Bayesian decision theory can be used to build a classifier. Bayesian decision theory plays a role when there is some a priori information about the things to be classified. Here, a probability distribution derived from the set of cellular constituents that discriminate the phenotypically extreme organisms into phenotypic groups serves as the a priori information. For example, in some embodiments, this probability distribution comprises each cellular constituent p-value or other statistic computed in step 1256. For more information on Bayesian decision theory, see for, example, any of the techniques disclosed in Chapters 2 and 3 of Duda et al., 2001, *Pattern Classification*, second edition, John Wiley & Sons, Inc., New York.

In still another embodiment in accordance with step 1264, linear discriminate analysis (functions), linear programming algorithms, or support vector machines are used to create a classifier that is capable of classifying the general population of organisms 246 into phenotypic groups 1410. This classification is based on the cellular constituent data 250 for the cellular constituents 248 that refined the definition of the clinical phenotype (i.e. the cellular constituents selected in steps 1256, 1258, and/or 1260). For more information on this class of pattern classification functions, see for, example, any of the techniques disclosed in Chapter 5 of Duda et al., 2001, *Pattern Classification*, second edition, John Wiley & Sons, Inc., New York.

Step 1266. In step 1266, the classifier derived in step 1264 is used to classify all or a substantial portion (e.g., more than 30%, more than 50%, more than 75%) of the population under study. Essentially, the classifier bins the remaining population (the portions of the population that do not include the phenotypic extremes) without taking their phenotypic (e.g., phenotype amounts 1301, FIG. 13) into consideration. The process of using the classifier to classify the general population produces phenotypic classifications (phenotypic subgroups) 1450 (FIG. 14). Phenotypic subgroups 1450 can be considered a refinement of the trait under study and subsequently used in analysis of the underlying biochemical process that differentiate the trait under study into groups 1250 using the techniques disclosed below.

Figure 12B:
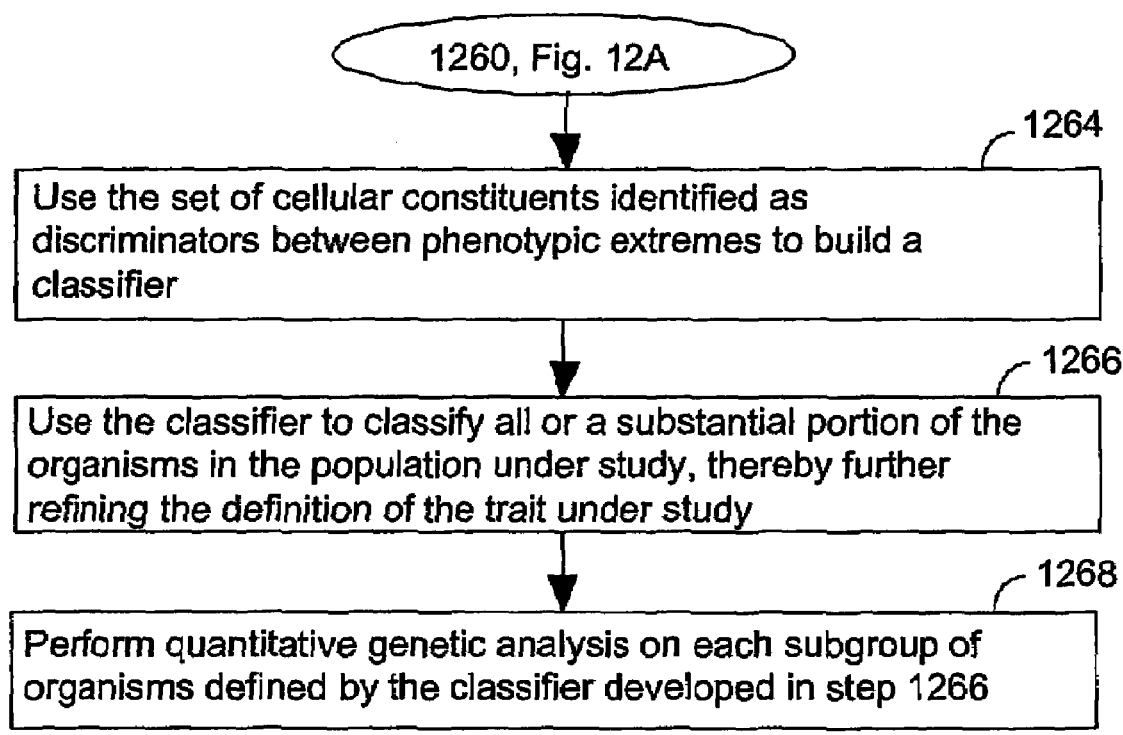

Step 1268. The steps leading to and including step 1260 identify cellular constituents from phenotypically extreme organisms that are differentially expressed. In step 1264, this set of cellular constituents is used to construct a classifier. As illustrated in FIG. 12, in step 1266, the classifier constructed in step 1264 classifies the trait under study into subgroups 1250 without consideration of phenotypic data. It is expected that subgroups 1250 define subgroups of the trait under study and that each of the subgroups define some form of homogenous biochemical form of the trait under study. The biochemical homogeneity in each group 1250 can be exploited using quantitative genetic methods in order to identify genes and biochemical pathways that affect the trait under study, as detailed below.

Regardless of its form, the classifier formed in step 1264 serves to further refine the phenotypic groups 1410 defined in step 1252 or the subgroups 1420 defined in step 1260. As such, the methods disclosed in this section can be used to refine a trait under study. This refinement is illustrated in FIG. 14. At the outset, the trait under study is exhibited by some population 1200 of organisms 246. In step 1252 of the method, observation of gross (visible, measurable) phenotypes (other than cellular constituent levels) related to the trait are used to divide the general population 1200 into two or more phenotypic groups 1410 (FIG. 14). In step 1260 of the method, optional clustering of select cellular constituents serves to refine a phenotypic group into subphenotypic groups 1420 (FIG. 14).

A benefit of step 1260 is that the clustering in step 1260 refines the trait under study into groups 1420 (FIG. 14) that are not distinguishable using gross observable phenotypic data (other than cellular constituent levels) such as amounts 1301 (FIG. 13). As such, optional step 1260 provides a powerful way to refine the definition of the clinical trait under study by focusing on those cellular constituents that actually give rise to the clinical trait or well reflects the varied biochemical response to that trait. However, the refinement provided in step 1260 is incomplete because it is based on only a select portion of the general population under study, those organisms that represent phenotypic extremes. Accordingly, in step 1264 (FIG. 12), a more robust classifier is built using the initial set of cellular constituents selected based upon phenotypic extremes organisms 246 as a starting point. As illustrated in FIG. 14, in step 1266, the classifier derived in step 1264 classifies the trait under study into highly refined subgroups 1450. Thus, although only gross categories such as groups 1410 or 1420 were used to develop the classifier, the classifier will split the population into clusters that can fall within groups 1410 and/or 1120. These clusters are denoted as subgroups 1450 in FIG. 14. Each of these subgroups 1450 serves to refine the trait under study. In other words, each of the subgroups 1450 is a more homogenous form of the overall trait under study. The classifier classifies the general population without considering phenotypic data (e.g., levels 1301, FIG. 13). Therefore, it is possible that the groups 1450 will not fall neatly within groups 1420 and/or 1410.

The classifier developed using the methods described in this section serves to refine the definition of a trait of interest. Thus, each group 1450 (sub-population) in FIG. 14 identified using the classifier represents a more homogenous population with respect to the trait of interest. Cellular constituent measurements from organisms in respective groups 1450 can be used as quantitative traits in quantitative genetic studies such as linkage analysis (Section 5.2) or association analysis (Section 5.4). It is expected that linkage analysis and/or association analysis using data from individual groups 1450 rather than the general population will provide improved results, particularly in situations where the trait under study is complex and/or is driven by many different genes. In such instances, the individual groups 1250 could represent a more homogenous population or state. Consequently the genes that drive or link to the QTL (or loci) patterns in such populations 1450 could be easier to identify than in the case where cellular constituent data form the entire population is used as quantitative traits in such studies. An example where quantitative genetic analysis on subgroups rather than the general population was used to identify genes associated with a trait of interest is provided in Schadt et al., 2003, Nature 422, p. 297.

5.19. METHODS FOR IDENTIFYING CELLULAR CONSTITUENTS THAT ASSOCIATE WITH A TRAIT

In step 1508 of Section 5.1.1, above, patterns of cellular constituent levels (e.g., gene expression levels, protein abundance levels, etc.) are identified that associate with the trait under study. This section describes a number of different methods by which step 1508 of Section 5.1.1 can be carried out. Those of skill in the art will appreciate that there are a number of additional ways that step 1508 can be carried out, and all such ways are included within the scope of the present invention.

5.19.1. Correlation Analysis

Correlation analysis can be used between the trait of interest and cellular constituent levels. An example of this approach is illustrated in Golub et al., 1999, *Science* 286: 531. Golub et al. developed a class predictor for patients that have acute lymphoblastic leukemia (ALL) versus patients that have acute myeloid leukemia (AML). Expression data for 6817 genes from 37 patients (27 ALL, 11 AML) was obtained. Next, the expression patterns for the 6817 genes in the 37 patients were examined using neighborhood analysis.

In neighborhood analysis, each cellular constituent is represented by an expression vector $v(g)=(e_1, e_2, \ldots, e_n)$ where $e_i$ denotes the expression level (or abundance) of cellular constituent g in the $i^{th}$ organism in a plurality of organisms. A class vector is represented by the idealized expression pattern (abundance) $c=(c_1, c_2, \ldots, c_n)$, where $c_i=1$ or 0 according to whether the $i^{th}$ sample was taken from a patient that belongs to class 1 (e.g., ALL) or class 2 (e.g., AML). Correlation between c and v(g) is measured between a cellular constituent and a class distinction in a variety of ways. For example, the Pearson correlation coefficient or the Euclidean distance can be used. In Golub et al. a measure of correlation, P(g,c), that emphasizes the "signal-to-noise" ratio in using the cellular constituent as a predictor was used. The expressions $[\mu_1(g), \sigma_1(g)]$ and $[\mu_2(g), \sigma_2(g)]$ denote the means and standard deviations of the log of the expression levels (or abundances) of cellular constituent g for the samples in class 1 (e.g. ALL) and class 2 (e.g., AML), respectively, and $P(g,c)=[\mu_1(g)-\mu_2(g)]/[\sigma_1(g)+\sigma_2(g)]$ reflects the difference between the classes relative to the standard deviation within the classes. Large values of |P(g,c)| indicate a strong correlation between the cellular constituent level (e.g. gene expression) and the class distinction, while the sign of P(g,c) being positive or negative corresponds to g being more abundant in class 1 or class 2. Unlike a standard Pearson correlation coefficient, P(g,c) is not confined to the range [−1, +1]. Neighborhoods $N_1(c,r)$ and $N_2(c,r)$ of radius r around class 1 and class 2 are defined to be the sets of cellular constituents such that P(g,c)=r and P(g,c)=−r, respectively. An unusually large number of cellular constituents within the neighborhoods indicates that many cellular constituents have abundances (e.g., expression patterns) closely correlated with the class vector.

From the neighborhood analysis, a set of informative cellular constituents (a set of cellular constituents that discriminate between class 1 and class 2; a set of cellular constituents that discriminate the trait) can be chosen. In Golub et al., for example, the set of informative cellular constituents consists of the n/2 genes closest to a class vector high in class 1 [that is, P(g,c) as large as possible] and the n/2 genes closest to class 2 [that is, −P(g,c) as large as possible].

5.19.2. T-Test

Another method that can be used to identify cellular constituent levels (e.g. gene expression levels, protein abundance levels, etc.) that associate with the trait under study is the t-test. The t-test assesses whether the means of two groups are statistically different from each other. When the t-test is used, processing step 1508 of Section 5.1.1, above, seeks to identify those cellular constituents that have significantly different mean abundances in the classes of organism 246. For example, in the case where the plurality of organisms 246 is divided into two groups, those that have been treated with a drug and those that have not, the t-test is used to find those cellular constituents that have a significantly different mean expression level in the organisms that were treated with a drug versus those organisms that were not treated with a drug. See, for example, Smith, 1991, Statistical Reasoning, Allyn and Bacon, Needham Heights, Mass., pp. 361-365. The t-test is represented by the following formula:

$$t = \frac{\overline{X}_T - \overline{X}_C}{\sqrt{\frac{\text{var}_T}{n_T} + \frac{\text{var}_C}{n_C}}}$$

where, the numerator is the numerator is the difference between the mean level of a given cellular constituent in a first group (T) and a second group (C); and $\text{var}_T$ is the variance (square of the deviation) in the level of the given cellular constituent in group T;

$\text{var}_C$ is the variance (square of the deviation) in the level of the given cellular constituent in group C;

$n_T$ is the number of organisms 46 in group T; and $n_C$ is the number of organisms 46 in group C.

The t-value will be positive if the first mean is larger than the second and negative if it is smaller. The significance of any t-value is determined by looking up the value in a table of significance to test whether the ratio is large enough to say that the difference between the groups is not likely to have been a chance finding. To test the significance, a risk level (called the alpha level) is set. In some embodiments of the present invention the alpha level is set at 0.05. This means that five times out of a hundred there would be a statistically significant difference between the means even if there was none (i.e., by "chance"). In some embodiments, the alpha level is set at 0.025, 0.01 or 0.005. Further, to test significance, the number of degrees of freedom (df) for the test needs to be determined. In the t-test, the degrees of freedom is the sum of the persons in both groups (T and C) minus 2. Given the alpha level, the df, and the t-value, it is possible to look the t-value up in a standard table of significance (see, for example, Table III of Fisher and Yates, *Statistical Tables for Biological, Agricultural, and Medical Research*, Longman Group Ltd., London) to determine whether the t-value is large enough to be significant. In some embodiments, a cellular constituent is considered to discriminate between two groups of organisms 246 (e.g. a first group that is treated with a compound and a second group that is not treated with a compound) when t is 3 or greater, 4 or greater, 5 or greater, 6 or greater, or 7 or greater.

5.19.3. Paired T-Test

Another method that can be used to identify cellular constituent levels (e.g., gene expression levels, protein abundance levels, etc.) that associate with the trait under study is the paired t-test. The paired t-test assesses whether the means of two groups are statistically different from each other. The paired t-test is generally used when measurements are taken from the same organism 246 before and after some perturbation, such as injection of a drug. For example, the paired t-test can be used in embodiments of processing step 1508 of Section 5.1.1 to determine the significance of a difference in blood pressure before and after administration of a compound that affects blood pressure. The paired t-test is represented by the following formula:

$$t = \frac{\overline{d}}{S_d/\sqrt{n}}$$

where,
the numerator is the paired sample mean;
Sd is the paired sample deviation; and
n is the number of pairs considered.

5.19.4. Other Parametric Statistical Tests

When statistics are calculated under the assumption that the data follow some common distribution, such as the normal distribution, they are termed parametric statistics. It follows that statistical tests based on these parametric statistics are called parametric statistical tests. Thus, when the data has a normal distribution, any number of well-known parametric statistical tests can be used in processing step 1508 of Section 5.1.1. Such tests include, but are not limited to the t-tests described above, analysis of variance (ANOVA), repeated measures ANOVA, Pearson correlation, simple linear regression, nonlinear regression, multiple linear regression or multiple nonlinear regression. For example, regression can be used to see how two variables (two different cellular constituents) vary together.

5.19.5. Nonparametric Statistical Tests

Tests that do not make assumptions about the population distribution are referred to as non-parametric tests. In some embodiments of processing step 1508 of Section 5.1.1, non-parametric tests are used. In some embodiments, a Wilcoxon signed-rank test, a Mann-Whitney test, a Kruskal-Wallis test, a Friedman test, a Spearman rank order correlation coefficient, a Kendall Tau analysis, or a nonparametric regression test is used.

5.20. EXAMPLES

The following examples are presented by way of illustration of the previously described invention and are not limiting of that description.

5.20.1. Exemplary Sources of Genotype and Pedigree Data

Figure 9:
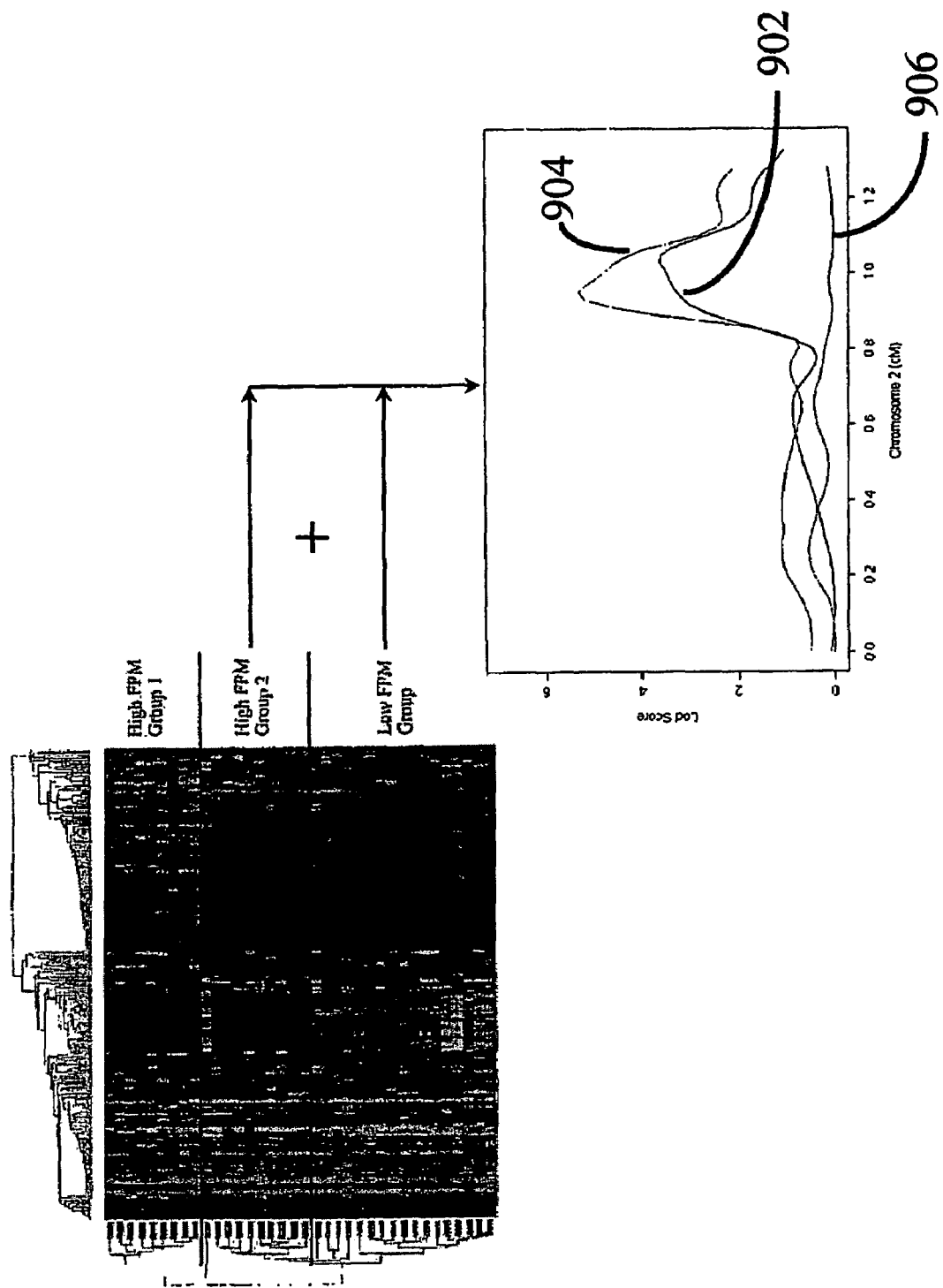
FIG. 9 illustrates the results of a QTL analysis of a portion of mouse chromosome 2 in accordance with one embodiment of the present invention.

Mice. The methods of the present invention are applicable to any living organism in which genetic variation can be tracked. Therefore, by way of example, genotype and/or pedigree data 68 (FIG. 1) is obtained from experimental crosses or a human population in which genotyping information and relevant clinical trait information is provided. One such experimental design for a mouse model for complex human diseases is given in FIG. 9. In FIG. 9, there are two parental inbred lines that are crossed to obtain an $F_1$ generation. The $F_1$ generation is intercrossed to obtain an $F_2$ generation. At this point, the $F_2$ population is genotyped and physiologic phenotypes for each $F_2$ in the population are determined to yield genotype and pedigree data 68. These same determinations are made for the parents as well as a sampling of the $F_1$ population.

Human populations. The present invention is not constrained to model systems, but can be applied directly to human populations. For example, pedigree and other genotype information for the Ceph family is publicly available (Center for Medical Genetics, Marshfield, Wis.), and lymphoblastoid cell lines from individuals in these families can be purchased from the Coriell Institute for Medical Research (Camden, N.J.) and used in the expression profiling experiments of the instant invention. The plant, mouse, and human populations discussed in this section represent non-limiting examples of genotype and/or pedigree for use in the present invention.

5.20.2. Fat Pad Mass Example

The following example illustrates one embodiment of the method disclosed in FIG. 1.

Step 102. An F2 intercross was constructed from C57BL/6J and DBA/2J strains of mice. All mice were housed under conditions meeting the guidelines of the Association for Accreditation of Laboratory Animal Care. Mice were on a rodent chow diet up to 12 months of age, and then switched to an atherogenic high-fat, high-cholesterol diet for another 4 months. More details on this cross are described in Drake et al., 2001, Physiol. Genomics 5, p. 205. Parental and F2 mice were sacrificed at 16 months of age. At death the livers were immediately removed, flash-frozen in liquid nitrogen and stored at −80° C. Total cellular RNA was purified from 25 mg portions using an Rneasy Mini kit according to the manufacturer's instructions (Qiagen, Valencia, Calif.). Competitive hybridizations were performed by mixing fluorescently labeled cRNA (5 mg) from each of 111 female F2 liver samples, 5 DBA/2J liver samples, and 3 C57BL/6J liver samples, with the same amount of cRNA from a reference pool comprised of equal amounts of cRNA from each of the 111 liver samples profiled.

The F2 mice constructed from the inbred strains C57BL/6J and DBA/2J as described above model the spectrum of disease in a natural population, with many mice developing atherosclerotic lesions, and others having significantly higher fat-pad masses, higher cholesterol levels and larger bone structures than others in the same population. See, for example, Drake, 2001, J. Orthop Res 19, p. 511, and Drake, 2001, Physiol. Genomics 5, p. 205.

The competitive expression values for genes from the livers of the 111 F2 mice were determined using a microarray that included 23,574 genes. Array images were processed as described in Hughes, 2000, Cell 102, p. 109 to obtain background noise, single channel intensity, and associated measurement error estimates. Expression changes between liver samples and reference pools were quantified as $\log_{10}$ (expression ratio) where the 'expression ratio' was taken to be the ratio between normalized, background-corrected intensity values for the two channels (red and green/liver sample and reference pool) for each spot on the array. An error model for the log ratio was applied as described in Roberts, 2000, Science 287, p. 873, to quantify the significance of expression changes between the liver sample and the reference pool.

Step 104—Yes. The class predictor 262 used in this example is derived from a collection of informative genes that are differentially expressed in various subdivisions of the complex trait subcutaneous fat pad mass (FPM). FPM is a quantifiable mouse phenotypic trait. See, for example, Schadt et al., 2003, Nature. 422, p. 297. To this end, 280 genes were selected as the most differentially expressed set of genes in mice comprising the upper and lower 25th percentiles of the subcutaneous fat pad mass (FPM) trait. This set of genes (the FPM set) can be considered as the most transcriptionally active set of genes for mice falling in the tails of the FPM trait distribution. The selection of this gene set was not biased by selecting genes based on their ability to discriminate between the FPM trait extremes.

Step 108. Rather than using the 280 genes in a supervised classification scheme (FIG. 1, step 106), the 280 genes were used in an unsupervised classification scheme. Although not shown in FIG. 1, the use of an unsupervised classification scheme despite the existence of a classifier is practice in one embodiment of the invention that is disclosed in Section 5.1.

For step 108, expression vectors for each of the 280 genes were constructed. Each expression vector included the expression value of a given gene in the set of 280 genes across all mice in the F2 population. Thus, for example, the expression vector for a given gene i in the set of 280 genes included 111 expression values, with each expression value representing the expression of gene i in a respective mouse in the F2 population.

Figure 8:
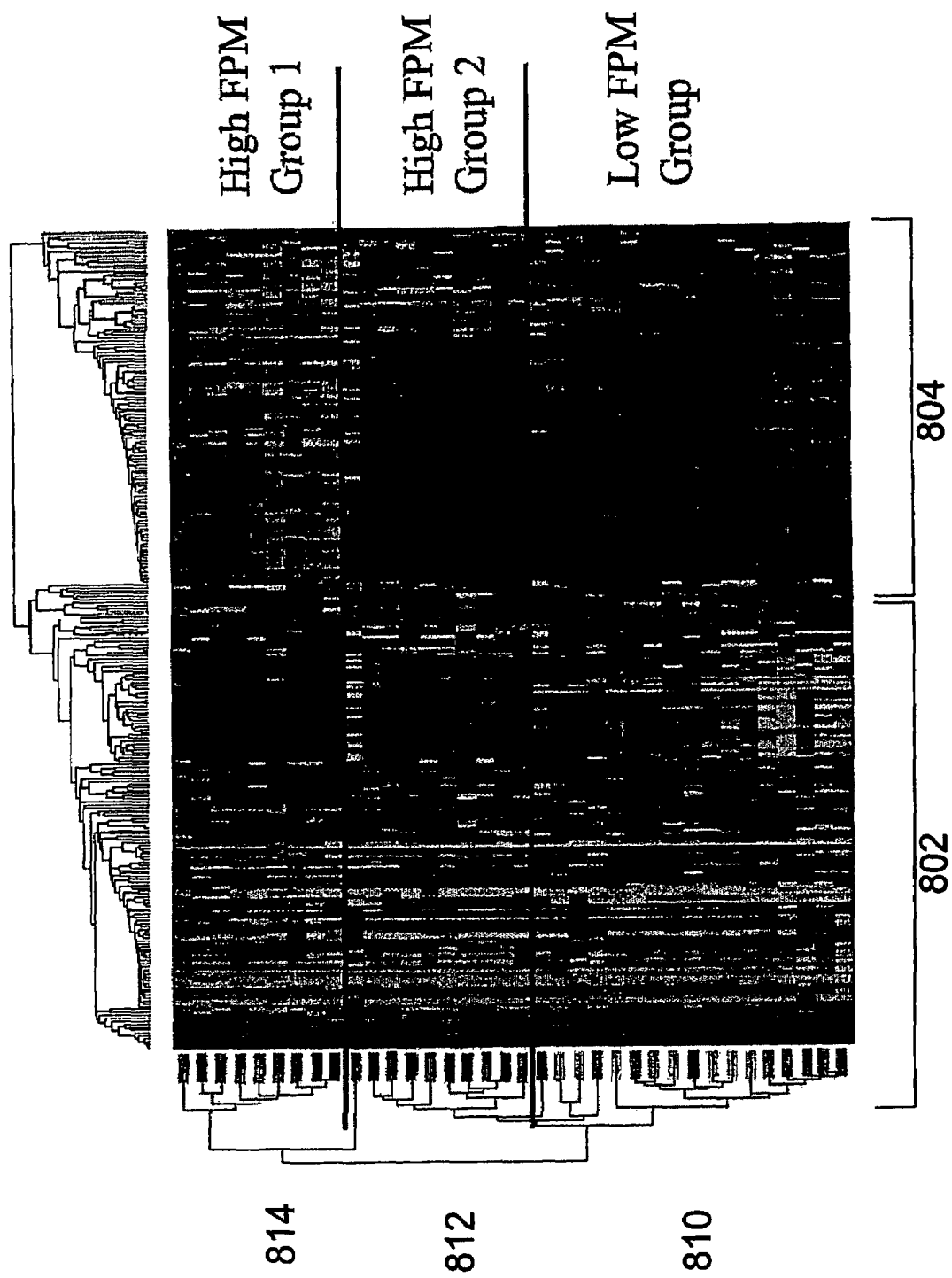
FIG. 8 illustrates hierarchically clustered genes and extreme fat pad mass mice.

FIG. 8 represents a two-dimensional cluster analysis. On the x-axis, the expression vectors for each of the 280 genes are clustered. To form the clustering on the y-axis, a vector was constructed for each of the 111 mice. Each such vector includes the expression value for each of the 280 genes considered in the respective mouse associated with the vector. Then these vectors are clustered along the y-axis. Thus, in FIG. 8, the x-axis clusters genes that express similarly across the population of mice and the y-axis clusters mice that have similar gene expression values for the set of 280 genes. Each x,y coordinate in the two-dimensional graph represents the expression level of a gene in a given organism. Although not clearly shown in FIG. 8, each x,y coordinate in the two-dimensional graph is color coded to indicate the expression level of the gene in the given organism relative to a reference pool.

The two-dimensional cluster analysis illustrated in FIG. 8 allows for the determination of subgroups in the population. Clearly such subpopulations will be defined by clusters on the y-axis. However, the patterns produced by the clustering on the x-axis aid in defining the subpopulations on the y-axis. Namely, each subgroup on the y-axis should have a similar patterns of expression across the 280 member gene set. Analysis of FIG. 8 reveals three such sets. The y-axis was not clustered based on a clinical trait. Nevertheless, the mice on the y-axis cluster into distinct phenotypic groups. The first set is the low fat pad mass group. The low fat pad mass group is defined by two factors. First, the low fat pad mass group define a cluster on the y-axis. Second, genes in the low fat pad mass group that are in set 802 tend to be green-shifted relative to the reference pool whereas as genes in set 804 tend to be red-shifted relative to the reference pool. The expression pattern of the genes in the 280 member set along the y-axis serve to validate that the low fat pad mass group in not, in fact, a composite of two or more subgroups. Continuing with this form of analysis, two other groups (high fat pad mass 1 and high fat pad mass 2) are defined on the y-axis and validated by the pattern of expression along the y-axis as summarized in the following table:

| Name | Y-axis | X-axis - gene set 802 | X-axis - gene set 804 |
|---|---|---|---|
| Low FPM | Cluster 810 | Green | Red |
| High FPM 2 | Cluster 812 | Green | Red |
| High FPM 1 | Cluster 814 | Green/red | Green |

Steps 112 and 114. The patterns realized in FIG. 8 serve to define the obesity trait, FPM. In fact, these patterns refine the definition of FPM beyond what would be possible without the expression data. There are clearly two distinct patterns associated with high FPM mice depicted in FIG. 8 (High FPM 2 and High FPM 1). Heterogeneity of expression patterns associated with a clinical trait, almost certainly points to heterogeneity in the clinical trait itself.

To further elucidate this clinical trait, the 111 F2 animals for which clinical and gene expression data existed were classified into one of the three groups depicted in FIG. 8. Subsequently, separate linkage analyses (Section 5.2) were performed on two sets of animals: 1) those classified as high FPM group 1 or low FPM, and 2) those classified as high FPM group 2 or low FPM. In this linkage analysis, the quantitative trait FPM was analyzed using the above-identified subpopulations rather than the whole population.

Figure 10:
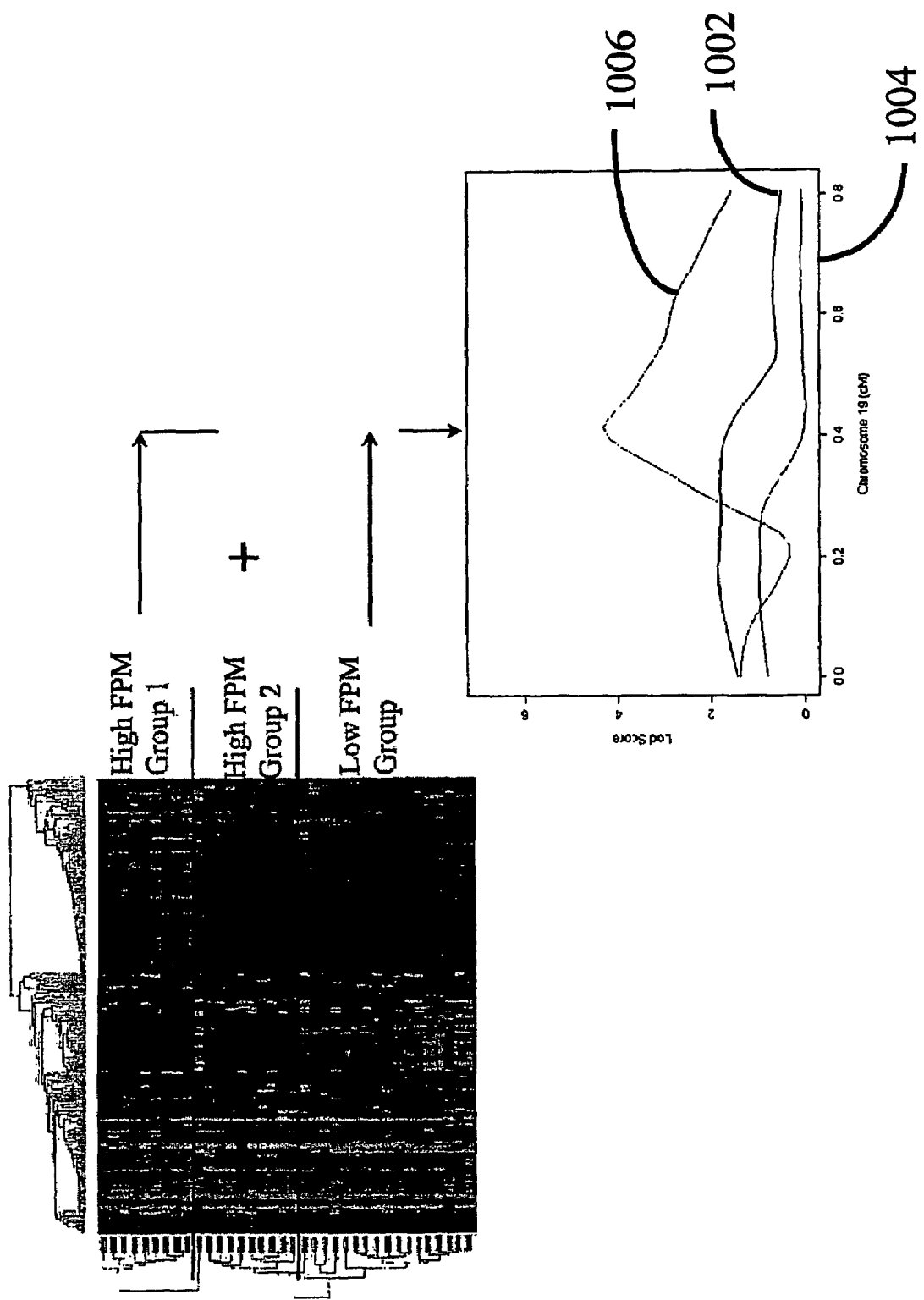
FIG. 10 illustrates the results of a QTL analysis of a portion of mouse chromosome 19 in accordance with one embodiment of the present invention.

FIGS. 9 and 10 depict the results of these analyses for two chromosomes. The chromosome 2 FPM QTL (FIG. 9) was the largest of four QTL originally identified for FPM when all animals were considered together. The magnitude of the QTL at this position of chromosome 2 using all mice in the linkage analysis is depicted by curve 902. However, this QTL vanishes when considering the high FPM group 1 with the low FPM group (FIG. 9, curve 906), but then increases by almost 2 lod units over curve 902 when considering the high FPM group 2 with the low FPM group (FIG. 9, curve 904).

FIG. 10 depicts a locus for which the original analysis on the full set of mice yielded no significant QTL for the FPM trait on chromosome 19 (FIG. 10, curve 1002), but the high FPM group 2 considered with the low FPM group gave rise to a QTL (FIG. 10, curve 1006) with a significant lod score, while the high FPM group 1 considered with the low FPM group was less significant than the that of the full set (FIG. 10, curve 1004).

The results of this example indicate that the chromosome 2 and 19 QTL each significantly affect only a subset of the F2 population, a form of heterogeneity that speaks directly to the complexity underlying traits such as obesity. Further, the chromosome 19 QTL explains 19% of the variation in the FPM trait for the high FPM group 1/low FPM subset, but would have been completely missed if the expression data had not been used to define the subphenotypes. The significances of the QTL with the highest lod scores depicted in FIGS. 9 and 10 were assessed by repeatedly sampling (10,000 times) from the full set of F2 animals so that groups equal in size to the high FPM group 1/low FPM and high FPM group 2/low FPM groups were obtained for each iteration. None of the 10,000 samplings obtained QTL approaching the significances of those given in FIGS. 9 and 10.

An expanded view of the clinical traits and a portion of the gene expression traits linking to the chromosome 2 locus discussed above and described in FIG. 9, is given in FIG. 11. Co-localized with the FPM QTL are other QTL for obesity-related traits described by Drake et al., 2001, Physiol.

Genomics 5, p. 205. These traits include adiposity, fat pad mass, plasma lipid levels and bone density. FIG. 11 shows the lod score curves for four of the obesity-related traits. Interestingly, a group of major urinary protein genes (MUP1, MUP4 and MUP5) are linked to the chromosome 2 locus, in addition to seven other loci (all with LOD score exceeding 2.0), four of which co-localize with adiposity or fat pad mass traits. The MUP1 gene stands out because it was the most highly correlated with many other genes known to be involved in obesity-related pathways, including retinoid X receptor (RXR) gamma (R=0.75/P-value $\ll 1.0E^{-15}$), acyl-Coenzyme A oxidase 1 (R=0.65/P-value=$3.78E^{-15}$), and leptin receptor (R=−0.74/P-value $\ll 1.0E^{-15}$), in addition to having QTL that co-localize with other genes like peroxisome proliferator activated receptor (PPAR) gamma, RXR interacting protein and LPR6, all known to be involved in these pathways. Mutations in the leptin receptor in mice and man cause hyperphagia and extreme obesity. See, fore example, Chen et al., 1996, Cel 84, p. 492; Chua et al., 1996, Science 271, p. 994, Clement et al., 1998, Nature 392, p. 398, Montague et al., 1997, Nature 387, p. 903; Strobel et al., 1998, Nat. Genet. 18, p. 213; and Tsigos et al., 2002, J Pediatr Endocrinol Metab. 15, p. 241. RXR is the obligate partner of many nuclear receptors including PPARα and PPARγ that are involved in many aspects of the control of lipid metabolism, glucose tolerance and insulin sensitivity. See, for example, Chawla, 2001, Science 294, p. 1866. This demonstrates that the chromosome 2 locus draws together adiposity, fat pad mass, cholesterol and triglyceride levels and is linked to genes with proven roles in obesity and diabetes. Further, the MUP genes are members of the lipocalin protein family, and while they are known to play a central role in phenone-binding processes that affect mouse physiology and behavior (Timm et al., 2001, Protein Science 10, p. 997), variations in MUP expression have been associated with variations in body weight and bone length (Metcalf et al., 2000, Nature 405, p. 1068), as well as VLDL levels (Swift et al., 2001, J. Lipid Res. 42, p. 218).

The region supporting the chromosome 2 locus is homologous to human chromosome 20q12-q13.12, a region that has previously been linked to human obesity-related phenotypes. See, for example, Borecki et al., 1994, Obesity Research 2, p. 213; Lembertas, 1997, J. Clin. Invest 100, p. 1240). The human homologues for genes NM_025575 and NM_015731 highlighted in 11 reside in the human chromosome 20 region and have not been completely characterized; they have not been implicated in obesity-related traits before. While other genes such as melanocortin 3 receptor (MC3R) have been suggested as possible candidates for obesity at this locus (Lembertas et al., 1997, J. Clin Invest. 100, p. 1240), the data in this example suggests that the genes NM_025575 and NM_015731 may be responsible for the underlying QTL, which are not only significantly linked to the murine chromosome 2 locus, but that are also significantly interacting with several of the fat pad mass traits also linked to the chromosome 2 locus. The expression levels for MC3R are not linked to the chromosome 2 locus, and there were no SNPs annotated in the exons or introns of this gene between the C57/BL6 and DBA/2J strains in a recent build of the Celera RefSNP database. Unless polymorphic expression of MC3R in the brain partially drives expression in the liver for genes linked to the chromosome 2 locus, these facts would suggest that MC3R is not the gene underlying the chromosome 2 linkage in this case.

In summary, F2 animals were classified into one of three groups (high FPM 1, high FPM 2, and low FPM) using the methods of the present invention. The animals were then genetically analyzed using QTL methods applied to the different high FPM groups, each combined with the low FPM group for the analysis. The results for the distal end of chromosome 2 were presented. The FPM QTL in this region of chromosome 2 completely vanishes when considering one of the high FPM groups of mice, but then increases by almost 2 lod units over the original lod score when considering the other high FPM group of mice. In addition, another interesting locus was discovered on chromosome 19 that had been completely missed when all mice were considered simultaneously. In this instance, the high FPM group of mice that was not under the influence of chromosome 2 QTL, gave rise to a QTL with a significant lod score, while the other high FPM group had a lod score that was less significant than that obtained for the full set.

The results of this example provide the first-ever evidence that gene expression patterns can be used to refine the definition of a clinical trait into subtypes that are under the control of different genetic loci. The implications for drug discovery are significant and speak directly to the difficulty in dissecting complex diseases. Clearly, developing a compound that targeted only the gene underlying the FPM chromosome 2 QTL would be completely ineffective for those in the high FPM group 1 (since they are not controlled by this locus), but would be quite effective for those in the high FPM 2 group (since they are controlled by this locus). Treating all obese individuals together in one group would result in a much less efficacious treatment than could otherwise be achieved by identifying those that would respond to the treatment. Further, by defining the subpopulation most likely to respond to a given drug treatment as one of many subpopulations making up the population of all obese patients, the drug development and diagnostic components of the pharmaceutical industry will tend toward a natural restructuring that allows each component to become more productive by stratifying populations according to treatment groups at the earliest possible stages of drug development. This progressive strategy will more intimately link the two classically independent worlds of drug development and diagnostics. Similar arguments can be made for studying toxicity, since adverse response to a drug is also a complex trait that can be dissected in a fashion similar to that described above.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1. These program modules may be stored on a CD-ROM, magnetic disk storage product, or any other computer readable data or program storage product. The software modules in the computer program product may also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for identifying a quantitative trait locus for a complex trait that is exhibited by a plurality of organisms in a population, comprising:
(a) dividing said population into a plurality of sub-populations using a classification scheme that classifies each organism in said population into at least one of said sub-populations, wherein said classification scheme is derived from a plurality of cellular constituent measurements for each of a plurality of respective cellular constituents that are measured from each said organism; and
(b) performing, for at least one sub-population in said plurality of sub-populations, quantitative genetic analysis on said sub-population in order to identify said quantitative trait locus for said complex trait; wherein said dividing step (a) and performing step (b) are executed using a suitably programmed computer.

2. The method of claim 1, wherein said plurality of cellular constituent measurements from each said organism are transcriptional state measurements or translational state measurements.

3. The method of claim 1, wherein said plurality of cellular constituent measurements from each said organism comprises translational state measurements that are performed using an antibody array or two-dimensional gel electrophoresis.

4. The method of claim 1, wherein said plurality of respective cellular constituents comprises a plurality of metabolites and said plurality of cellular constituent measurements are derived by a cellular phenotypic technique.

5. The method of claim 4, wherein said cellular phenotypic technique comprises a metabolomic technique wherein a plurality of levels of metabolites in each said organism is measured.

6. The method of claim 5, wherein a metabolite in said plurality of metabolites comprises an amino acid, a metal, a soluble sugar, or a complex carbohydrate.

7. The method of claim 5, wherein said plurality of levels of metabolites is measured by use of pyrolysis mass spectrometry, Fourier-transform infrared spectrometry, Raman spectrometry, gas chromatography-mass spectroscopy, capillary electrophoresis, high pressure liquid chromatography/mass spectroscopy (HPLC/MS), liquid chromatography (LC)-electrospray mass spectroscopy, or cap-LC-tandem electrospray mass spectroscopy.

8. The method of claim 1 wherein said plurality of cellular constituent measurements comprises abundance of mRNA, protein expression levels, or metabolite levels.

9. The method of claim 1, wherein said complex trait is characterized by an allele that exhibits incomplete penetrance in said population.

10. The method of claim 1, wherein said complex trait is a disease that is contracted by an organism in said population, and wherein said organism inherits no predisposing allele to said disease.

11. The method of claim 1, wherein said complex trait arises when any of a plurality of different genes in the genome of said plurality of organisms is mutated.

12. The method of claim 1, wherein said complex trait requires the simultaneous presence of mutations in a plurality of genes in the genome of said plurality of organisms.

13. The method of claim 1, wherein said complex trait is associated with a high frequency of disease-causing alleles in said population.

14. The method of claim 1, wherein said complex trait is a phenotype that does not exhibit Mendelian recessive or dominant inheritance attributable to a single gene locus.

15. The method of claim 1, wherein said complex trait is asthma, ataxia telangiectasia, bipolar disorder, cancer, common late-onset Alzheimer's disease, diabetes, heart disease, hereditary early-onset Alzheimer's disease, hereditary non-polyposis colon cancer, hypertension, infection, maturity-onset diabetes of the young, mellitus, migraine, nonalcoholic fatty liver, nonalcoholic steatohepatitis, non-insulin-dependent diabetes mellitus, obesity, polycystic kidney disease, psoriases, schizophrenia, or xeroderma pigmentosum.

16. The method of claim 1, wherein said plurality of cellular constituent measurements from each said organism comprises the measurement of the cellular constituent levels often or more cellular constituents in each said organism.

17. The method of claim 1, wherein said plurality of cellular constituent measurements from each said organism comprises the measurement of the cellular constituent levels of one thousand or more cellular constituent levels in each said organism.

18. The method of claim 1, wherein said dividing step (a) comprises determining whether a class predictor is available, and
when a class predictor is available, using a supervised classification scheme to classify each organism in said population into a sub-population in said plurality of sub-populations; and
when a class predictor is not available, using an unsupervised classification scheme to classify each organism in said population into a sub-population in said plurality of sub-populations.

19. The method of claim 1, wherein said classification scheme is a supervised classification scheme.

20. The method of claim 1, wherein said classification scheme is an unsupervised classification scheme.

21. The method of claim 18 or 19, wherein said supervised classification scheme uses linear discriminant analysis or a linear regression method.

22. The method of claim 21, wherein said supervised classification scheme uses a linear regression method and wherein said linear regression method uses multiple linear regression, partial least squares regression, or principal components regression.

23. The method of claim 18 or 20, wherein said unsupervised classification scheme is selected from the group consisting of a hierarchical cluster analysis, a non-hierarchical cluster analysis, an artificial neural network, and a self-organizing map.

24. The method of claim 23, wherein said unsupervised classification scheme is a hierarchical cluster analysis that uses a nearest-neighbor algorithm, a farthest-neighbor algorithm, an average linkage algorithm, a centroid algorithm, or a sum-of-squares algorithm to determine the similarity between (i) the plurality of cellular constituent measurements from one organism in said plurality of organisms and (ii) the plurality of cellular constituent measurements from another organism in said plurality of organisms.

25. The method of claim 23, wherein said unsupervised classification scheme is hierarchical cluster analysis selected from the group consisting of agglomerative clustering, polythetic divisive clustering, and monthetic divisive clustering.

26. The method of claim 25, wherein said hierarchical cluster analysis is an agglomerative clustering using Pearson correlation coefficients, Euclidean distance, squared Euclidean distance, Euclidean sum of squares, a Manhattan metric, or squared Pearson correlation coefficients to determine similarity between (i) the plurality of cellular constituent measurements from one organism in said plurality of organisms and (ii) the plurality of cellular constituent measurements from another organism in said plurality of organisms.

27. The method of claim 23, wherein said unsupervised classification scheme is non-hierarchical cluster analysis selected from the group consisting of K-means clustering, fuzzy k-means clustering, and Jarvis-Patrick clustering.

28. The method of claim 23, wherein said unsupervised classification scheme is an artificial neural network that is a Kohonen artificial neural network or an auto-associative neural network.

29. The method of claim 1, wherein said dividing step (a) further comprises verifying the division of said population into said plurality of sub-populations.

30. The method of claim 1, wherein said quantitative genetic analysis is performed using a method selected from the group consisting of a linkage analysis, a quantitative trait locus (QTL) analysis method that uses said plurality of cellular constituent measurements as a phenotypic trait, and an association analysis.

31. The method of claim 30, wherein said quantitative genetic analysis is performed using said QTL analysis method, said QTL analysis method comprising:
(a) clustering QTL data from a plurality of QTL analyses to form a QTL interaction map, wherein
each QTL analysis in said plurality of QTL analyses is performed for a gene G in a plurality of genes in the genome of said plurality of organisms using a genetic marker map and a quantitative trait in order to produce said QTL data, wherein, for each QTL analysis, said quantitative trait comprises an expression statistic for the gene G, for which the QTL analysis has been performed, for each organism in said plurality of organisms; and wherein
said genetic marker map is constructed from a set of genetic markers associated with said plurality of organisms; and
(b) analyzing said QTL interaction map to identify said QTL associated with said quantitative trait.

32. The method of claim 31, which further comprises, prior to said clustering step, a step of constructing said genetic marker map from said set of genetic markers associated with said plurality of organisms.

33. The method of claim 31, which further comprises, prior to said clustering step, a step of performing each said QTL analysis in said plurality of QTL analyses.

34. The method of claim 31, wherein said expression statistic for said gene G is computed by a method comprising transforming an expression level measurement of said gene G from each organism in said plurality of organisms.

35. The method of claim 34, wherein said step of transforming an expression level measurement of said gene G comprises normalizing the expression level measurement of said gene G in order to form said expression statistic.

36. The method of claim 35, wherein normalizing the expression level measurement of said gene G in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

37. The method of claim 31, wherein each said QTL analysis comprises:
(i) testing for linkage between a position in the genome of said plurality of organisms, and the quantitative-trait used in the QTL analysis;
(ii) advancing the position in said genome by an amount; and
(iii) repeating steps (i) and (ii) until all or a portion of the genome has been tested.

38. The method of claim 37, wherein said amount is less than 100 centiMorgans.

39. The method of claim 37, wherein said amount is less than 10 centiMorgans.

40. The method of claim 37, wherein said amount is less than 5 centiMorgans.

41. The method of claim 37, wherein said amount is less than 2.5 centiMorgans.

42. The method of claim 37, wherein said QTL data produced from each respective QTL analysis comprises a statistical score computed at each said position.

43. The method of claim 37, the method further comprising creating a QTL vector for each quantitative trait tested in said chromosome, wherein said QTL vector comprises a statistical score for each position tested by the QTL analysis corresponding to the quantitative trait.

44. The method of claim 43, wherein said clustering of QTL data comprises clustering each said QTL vector.

45. The method of claim 43, wherein a similarity metric that is used as a basis for said clustering is a Euclidean distance, a squared Euclidean distance, a Euclidean sum of squares, a Manhattan metric, a Pearson correlation coefficient, or a squared Pearson correlation coefficient, and wherein the similarity metric is computed between QTL vector pairs.

46. The method of claim 31 or 44, wherein said clustering of QTL data comprises applying a hierarchical clustering technique, applying a k-means technique, applying a fuzzy k-means technique, applying a Jarvis-Patrick clustering, applying a self-organizing map technique, or applying a neural network technique.

47. The method of claim 46, wherein said clustering of QTL data comprises applying a hierarchical clustering technique, wherein said hierarchical clustering technique is an agglomerative clustering procedure.

48. The method of claim 47, wherein said agglomerative clustering procedure is a nearest-neighbor algorithm, a farthest-neighbor algorithm, an average linkage algorithm, a centroid algorithm, or a sum-of-squares algorithm.

49. The method of claim 46, wherein said hierarchical clustering technique is a divisive clustering procedure.

50. The method of claim 35, which further comprises constructing a gene expression cluster map from each expression statistic created by said transforming step.

51. The method of claim 50, wherein said constructing a gene expression cluster map comprises:
creating a plurality of gene expression vectors, each gene expression vector in said plurality of gene expression vectors representing an expression level measurement of a gene, in said plurality of genes, in each of the plurality of organisms;
computing a plurality of correlation coefficients, wherein each correlation coefficient in said plurality of correlation coefficients is computed between a gene expression vector pair in said plurality of gene expression vectors; and clustering said plurality of gene expression vectors based on said plurality of correlation coefficients in order to form said gene expression cluster map.

52. The method of claim 51, wherein said step of analyzing said QTL interaction map (b) comprises filtering the QTL interaction map in order to obtain a candidate pathway group; and wherein the filtering comprises identifying a QTL in said candidate pathway group in said gene expression cluster map.

53. The method of claim 51, wherein each correlation coefficient in said plurality of correlation coefficients is a Pearson correlation coefficient.

54. The method of claim 50, wherein said constructing a gene expression cluster map comprises:
creating a plurality of gene expression vectors, each gene expression vector in said plurality of gene expression vectors representing a gene in said plurality of genes;
computing a plurality of metrics, wherein each metric in said plurality of metrics is computed between a gene expression vector pair in said plurality of gene expression vectors; and
clustering said plurality of gene expression vectors based on said plurality of metrics in order to form said gene expression cluster map.

55. The method of claim 54, wherein each said metric is selected from the group consisting of a Euclidean distance, a squared Euclidean distance, a Euclidean sum of squares, a Manhattan metric, a Pearson correlation coefficient, and a squared Pearson correlation coefficient.

56. The method of claim 51 or 54, wherein said clustering of the plurality of gene expression vectors comprises applying a hierarchical clustering technique, applying a k-means technique, applying a fuzzy k-means technique, applying a Jarvis-Patrick clustering, applying a self-organizing map technique, or applying a neural network technique.

57. The method of claim 56, wherein said clustering of the plurality of gene expression vectors comprises applying a hierarchical clustering technique, wherein said hierarchical clustering technique is an agglomerative clustering procedure.

58. The method of claim 57, wherein said agglomerative clustering procedure is a nearest-neighbor algorithm, a farthest-neighbor algorithm, an average linkage algorithm, a centroid algorithm, or a sum-of-squares algorithm.

59. The method of claim 56, wherein said clustering of the plurality of gene expression vectors comprises applying a hierarchical clustering technique, wherein said hierarchical clustering technique is a divisive clustering procedure.

60. The method of claim 31, wherein said step of analyzing said QTL interaction map (b) comprises filtering the QTL interaction map in order to obtain a candidate pathway group.

61. The method of claim 60, wherein said filtering in order to obtain said candidate pathway group comprises selecting those QTL for said candidate pathway group that interact most strongly with another QTL in said QTL interaction map.

62. The method of claim 61, wherein said QTL that interact most strongly with another QTL in said QTL interaction map are those QTL in said QTL interaction map that share a correlation coefficient with another QTL in said quantitative trait locus interaction map that is higher than 75% of all correlation coefficients computed between QTL in said quantitative trait locus interaction map.

63. The method of claim 61, the method further comprising fitting a multivariate statistical model to said candidate pathway group in order to test the degree to which each QTL making up the candidate pathway group belongs in the candidate pathway group.

64. The method of claim 63, wherein said multivariate statistical model simultaneously considers multiple quantitative traits.

65. The method of claim 63, wherein said multivariate statistical model looks for epistatic interactions between QTL in said candidate pathway group.

66. The method of claim 31, wherein said set of genetic markers comprises a single nucleotide polymorphism (SNP), a microsatellite marker, a restriction fragment length polymorphism, a short tandem repeat, a DNA methylation marker, or a sequence length polymorphism.

67. The method of claim 31, wherein pedigree data is used in step (b) of claim 1, and wherein said pedigree data shows one or more relationships between organisms in said plurality of organisms.

68. The method of claim 42 or 43, wherein pedigree data is used in said performing step (b), and wherein said statistical score is a lod score.

69. The method of claim 1, wherein said plurality of organisms is human.

70. The method of claim 67, wherein said plurality of organisms comprises an $F_2$ population and said one or more relationships between organisms in said plurality of organisms indicates which organisms in said plurality of organisms are members of said $F_2$ population.

71. The method of claim 34, wherein said step of clustering QTL data comprises a step of constructing said genetic marker map from said set of genetic markers associated with said plurality of organisms, and a step of performing each QTL analysis in said plurality of QTL analyses.

72. The method of claim 1, wherein said dividing step (a) comprises:
(i) partitioning said population into a plurality of phenotypic groups using phenotypic data for all or a portion of said plurality of organisms;
(ii) identifying a set of extreme organisms in said plurality of phenotypic groups that represent a phenotypic extreme;
(iii) identifying cellular constituents within said plurality of cellular constituents, wherein each respective identified cellular constituent has the property that cellular constituent measurements for the respective cellular constituent from said set of extreme organisms discriminate all or a portion of said plurality of phenotypic groups; and
(iv) constructing a classifier using a probability distribution derived from all or a portion of said identified cellular constituents.

73. The method of claim 72 wherein said phenotypic data comprises a binary event.

74. The method of claim 72 wherein said phenotypic data comprises more than one phenotypic measurement for each organism in said population.

75. The method of claim 72 wherein said phenotypic data comprises a determination as to whether each organism in said plurality of organisms exhibits a trait, and said partitioning step (i) comprises placing an organism in said plurality of organisms in a first phenotypic group when said organism exhibits said trait and placing an organism in said plurality of organisms in a second phenotypic group when said organism does not exhibit said trait.

76. The method of claim 72 wherein said phenotypic data comprises a plurality of phenotypic measurements that are made for all or a portion of said plurality of organisms, and wherein said partitioning step (i) comprises:
(A) constructing a plurality of phenotypic vectors, each phenotypic vector in said plurality of phenotypic vectors corresponding to an organism in said plurality of organisms, and each respective phenotypic vector in said plurality of phenotypic vectors comprising a plurality of phenotypic measurements from the organism corresponding to the respective phenotypic vector; and (B) clustering said plurality of phenotypic vectors into a plurality of clusters, wherein each cluster in said plurality of clusters represents a phenotypic group in said plurality of phenotypic groups.

77. The method of claim 76 wherein said clustering comprises a hierarchical clustering technique, a k-means technique, a fuzzy k-means technique, a Jarvis-Patrick clustering, a self-organizing map technique, or a neural network technique.

78. The method of claim 76, wherein said clustering comprises applying a hierarchical clustering technique, wherein said hierarchical clustering technique is an agglomerative clustering procedure.

79. The method of claim 78, wherein said agglomerative clustering procedure is a nearest-neighbor algorithm, a farthest-neighbor algorithm, an average linkage algorithm, a centroid algorithm, or a sum-of-squares algorithm.

80. The method of claim 78, wherein said hierarchical clustering technique is a divisive clustering procedure.

81. The method of claim 72 wherein an organism represents said phenotypic extreme when it is the top $30^{th}$ or bottom $30^{th}$ percentile of said population with respect to a phenotype exhibited by said population.

82. The method of claim 72 wherein an organism represents said phenotypic extreme when it is the top $10^{th}$ or bottom $10^{th}$ percentile of said population with respect to a phenotype exhibited by said population.

83. The method of claim 72 wherein said set of extreme organisms is more than 5 organisms.

84. The method of claim 72 wherein said set of extreme organisms is between 2 and 100 organisms.

85. The method of claim 72 wherein said set of extreme organisms is less than 1000 organisms.

86. The method of claim 72 wherein said identifying step (iii) comprises subjecting a plurality of cellular constituent measurements for a predetermined cellular constituent to a t-test, wherein said plurality of cellular constituent measurements is from said set of extreme organisms.

87. The method of claim 72 wherein said identifying step (iii) comprises subjecting a group of identified cellular constituents within said plurality of cellular constituents to multivariate analysis.

88. The method of claim 72 wherein said cellular constituents identified in step (iii) are reduced prior to said constructing step (iv).

89. The method of claim 88 wherein said cellular constituents identified in step (iii) are reduced by stepwise regression, all-possible-subset regression, principal component analysis, or multiple-discriminant analysis.

90. The method of claim 88 wherein said cellular constituents identified in step (iii) are reduced by a stochastic search method.

91. The method of claim 90 wherein said stochastic search method is simulated annealing or a genetic algorithm.

92. The method of claim 88 wherein said cellular constituents identified in step (iii) are reduced by clustering, wherein a cluster produced by said clustering is used in said constructing step (iv) rather than said identified cellular constituents.

93. The method of claim 72 wherein said constructing step (iv) comprises training a neural network using said probability distribution.

94. The method of claim 72 wherein said constructing step (iv) comprises using Bayesian decision theory in which said probability distribution serves as a priori information.

95. The method of claim 72 wherein said constructing step (iv) comprises using linear discriminate analysis, a linear programming algorithm, or a support vector machine.

96. The method of claim 72 wherein said classification scheme comprises classifying all or a portion of the population using said classifier.

97. A method of subdividing a plurality of organisms S of the same species in order to derive a plurality of sub-populations for use in quantitative genetic analysis, wherein a complex trait is exhibited by one or more organisms in said plurality of organisms S, the method comprising:

(a) identifying two or more groups of organisms within said plurality of organisms S that respectively represent an independent extreme with respect to said complex trait;

(b) determining a set of cellular constituents C that is able to discriminate between said two or more groups of organisms within said plurality of organisms S;

(c) performing, for each cellular constituent i in said set of cellular constituents C, QTL analysis on the cellular constituent i using, as a quantitative trait, an amount of the cellular constituent i, respectively measured from each organism in at least a portion of the plurality of organisms S, in order to identify one or more cellular constituents that have a QTL that interacts with or overlaps with a first QTL that is linked to said complex trait; and (d) clustering said plurality of organisms S based on said measured amounts of each cellular constituent identified in step (c), thereby deriving said plurality of sub-populations;

wherein said identifying step (a), said determining step (b), said performing step (c) and said clustering step (d) are executed using a suitably programmed computer.

98. The method of claim 97, wherein said first QTL linked to said complex trait is identified using linkage analysis or association analysis.

99. The method of claim 97, the method further comprising performing a series of QTL analyses on a sub-population in said plurality of sub-populations in order to identify a QTL for said complex trait, wherein each said QTL analysis in said series of QTL analyses uses measured amounts of a cellular constituent in the set of cellular constituents C as a quantitative trait, and wherein said measured amounts of said cellular constituent are respectively measured from each organism in at least a portion of said sub-population.

100. The method of claim 99, wherein a quantitative genetic analysis of said sub-population, using said complex trait as the quantitative trait, yields a linkage score for said first QTL with respect to said complex trait that is higher than the linkage score for said first QTL with respect to said complex trait that was obtained by a quantitative genetic analysis of said plurality of organisms S using said complex trait as the quantitative trait.

101. The method of claim 97, wherein each said measured amount of each said cellular constituent is determined by a transcriptional state measurement or a translational state measurement.

102. The method of claim 97, wherein a cellular constituent in said set of cellular constituents C is a metabolite and a technique used to determine said amount of the metabolite measured from each organism in at least a portion of the plurality of organisms is a cellular phenotypic technique.

103. The method of claim 102, wherein said cellular phenotypic technique comprises a metabolomic technique wherein a plurality of levels of metabolites in each said organism is measured.

104. The method of claim 102, wherein said plurality of metabolites is measured by pyrolysis mass spectrometry, Fourier-transform infrared spectrometry, Raman spectrometry, gas chromatography-mass spectroscopy, capillary electrophoresis, high pressure liquid chromatography/mass spectroscopy (HPLC/MS), liquid chromatography (LC)-electrospray mass spectroscopy, or cap-LC-tandem electrospray mass spectroscopy.

105. The method of claim 102, wherein said metabolite is an amino acid, a metal, a soluble sugar, or a complex carbohydrate.

106. The method of claim 97, wherein the amount of the cellular constituent i respectively measured from each organism in at least a portion of the plurality of organisms is an abundance of an mRNA, a protein expression level, or a metabolite level.

107. The method of claim 97, wherein said complex trait is characterized by an allele that exhibits incomplete penetrance in said plurality of organisms S.

108. The method of claim 97, wherein said complex trait is a disease that is contracted by an organism in said plurality of organisms S, and wherein said organism inherits no predisposing allele to said disease.

109. The method of claim 97, wherein said complex trait arises when any of a plurality of different genes in the genome of said species is mutated.

110. The method of claim 97, wherein said complex trait requires the simultaneous presence of mutations in a plurality of genes in the genome of said species.

111. The method of claim 97, wherein said complex trait is associated with a high frequency of disease-causing alleles in said population.

112. The method of claim 97, wherein said complex trait is a phenotype that does not exhibit Mendelian recessive or dominant inheritance attributable to a single gene locus.

113. The method of claim 97, wherein said complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, or xeroderma pigmentosum.

114. The method of claim 97, wherein said clustering step (d) uses a technique selected from the group consisting of a hierarchical cluster analysis, a non-hierarchical cluster analysis, an artificial neural network, and a self-organizing map.

115. The method of claim 114, wherein said clustering step (d) uses hierarchical cluster analysis that uses a nearest-neighbor algorithm, a farthest-neighbor algorithm, an average linkage algorithm, a centroid algorithm, or a sum-of-squares algorithm to determine the similarity between (i) the amounts of measured cellular constituents for the set of cellular constituents C from one organism in said plurality of organisms S and (ii) the amounts of measured cellular constituents for the set of cellular constituents C from another organism in said plurality of organisms S.

116. The method of claim 114, wherein said clustering step (d) uses a hierarchical cluster analysis that is selected from the group consisting of agglomerative clustering, polythetic divisive clustering, and monthetic divisive clustering.

117. The method of claim 116, wherein said hierarchical cluster analysis is agglomerative clustering using Pearson correlation coefficients, Euclidean distance, squared Euclidean distance, Euclidean sum of squares, a Manhattan metric, or squared Pearson correlation coefficients to determine similarity between (i) the cellular constituent measurements for the set of cellular constituents C from one organism in said plurality of organisms S and (ii) the cellular constituent measurements for the set of cellular constituents C from another organism in said plurality of organisms S.

118. The method of claim 114, wherein said clustering step (d) uses non-hierarchical cluster analysis that is selected from the group consisting of K-means clustering, fuzzy k-means clustering, and Jarvis-Patrick clustering.

119. The method of claim 114, wherein said clustering step (d) uses an artificial neural network that is a Kohonen artificial neural network or an auto-associative neural network.

120. The method of claim 97, wherein each respective QTL analysis in the performing step (c) comprises:
  (i) testing for linkage between a position in a chromosome, in the genome of said plurality of organisms, and the quantitative trait used in the QTL analysis;
  (ii) advancing the position in said chromosome by an amount; and
  (iii) repeating steps (i) and (ii) until the end of the chromosome is reached.

121. The method of claim 120, wherein said amount is less than 100 centiMorgans.

122. The method of claim 120, wherein said amount is less than 2.5 centiMorgans.

123. The method of claim 97, wherein said plurality of organisms S is a segregating population.

124. The method of claim 123, wherein said segregating population is selected from the group consisting of $F_2$ plants, mice derived from two inbred lines, and a human pedigree.

125. A computer program product for use in conjunction with a computer system, the computer program product comprising a computer readable storage medium and a computer program mechanism embedded therein, the computer program mechanism comprising executable instructions for performing a method comprising:
  (a) dividing a plurality of organisms in a population into a plurality of sub-populations using a classification scheme that classifies each organism in said population into at least one of said sub-populations, wherein said classification scheme is derived from a plurality of cellular constituent measurements for each of a plurality of respective cellular constituents that are from each said organism in said population; and
  (b) performing, for at least one sub-population in said plurality of sub-populations, quantitative genetic analysis on said sub-population in order to identify a quantitative trait locus for a complex trait that is exhibited by one or more organisms in said plurality of organisms.

126. The computer program product of claim 125, wherein said cellular constituent measurements from each said organism are transcriptional state measurements or translational state measurements.

127. The computer program product of claim 125, wherein said cellular constituent measurements from each said organism are translational state measurements that are performed using an antibody array or two-dimensional gel electrophoresis.

128. The computer program product of claim 125, wherein said plurality of respective cellular constituents comprises a plurality of metabolites and said plurality of cellular constituent measurements are derived by a cellular phenotypic technique.

129. The computer program product of claim 128, wherein said cellular phenotypic technique comprises a metabolomic technique wherein a plurality of levels of metabolites in each said organism is measured.

130. The computer program product of claim 129, wherein a metabolite in said plurality of metabolites comprises an amino acid, a metal, a soluble sugar, or a complex carbohydrate.

131. The computer program product of claim 129, wherein said plurality of levels of metabolites is measured by use of pyrolysis mass spectrometry, Fourier-transform infrared spectrometry, Raman spectrometry, gas chromatography-mass spectroscopy, capillary electrophoresis, high pressure liquid chromatography/mass spectroscopy (HPLC/MS), liquid chromatography (LC)-electrospray mass spectroscopy, or cap-LC-tandem electrospray mass spectroscopy.

132. The computer program product of claim 125, wherein said plurality of cellular constituent measurements comprises abundance levels of mRNA, protein expression levels, or metabolite levels.

133. The computer program product of claim 125, wherein said complex trait is characterized by an allele that exhibits incomplete penetrance in said population.

134. The computer program product of claim 125, wherein said complex trait is a disease that is contracted by an organism in said population, and wherein said organism inherits no predisposing allele to said disease.

135. The computer program product of claim 125, wherein said complex trait arises when any of a plurality of different genes in the genome of said plurality of organisms is mutated.

136. The computer program product of claim 125, wherein said complex trait requires the simultaneous presence of mutations in a plurality of genes in the genome of said plurality of organisms.

137. The computer program product of claim 125, wherein said complex trait is associated with a high frequency of disease-causing alleles in said population.

138. The computer program product of claim 125, wherein said complex trait is a phenotype that does not exhibit Mendelian recessive or dominant inheritance attributable to a single gene locus.

139. The computer program product of claim 125, wherein said complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, or xeroderma pigmentosum.

140. The computer program product of claim 125, wherein said plurality of cellular constituent measurements from each said organism comprises the measurement of the cellular constituent levels of ten or more cellular constituents in each said organism.

141. The computer program product of claim 125, wherein said plurality of cellular constituent measurements from each said organism comprises the measurement of the cellular constituent levels of one thousand or more cellular constituent levels in each said organism.

142. The computer program product of claim 125, wherein said dividing step (a) determines whether a class predictor is available, and
  when a class predictor is available, uses a supervised classification scheme to classify each organism in said population into a sub-population in said plurality of sub-populations; and
  when a class predictor is not available, uses an unsupervised classification scheme to classify each organism in said population into a sub-population in said plurality of sub-populations.

143. The computer program product of claim 125, wherein said classification scheme is a supervised classification scheme.

144. The computer program product of claim 125, wherein said classification scheme is an unsupervised classification scheme.

145. The computer program product of claim 142 or 143, wherein said supervised classification scheme uses linear discriminant analysis or a linear regression method.

146. The computer program product of claim 145, wherein said linear regression method is multiple linear regression, partial least squares regression, or principal components regression.

147. The computer program product of claim 142 or 144, wherein said unsupervised classification scheme is selected from the group consisting of a hierarchical cluster analysis, a non-hierarchical cluster analysis, an artificial neural network, and a self-organizing map.

148. The computer program product of claim 147, wherein said unsupervised classification scheme is a hierarchical cluster analysis that uses a nearest-neighbor algorithm, a farthest-neighbor algorithm, an average linkage algorithm, a centroid algorithm, or a sum-of-squares algorithm to determine the similarity between (i) the plurality of cellular constituent measurements from one organism in said plurality of organisms and (ii) the plurality of cellular constituent measurements from another organism in said plurality of organisms.

149. The computer program product of claim 147, wherein said unsupervised classification scheme is hierarchical cluster analysis selected from the group consisting of agglomerative clustering, polythetic divisive clustering, and monthetic divisive clustering.

150. The computer program product of claim 149, wherein said hierarchical cluster analysis is agglomerative clustering using Pearson correlation coefficients, Euclidean distance, squared Euclidean distance, Euclidean sum of squares, a Manhattan metric, or squared Pearson correlation coefficients to determine similarity between (i) the plurality of cellular constituent measurements from one organism in said plurality of organisms and (ii) the plurality of cellular constituent measurements from another organism in said plurality of organisms.

151. The computer program product of claim 147, wherein said unsupervised classification scheme is non-hierarchical cluster analysis selected from the group consisting of K-means clustering, fuzzy k-means clustering, and Jarvis-Patrick clustering.

152. The computer program product of claim 147, wherein said unsupervised classification scheme is an artificial neural network that is a Kohonen artificial neural network or an auto-associative neural network.

153. The computer program product of claim 125, wherein said dividing step (a) further verifies the division of said population into said plurality of sub-populations.

154. The computer program product of claim 125, wherein said performing step (b) uses a method selected from the group consisting of a linkage analysis, a quantitative trait locus (QTL) analysis method that uses said plurality of cellular constituent measurements as a phenotypic trait, and an association analysis.

155. The computer program product of claim 154, wherein said quantitative genetic analysis is performed using said QTL analysis method, said QTL analysis method comprising:
(a) clustering QTL data from a plurality of QTL analyses to form a QTL interaction map, wherein
each QTL analysis in said plurality of QTL analyses is performed for a gene G in a plurality of genes in the genome of said plurality of organisms using a genetic marker map and a quantitative trait in order to produce said QTL data, wherein, for each QTL analysis, said quantitative trait comprises an expression statistic for the gene G, for which the QTL analysis has been performed, for each organism in said plurality of organisms; and wherein
said genetic marker map is constructed from a set of genetic markers associated with said plurality of organisms; and
(b) analyzing said QTL interaction map to identify said QTL associated with said quantitative trait.

156. The computer program product of claim 155, wherein said expression statistic for said gene G is computed by a method comprising transforming an expression level measurement of said gene G from each organism in said plurality of organisms.

157. The computer program product of claim 156, wherein said step of transforming an expression level measurement of said gene G comprises normalizing the expression level measurement of said gene G in order to form said expression statistic.

158. The computer program product of claim 157, wherein normalizing the expression level measurement of said gene G in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

159. The computer program product of claim 155, wherein each said QTL analysis comprises:
(i) testing for linkage between a position in a chromosome, in the genome of said plurality of organisms, and the quantitative trait used in the QTL analysis;
(ii) advancing the position in said chromosome by an amount; and
(iii) repeating steps (i) and (ii) until the end of the chromosome is reached.

160. The computer program product of claim 159, wherein said amount is less than 100 centiMorgans.

161. The computer program product of claim 159, wherein said amount is less than 10 centiMorgans.

162. The computer program product of claim 159, wherein said amount is less than 5 centiMorgans.

163. The computer program product of claim 159, wherein said amount is less than 2.5 centiMorgans.

164. The computer program product of claim 159, wherein said QTL data produced from each respective QTL analysis comprises a statistical score computed at each said position.

165. The computer program product of claim 159, wherein a QTL vector is created for each quantitative trait tested in said chromosome, wherein said QTL vector comprises a statistical score for each position tested by the QTL analysis corresponding to the quantitative trait.

166. The computer program product of claim 165, wherein said clustering of QTL data comprises clustering each said QTL vector.

167. The computer program product of claim 165, wherein a similarity metric that is used as a basis for said clustering is a Euclidean distance, a squared Euclidean distance, a Euclidean sum of squares, a Manhattan metric, a Pearson correlation coefficient, or a squared Pearson correlation coefficient, and wherein the similarity metric is computed between QTL vector pairs.

168. The computer program product of claim 155 or 166, wherein said clustering of QTL data comprises applying a hierarchical clustering technique, applying a k-means technique, applying a fuzzy k-means technique, applying a Jarvis-Patrick clustering, applying a self-organizing map technique, or applying a neural network technique.

169. The computer program product of claim 168, wherein said clustering of QTL data comprises applying a hierarchical clustering technique, wherein said hierarchical clustering technique is an agglomerative clustering procedure.

170. The computer program product of claim 169, wherein said agglomerative clustering procedure is a nearest-neighbor algorithm, a farthest-neighbor algorithm, an average linkage algorithm, a centroid algorithm, or a sum-of-squares algorithm.

171. The computer program product of claim 168, wherein said hierarchical clustering technique is a divisive clustering procedure.

172. The computer program product of claim 156, which further comprises constructing a gene expression cluster map from each expression statistic created by said transforming step.

173. The computer program product of claim 172, wherein said constructing a gene expression cluster map comprises:
creating a plurality of gene expression vectors, each gene expression vector in said plurality of gene expression vectors representing an expression level measurement of a gene, in said plurality of genes, in each of the plurality of organisms;
computing a plurality of correlation coefficients, wherein each correlation coefficient in said plurality of correlation coefficients is computed between a gene expression vector pair in said plurality of gene expression vectors; and
clustering said plurality of gene expression vectors based on said plurality of correlation coefficients in order to form said gene expression cluster map.

174. The computer program product of claim 173, wherein said step of analyzing said QTL interaction map comprises filtering the QTL interaction map in order to obtain a candidate pathway group; and wherein the filtering comprises identifying a QTL in said candidate pathway group in said gene expression cluster map.

175. The computer program product of claim 173, wherein each correlation coefficient in said plurality of correlation coefficients is a Pearson correlation coefficient.

176. The computer program product of claim 172, wherein said constructing a gene expression cluster map comprises:
creating a plurality of gene expression vectors, each gene expression vector in said plurality of gene expression vectors representing a gene in said plurality of genes;
computing a plurality of metrics, wherein each metric in said plurality of metrics is computed between a gene expression vector pair in said plurality of gene expression vectors; and
clustering said plurality of gene expression vectors based on said plurality of metrics in order to form said gene expression cluster map.

177. The computer program product of claim 176, wherein each said metric is selected from the group consisting of a Euclidean distance, a squared Euclidean distance, a Euclidean sum of squares, a Manhattan metric, a Pearson correlation coefficient, and a squared Pearson correlation coefficient.

178. The computer program product of claim 173 or 176, wherein said clustering of the plurality of gene expression vectors comprises applying a hierarchical clustering technique, applying a k-means technique, applying a fuzzy k-means technique, applying a Jarvis-Patrick clustering, applying a self-organizing map technique, or applying a neural network technique.

179. The computer program product of claim 178, wherein said clustering of the plurality of gene expression vectors comprises applying a hierarchical clustering technique, wherein said hierarchical clustering technique is an agglomerative clustering procedure.

180. The computer program product of claim 179, wherein said agglomerative clustering procedure is a nearest-neighbor algorithm, a farthest-neighbor algorithm, an average linkage algorithm, a centroid algorithm, or a sum-of-squares algorithm.

181. The computer program product of claim 178, wherein said clustering of the plurality of gene expression vectors comprises applying a hierarchical clustering technique, wherein said hierarchical clustering technique is a divisive clustering procedure.

182. The computer program product of claim 155, wherein said step of analyzing said QTL interaction map comprises filtering the QTL interaction map in order to obtain a candidate pathway group.

183. The computer program product of claim 182, wherein said filtering in order to obtain said candidate pathway group comprises selecting those QTL for said candidate pathway group that interact most strongly with another QTL in said QTL interaction map.

184. The computer program product of claim 183, wherein said QTL that interact most strongly with another QTL in said QTL interaction map are those QTL in said QTL interaction map that share a correlation coefficient with another QTL in said quantitative trait locus interaction map that is higher than 75% of all correlation coefficients computed between QTL in said quantitative trait locus interaction map.

185. The computer program product of claim 183, wherein a multivariate statistical model is fitted to said candidate pathway group in order to test the degree to which each QTL making up the candidate pathway group belongs in the candidate pathway group.

186. The computer program product of claim 185, wherein said multivariate statistical model simultaneously considers multiple quantitative traits.

187. The computer program product of claim 185, wherein said multivariate statistical model looks for epistatic interactions between QTL in said candidate pathway group.

188. The computer program product of claim 155, wherein said set of genetic markers comprises a single nucleotide polymorphism (SNP), a microsatellite marker, a restriction fragment length polymorphism, a short tandem repeat, a DNA methylation marker, or a sequence length polymorphism.

189. The computer program product of claim 125, wherein said dividing step (a) comprises:
(i) instructions for partitioning said population into a plurality of phenotypic groups based on phenotypic data for all or a portion of said plurality of organisms;
(ii) instructions for identifying a set of extreme organisms in said plurality of phenotypic groups that represent a phenotypic extreme;
(iii) instructions for identifying cellular constituents within said plurality of cellular constituents, wherein each respective identified cellular constituent has the property that cellular constituent measurements for the respective cellular constituent from said set of extreme organisms discriminate all or a portion of said plurality of phenotypic groups; and
(iv) instructions for constructing a classifier using a probability distribution derived from all or a portion of said identified cellular constituents.

190. The computer program product of claim 189 wherein said phenotypic data comprises a binary event.

191. The computer program product of claim 189 wherein said phenotypic data comprises more than one phenotypic measurement for each organism in said population.

192. The computer program product of claim 189 wherein said phenotypic data comprises a determination as to whether each organism in said plurality of organisms exhibits a trait, and said instructions for partitioning comprise placing an organism in said plurality of organisms in a first phenotypic group when said organism exhibits said trait and placing an organism in said plurality of organisms in a second phenotypic group when said organism does not exhibit said trait.

193. The computer program product of claim 189 wherein said phenotypic data comprises a plurality of phenotypic measurements that are made for all or a portion of said plurality of organisms and wherein said instructions for partitioning comprise:
(A) instructions for constructing a plurality of phenotypic vectors, each phenotypic vector in said plurality of phenotypic vectors corresponding to an organism in said plurality of organisms and each respective phenotypic vector in said plurality of phenotypic vectors comprising a plurality of phenotypic measurements from the organism corresponding to the respective phenotypic vector; and
(B) instructions for clustering said plurality of phenotypic vectors into a plurality of clusters, wherein each cluster in said plurality of clusters represents a phenotypic group in said plurality of phenotypic groups.

194. The computer program product of claim 193 wherein said clustering comprises a hierarchical clustering technique, a k-means technique, a fuzzy k-means technique, a Jarvis-Patrick clustering, a self-organizing map technique, or a neural network technique.

195. The computer program product of claim 193, wherein said clustering comprises applying a hierarchical clustering technique, wherein said hierarchical clustering technique is an agglomerative clustering procedure.

196. The computer program product of claim 195, wherein said agglomerative clustering procedure is a nearest-neighbor algorithm, a farthest-neighbor algorithm, an average linkage algorithm, a centroid algorithm, or a sum-of-squares algorithm.

197. The computer program product of claim 195, wherein said hierarchical clustering technique is a divisive clustering procedure.

198. The computer program product of claim 189 wherein an organism represents said phenotypic extreme when it is the top $30^{th}$ or bottom $30^{th}$ percentile of said population with respect to a phenotype exhibited by said population.

199. The computer program product of claim 189 wherein an organism represents said phenotypic extreme when it is the top $10^{th}$ or bottom $10^{th}$ percentile of said population with respect to a phenotype exhibited by said population.

200. The computer program product of claim 189 wherein said set of extreme organisms is more than 5 organisms.

201. The computer program product of claim 189 wherein said set of extreme organisms is between 2 and 100 organisms.

202. The computer program product of claim 189 wherein said set of extreme organisms is less than 1000 organisms.

203. The computer program product of claim 189 wherein said instructions for identifying (iii) comprise subjecting a plurality of cellular constituent measurements for a predetermined cellular constituent to a t-test, wherein said plurality of cellular constituent measurements is from said set of extreme organisms.

204. The computer program product of claim 189 wherein said instructions for identifying comprise subjecting said identified cellular constituents to multivariate analysis.

205. The computer program product of claim 189 wherein said cellular constituents identified by said instructions for identifying (iii) are reduced prior to execution of said instructions for constructing (iv).

206. The computer program product of claim 205 wherein said cellular constituents identified by said instructions for identifying (iii) are reduced by stepwise regression, all-possible-subset regression, principal component analysis, or multiple-discriminant analysis.

207. The computer program product of claim 205 wherein said cellular constituents identified by said instructions for identifying (iii) are reduced by a stochastic search method.

208. The computer program product of claim 207 wherein said stochastic search method is simulated annealing or a genetic algorithm.

209. The computer program product of claim 205 wherein said cellular constituents identified by said instructions for identifying (iii) are reduced by clustering, wherein a cluster produced by said clustering is used by said instructions for constructing step (iv) rather than said identified cellular constituents.

210. The computer program product of claim 189 wherein said instructions for constructing (iv) comprise training a neural network using said probability distribution.

211. The computer program product of claim 189 wherein said instructions for constructing (iv) comprise using Bayesian decision theory in which said probability distribution serves as a priori information.

212. The computer program product of claim 189 wherein said instructions for constructing (iv) comprise using linear discriminate analysis, a linear programming algorithm, or a support vector machine.

213. The computer program product of claim 189 wherein said classification scheme comprises classifying all or a portion of the population using said classifier.

214. A computer program product for use in conjunction with a computer system, the computer program product comprising a computer readable storage medium and a computer program mechanism embedded therein, the computer program mechanism comprising executable instructions for performing a method comprising:
    subdividing a plurality of organisms S of the same species in order to derive a plurality of sub-populations for use in quantitative genetic analysis, wherein a complex trait is exhibited by one or more organisms in said plurality of organisms S, the method comprising
    (a) identifying two or more groups of organisms within said plurality of organisms S that respectively represent an independent extreme with respect to said complex trait;
    (b) determining a set of cellular constituents C that is able to discriminate between said two or more groups of organisms within said plurality of organisms S;
    (c) performing, for each cellular constituent i in said set of cellular constituents C, QTL analysis on the cellular constituent i using, as a quantitative trait, an amount of the cellular constituent i, respectively measured from each organism in at least a portion of the plurality of organisms S, in order to identify one or more cellular constituents that have a QTL that interacts with or overlaps with a first QTL that is linked to said complex trait; and
    (d) clustering said plurality of organisms S based on said measured amounts of each cellular constituent identified by said performing step (c), thereby deriving said plurality of sub-populations.

215. The computer program product of claim 214, wherein said first QTL linked to said complex trait is identified using linkage analysis or association analysis.

216. The computer program product of claim 215, the method further comprising performing a series of QTL analyses on a sub-population in said plurality of sub-populations in order to identify a QTL for said complex trait, wherein each said QTL analysis in said series of QTL analyses uses measured amounts of a cellular constituent in the set of cellular constituents C as a quantitative trait, and wherein said measured amounts of said cellular constituent are respectively measured from each organism in at least a portion of said sub-population.

217. The computer program product of claim 216, wherein a quantitative genetic analysis of said sub-population, using said complex trait as the quantitative trait, yields a linkage score for said first QTL with respect to said complex trait that is higher than the linkage score for said first QTL with respect to said complex trait that was obtained by a quantitative genetic analysis of said plurality of organisms S using said complex trait as the quantitative trait.

218. The computer program product of claim 214, wherein each said measured amount of each said cellular constituent is determined by a transcriptional state measurement or a translational state measurement.

219. The computer program product of claim 214, wherein a cellular constituent in said set of cellular constituents C is a metabolite and a technique used to determine said amount of the metabolite measured from each organism in at least a portion of the plurality of organisms is a cellular phenotypic technique.

220. The computer program product of claim 219, wherein said cellular phenotypic technique comprises a metabolomic technique wherein a plurality of levels of metabolites in each said organism is measured.

221. The computer program product of claim 219, wherein said plurality of metabolites is measured by pyrolysis mass spectrometry, Fourier-transform infrared spectrometry, Raman spectrometry, gas chromatography-mass spectroscopy, capillary electrophoresis, high pressure liquid chromatography/mass spectroscopy (HPLC/MS), liquid chromatography (LC)-electrospray mass spectroscopy, or cap-LC-tandem electrospray mass spectroscopy.

222. The computer program product of claim 219, wherein said metabolite is an amino acid, a metal, a soluble sugar, or a complex carbohydrate.

223. The computer program product of claim 214, wherein the amount of the cellular constituent i respectively measured from each organism in at least a portion of the plurality of organisms is an abundance of an mRNA, a protein expression level, or a metabolite level.

224. The computer program product of claim 214, wherein said complex trait is characterized by an allele that exhibits incomplete penetrance in said plurality of organisms S.

225. The computer program product of claim 214, wherein said complex trait is a disease that is contracted by an organism in said plurality of organism S, and wherein said organism inherits no predisposing allele to said disease.

226. The computer program product of claim 214, wherein said complex trait arises when any of a plurality of different genes in the genome of said species is mutated.

227. The computer program product of claim 214, wherein said complex trait requires the simultaneous presence of mutations in a plurality of genes in the genome of said species.

228. The computer program product of claim 214, wherein said complex trait is associated with a high frequency of disease-causing alleles in said population.

229. The computer program product of claim 214, wherein said complex trait is a phenotype that does not exhibit Mendelian recessive or dominant inheritance attributable to a single gene locus.

230. The computer program product of claim 214, wherein said complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, or xeroderma pigmentosum.

231. The computer program product of claim 214, wherein said clustering step (d) uses a technique selected from the group consisting of a hierarchical cluster analysis, a non-hierarchical cluster analysis, an artificial neural network, and a self-organizing map.

232. The computer program product of claim 231, wherein said clustering step (d) uses hierarchical cluster analysis that uses a nearest-neighbor algorithm, a farthest-neighbor algorithm, an average linkage algorithm, a centroid algorithm, or a sum-of-squares algorithm to determine the similarity between (i) the amounts of measured cellular constituents for the set of cellular constituents C from one organism in said plurality of organisms S and (ii) the amounts of measured cellular constituents for the set of cellular constituents C from another organism in said plurality of organisms S.

233. The computer program product of claim 231, wherein said clustering step (d) uses a hierarchical cluster analysis that is selected from the group consisting of agglomerative clustering, polythetic divisive clustering, and monthetic divisive clustering.

234. The computer program product of claim 233, wherein said hierarchical cluster analysis is agglomerative clustering using Pearson correlation coefficients, Euclidean distance, squared Euclidean distance, Euclidean sum of squares, a Manhattan metric, or squared Pearson correlation coefficients to determine similarity between (i) the cellular constituent measurements for the set of cellular constituents C from one organism in said plurality of organisms S and (ii) the cellular constituent measurements for the set of cellular constituents C from another organism in said plurality of organisms S.

235. The computer program product of claim 231, wherein said clustering step (d) uses non-hierarchical cluster analysis that is selected from the group consisting of K-means clustering, fuzzy k-means clustering, and Jarvis-Patrick clustering.

236. The computer program product of claim 231, wherein said clustering step (d) uses an artificial neural network that is a Kohonen artificial neural network or an auto-associative neural network.

237. The computer program product of claim 214, wherein each respective QTL analysis, computed by said performing step (c), comprises:

(i) testing for linkage between a position in a chromosome, in the genome of said plurality of organisms, and the quantitative trait used in the QTL analysis;
(ii) advancing the position in said chromosome by an amount; and
(iii) repeating steps (i) and (ii) until the end of the chromosome is reached.

238. The computer program product of claim 237, wherein said amount is less than 100 centiMorgans.

239. The computer program product of claim 237, wherein said amount is less than 10 centiMorgans.

240. The computer program product of claim 237, wherein said amount is less than 5 centiMorgans.

241. The computer program product of claim 237, wherein said amount is less than 2.5 centiMorgans.

242. The computer program product of claim 214, wherein said plurality of organisms S is a segregating population.

243. The computer program product of claim 242, wherein said segregating population is selected from the group consisting of $F_2$ plants, mice derived from two inbred lines, and a human pedigree.

244. A computer system for identifying a quantitative trait locus for a complex trait that is exhibited by a plurality of organisms in a population, the computer system comprising:
a central processing unit;
a memory, coupled to the central processing unit, the memory storing a classification module and a quantitative genetic analysis module that cause the central processing unit to perform a method comprising:
(a) dividing said population into a plurality of sub-populations using a classification scheme that classifies each organism in said population into at least one of said sub-populations, wherein said classification scheme is derived from a plurality of cellular constituents measurements for each of a plurality of respective cellular constituents that are from each said organism in said population; and
(b) performing, for at least one sub-population in said plurality of sub-populations, quantitative genetic analysis on said sub-population in order to identify said quantitative trait locus for said complex trait.

245. The computer system of claim 244, wherein said cellular constituent measurements from each said organism are transcriptional state measurements or translational state measurements.

246. The computer system of claim 245, wherein said translational state measurements are performed using an antibody array or two-dimensional gel electrophoresis.

247. The computer system of claim 244, wherein said plurality of respective cellular constituents comprises a plurality of metabolites and said plurality of cellular constituent measurements are derived by a cellular phenotypic technique.

248. The computer system of claim 247, wherein said cellular phenotypic technique comprises a metabolomic technique wherein a plurality of levels of metabolites in each said organism is measured.

249. The computer system of claim 248, wherein a metabolite in said plurality of metabolites comprises an amino acid, a metal, a soluble sugar, or a complex carbohydrate.

250. The computer system of claim 248, wherein said plurality of levels of metabolites is measured by pyrolysis mass spectrometry, Fourier-transform infrared spectrometry, Raman spectrometry, gas chromatography-mass spectroscopy, capillary electrophoresis, high pressure liquid chromatography/mass spectroscopy (HPLC/MS), liquid chromatography (LC)-electrospray mass spectroscopy, or cap-LC-tandem electrospray mass spectroscopy.

251. The computer system of claim 244, wherein said plurality of cellular constituent measurements comprise abundance levels of mRNA, protein expression levels, or metabolite levels.

252. The computer system of claim 244, wherein said complex trait is characterized by an allele that exhibits incomplete penetrance in said population.

253. The computer system of claim 244, wherein said complex trait is a disease that is contracted by an organism in said population, and wherein said organism inherits no predisposing allele to said disease.

254. The computer system of claim 244, wherein said complex trait arises when any of a plurality of different genes in the genome of said plurality of organisms is mutated.

255. The computer system of claim 244, wherein said complex trait requires the simultaneous presence of mutations in a plurality of genes in the genome of said plurality of organisms.

256. The computer system of claim 244, wherein said complex trait is associated with a high frequency of disease-causing alleles in said population.

257. The computer system of claim 244, wherein said complex trait is a phenotype that does not exhibit Mendelian recessive or dominant inheritance attributable to a single gene locus.

258. The computer system of claim 244, wherein said complex trait is susceptibility to heart disease, hypertension, diabetes, cancer, infection, polycystic kidney disease, early-onset Alzheimer's disease, maturity-onset diabetes of the young, hereditary nonpolyposis colon cancer, ataxia telangiectasia, obesity, or xeroderma pigmentosum.

259. The computer system of claim 244, wherein said plurality of cellular constituent measurements from each said organism comprises the measurement of the cellular constituent levels of ten or more cellular constituents in each said organism.

260. The computer system of claim 244, wherein said plurality of cellular constituent measurements from each said organism comprises the measurement of the cellular constituent levels of one thousand or more cellular constituent levels in each said organism.

261. The computer system of claim 244, the method further comprising determining whether a class predictor is available, and
when a class predictor is available, using a supervised classification scheme to classify each organism in said population into a sub-population in said plurality of sub-populations; and
when a class predictor is not available, using an unsupervised classification scheme to classify each organism in said population into a sub-population in said plurality of sub-populations.

262. The computer system of claim 244, wherein said classification scheme is a supervised classification scheme.

263. The computer system of claim 244, wherein said classification scheme is an unsupervised classification scheme.

264. The computer system of claim 261 or 262, wherein said supervised classification scheme uses linear discriminant analysis or a linear regression method.

265. The computer system of claim 264, wherein said supervised classification scheme uses a linear regression method that uses multiple linear regression, partial least squares regression, or principal components regression.

266. The computer system of claim 261 or 263, wherein said unsupervised classification scheme is selected from the group consisting of a hierarchical cluster analysis, a non-hierarchical cluster analysis, an artificial neural network, and a self-organizing map.

267. The computer system of claim 266, wherein said unsupervised classification scheme is a hierarchical cluster analysis that uses a nearest-neighbor algorithm, a farthest-neighbor algorithm, an average linkage algorithm, a centroid algorithm, or a sum-of-squares algorithm to determine the similarity between (i) the plurality of cellular constituent measurements from one organism in said plurality of organisms and (ii) the plurality of cellular constituent measurements from another organism in said plurality of organisms.

268. The computer system of claim 266, wherein said unsupervised classification scheme is a hierarchical cluster analysis selected from the group consisting of agglomerative clustering, polythetic divisive clustering, and monthetic divisive clustering.

269. The computer system of claim 268, wherein said hierarchical cluster analysis is an agglomerative clustering using Pearson correlation coefficients, Euclidean distance, squared Euclidean distance, Euclidean sum of squares, a Manhattan metric, or squared Pearson correlation coefficients to determine similarity between (i) the plurality of cellular constituent measurements from one organism in said plurality of organisms and (ii) the plurality of cellular constituent measurements from another organism in said plurality of organisms.

270. The computer system of claim 266, wherein said unsupervised classification scheme is a non-hierarchical cluster analysis selected from the group consisting of K-means clustering, fuzzy k-means clustering, and Jarvis-Patrick clustering.

271. The computer system of claim 266, wherein said unsupervised classification scheme is an artificial neural network that is a Kohonen artificial neural network or an auto-associative neural network.

272. The computer system of claim 244, wherein-said method further comprises verifying the division of said population into said plurality of sub-populations.

273. The computer system of claim 244, wherein said performing step (b) uses a method selected from the group consisting of a linkage analysis, a quantitative trait locus (QTL) analysis method that uses said plurality of cellular constituent measurements as a phenotypic trait, and an association analysis.

274. The computer system of claim 273, wherein said quantitative genetic analysis is performed using said QTL analysis method, said QTL analysis method comprising:
(a) clustering QTL data from a plurality of QTL analyses to form a QTL interaction map, wherein
each QTL analysis in said plurality of QTL analyses is performed for a gene G in a plurality of genes in the genome of said plurality of organisms using a genetic marker map and a quantitative trait in order to produce said QTL data, wherein, for each QTL analysis, said quantitative trait comprises an expression statistic for the gene G, for which the QTL analysis has been performed, for each organism in said plurality of organisms; and wherein
said genetic marker map is constructed from a set of genetic markers associated with said plurality of organisms; and
(b) analyzing said QTL interaction map to identify said QTL associated with said quantitative trait.

275. The computer system of claim 274, wherein said expression statistic for said gene G is computed by a method comprising transforming an expression level measurement of said gene G from each organism in said plurality of organisms.

276. The computer system of claim 275, wherein said step of transforming an expression level measurement of said gene G comprises normalizing the expression level measurement of said gene G in order to form said expression statistic.

277. The computer system of claim 276, wherein normalizing the expression level measurement of said gene G in order to form said expression statistic is performed by a normalization technique selected from the group consisting of Z-score of intensity, median intensity, log median intensity, Z-score standard deviation log of intensity, Z-score mean absolute deviation of log intensity, calibration DNA gene set, user normalization gene set, ratio median intensity correction, and intensity background correction.

278. The computer system of claim 274, wherein each said QTL analysis comprises:
   (i) testing for linkage between a position in a chromosome, in the genome of said plurality of organisms, and the quantitative trait used in the QTL analysis;
   (ii) advancing the position in said chromosome by an amount; and
   (iii) repeating steps (i) and (ii) until the end of the chromosome is reached.

279. The computer system of claim 278, wherein said amount is less than 100 centiMorgans.

280. The computer system of claim 278, wherein said amount is less than 10 centiMorgans.

281. The computer system of claim 278, wherein said amount is less than 5 centiMorgans.

282. The computer system of claim 278, wherein said amount is less than 2.5 centiMorgans.

283. The computer system of claim 278, wherein said QTL data produced from each respective QTL analysis comprises a statistical score computed at each said position.

284. The computer system of claim 278, wherein a QTL vector is created for each quantitative trait tested in said chromosome thereby forming a plurality of QTL vectors, wherein each QTL vector in said plurality of QTL vectors comprises a statistical score for each position tested by the QTL analysis corresponding to the quantitative trait.

285. The computer system of claim 284, wherein said clustering of QTL data comprises clustering each said QTL vector in said plurality of QTL vectors.

286. The computer system of claim 284, wherein a similarity metric is used as a basis for said clustering, wherein said similarity metric is a Euclidean distance, a squared Euclidean distance, a Euclidean sum of squares, a Manhattan metric, a Pearson correlation coefficient, or a squared Pearson correlation coefficient, and wherein the similarity metric is computed between QTL vector pairs in said plurality of QTL vectors.

287. The computer system of claim 274 or 285, wherein said clustering of QTL data comprises applying a hierarchical clustering technique, applying a k-means technique, applying a fuzzy k-means technique, applying a Jarvis-Patrick clustering, applying a self-organizing map technique, or applying a neural network technique.

288. The computer system of claim 287, wherein said clustering of QTL data comprises applying a hierarchical clustering technique, wherein said hierarchical clustering technique is an agglomerative clustering procedure.

289. The computer system of claim 288, wherein said agglomerative clustering procedure is a nearest-neighbor algorithm, a farthest-neighbor algorithm, an average linkage algorithm, a centroid algorithm, or a sum-of-squares algorithm.

290. The computer system of claim 287, wherein said clustering of QTL data comprises said hierarchical clustering technique and wherein said hierarchical clustering technique is a divisive clustering procedure.

291. The computer system of claim 275, further comprising constructing a gene expression cluster map from each expression statistic created by said transforming step.

292. The computer system of claim 291, wherein said constructing a gene expression cluster map comprises:
   creating a plurality of gene expression vectors, each gene expression vector in said plurality of gene expression vectors representing an expression level measurement of a gene, in said plurality of genes, in each of the plurality of organisms;
   computing a plurality of correlation coefficients, wherein each correlation coefficient in said plurality of correlation coefficients is computed between a gene expression vector pair in said plurality of gene expression vectors; and
   clustering said plurality of gene expression vectors based on said plurality of correlation coefficients in order to form said gene expression cluster map.

293. The computer system of claim 292, wherein said step of analyzing said QTL interaction map comprises filtering the QTL interaction map in order to obtain a candidate pathway group; and wherein the filtering comprises identifying a QTL in said candidate pathway group in said gene expression cluster map.

294. The computer system of claim 292, wherein each correlation coefficient in said plurality of correlation coefficients is a Pearson correlation coefficient.

295. The computer system of claim 292, wherein said constructing a gene expression cluster map comprises:
   creating a plurality of gene expression vectors, each gene expression vector in said plurality of gene expression vectors representing a gene in said plurality of genes;
   computing a plurality of metrics, wherein each metric in said plurality of metrics is computed between a gene expression vector pair in said plurality of gene expression vectors; and
   clustering said plurality of gene expression vectors based on said plurality of metrics in order to form said gene expression cluster map.

296. The computer system of claim 295, wherein each said metric is selected from the group consisting of a Euclidean distance, a squared Euclidean distance, a Euclidean sum of squares, a Manhattan metric, a Pearson correlation coefficient, and a squared Pearson correlation coefficient.

297. The computer system of claim 295, wherein said clustering of the plurality of gene expression vectors comprises applying a hierarchical clustering technique, applying a k-means technique, applying a fuzzy k-means technique, applying a Jarvis-Patrick clustering, applying a self-organizing map technique, or applying a neural network technique.

298. The computer system of claim 297, wherein said clustering of the plurality of gene expression vectors comprises applying a hierarchical clustering technique, wherein said hierarchical clustering technique is an agglomerative clustering procedure.

299. The computer system of claim 298, wherein said agglomerative clustering procedure is a nearest-neighbor algorithm, a farthest-neighbor algorithm, an average linkage algorithm, a centroid algorithm, or a sum-of-squares algorithm.

300. The computer system of claim 297, wherein said clustering of the plurality of gene expression vectors comprises applying a hierarchical clustering technique, wherein said hierarchical clustering technique is a divisive clustering procedure.

301. The computer system of claim 274, wherein said step of analyzing said QTL interaction map comprises filtering the QTL interaction map in order to obtain a candidate pathway group.

302. The computer system of claim 301, wherein said filtering in order to obtain said candidate pathway group comprises selecting those QTL for said candidate pathway group that interact most strongly with another QTL in said QTL interaction map.

303. The computer system of claim 302, wherein those QTL for said candidate pathway group that interact most strongly with another QTL in said QTL interaction map are deemed to be those QTL in said QTL interaction map that share a correlation coefficient with another QTL in said quantitative trait locus interaction map that is higher than 75% of all correlation coefficients computed between QTL in said QTL interaction map.

304. The computer system of claim 302, wherein a multivariate statistical model is fitted to said candidate pathway group in order to test the degree to which each QTL making up the candidate pathway group belongs in the candidate pathway group.

305. The computer system of claim 304, wherein said multivariate statistical model simultaneously considers multiple quantitative traits.

306. The computer system of claim 304, wherein said multivariate statistical model looks for epistatic interactions between QTL in said candidate pathway group.

307. The computer system of claim 274, wherein said set of genetic markers comprises a single nucleotide polymorphism (SNP), a microsatellite marker, a restriction fragment length polymorphism, a short tandem repeat, a DNA methylation marker, or a sequence length polymorphism.

308. The computer system of claim 244, wherein said dividing step (a) comprises:
   (i) partitioning said population into a plurality of phenotypic groups based on phenotypic data for all or a portion of said plurality of organisms;
   (ii) identifying a set of extreme organisms in said plurality of phenotypic groups that represent a phenotypic extreme;
   (iii) for identifying cellular constituents within said plurality of cellular constituents, wherein each respective identified cellular constituent has the property that cellular constituent measurements for the respective cellular constituent from said set of extreme organisms discriminate all or a portion of said plurality of phenotypic groups; and
   (iv) constructing a classifier using a probability distribution derived from all or a portion of said identified cellular constituents.

309. The computer system of claim 308 wherein said phenotypic data comprises a binary event.

310. The computer system of claim 308 wherein said phenotypic data comprises more than one phenotypic measurement for each organism in said population.

311. The computer system of claim 308 wherein said phenotypic data comprises a determination as to whether each organism in said plurality of organisms exhibits a trait, and said partitioning step (i) comprises placing an organism in said plurality of organisms in a first phenotypic group when said organism exhibits said trait and placing an organism in said plurality of organisms in a second phenotypic group when said organism does not exhibit said trait.

312. The computer system of claim 308 wherein said phenotypic data comprises a plurality of phenotypic measurements that are made for all or a portion of said plurality of organisms and wherein said partitioning step (i) comprises:
   (A) constructing a plurality of phenotypic vectors, each phenotypic vector in said plurality of phenotypic vectors corresponding to an organism in said plurality of organisms and each respective phenotypic vector in said plurality of phenotypic vectors comprising a plurality of phenotypic measurements from the organism corresponding to the respective phenotypic vector; and
   (B) clustering said plurality of phenotypic vectors into a plurality of clusters, wherein each cluster in said plurality of clusters represents a phenotypic group in said plurality of phenotypic groups.

313. The computer system of claim 312 wherein said clustering step (B) comprises a hierarchical clustering technique, a k-means technique, a fuzzy k-means technique, a Jarvis-Patrick clustering, a self-organizing map technique, or a neural network technique.

314. The computer system of claim 312, wherein said clustering step (B) comprises applying a hierarchical clustering technique, wherein said hierarchical clustering technique is an agglomerative clustering procedure.

315. The computer system of claim 314, wherein said agglomerative clustering procedure is a nearest-neighbor algorithm, a farthest-neighbor algorithm, an average linkage algorithm, a centroid algorithm, or a sum-of-squares algorithm.

316. The computer system of claim 312, wherein said hierarchical clustering technique is a divisive clustering procedure.

317. The computer system of claim 308 wherein an organism represents said phenotypic extreme when it is the top $30^{th}$ or bottom $30^{th}$ percentile of said population with respect to a phenotype exhibited by said population.

318. The computer system of claim 308 wherein an organism represents said it th phenotypic extreme when is the top $10^{th}$ or bottom $10^{th}$ percentile of said population with respect to a phenotype exhibited by said population.

319. The computer system of claim 308 wherein said set of extreme organisms is more than 5 organisms.

320. The computer system of claim 308 wherein said set of extreme organisms is between 2 and 100 organisms.

321. The computer system of claim 308 wherein said set of extreme organisms is less than 1000 organisms.

322. The computer system of claim 308 wherein said identifying step (iii) comprises subjecting a plurality of cellular constituent measurements for a predetermined cellular constituent to a t-test, wherein said plurality of cellular constituent measurements are from said set of extreme organisms.

323. The computer system of claim 308 wherein said identifying step (iii) comprises subjecting said identified cellular constituents to multivariate analysis.

324. The computer system of claim 308 wherein said cellular constituents identified by said identifying step (iii) are reduced prior to execution of said constructing step (iv).

325. The computer system of claim 324 wherein said cellular constituents identified by said identifying step (iii) are reduced by stepwise regression, all-possible-subset regression, principal component analysis, or multiple-discriminant analysis.

326. The computer system of claim 324 wherein said cellular constituents identified by said identifying step (iii) are reduced by a stochastic search method.

327. The computer system of claim 326 wherein said stochastic search method is simulated annealing or a genetic algorithm.

328. The computer system of claim 324 wherein said cellular constituents identified by said identifying step (iii) are reduced by clustering, wherein a cluster produced by said clustering is used by said constructing step (iv) rather than said cellular constituents identified by said identifying step (iii).

329. The computer system of claim 308 wherein said constructing step (iv) comprises training a neural network using said probability distribution.

330. The computer system of claim 308 wherein said constructing step (iv) comprises using Bayesian decision theory in which said probability distribution serves as a priori information.

331. The computer system of claim 308 wherein said constructing step (iv) comprises using linear discriminate analysis, a linear programming algorithm, or a support vector machine.

332. The computer system of claim 308 wherein said classification scheme comprises classifying all or a portion of the population using said classifier.

333. A computer system for subdividing a plurality of organisms S of the same species in order to derive a plurality of sub-populations for use in quantitative genetic analysis, wherein a complex trait is exhibited by one or more organisms in said plurality of organisms S, the computer system comprising:
   a central processing unit; and
   a memory, coupled to the central processing unit, the memory storing a classification module; wherein the classification module causes the central processing unit to perform a method comprising:
   (a) identifying two or more groups of organisms within said plurality of organisms S that respectively represent an independent extreme with respect to said complex trait;
   (b) determining a set of cellular constituents C that is able to discriminate between said two or more groups of organisms within said plurality of organisms S;
   (c) performing, for each cellular constituent i in said set of cellular constituents C, QTL analysis on the cellular constituent i using, as a quantitative trait, an amount of the cellular constituent i, respectively measured from each organism in at least a portion of the plurality of organisms S, in order to identify one or more cellular constituents that have a QTL that interacts with or overlaps with a first QTL that is linked to said complex trait; and
   (d) clustering said plurality of organisms S based on measured amounts of each cellular constituent identified by said performing step (c), thereby deriving said plurality of sub-populations.

* * * * *

UNITED STATES PATENT AND TRADEMARK OFFICE
CERTIFICATE OF CORRECTION

PATENT NO. : 7,653,491 B2
APPLICATION NO. : 10/515804
DATED : January 26, 2010
INVENTOR(S) : Schadt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 886 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,653,491 B2
APPLICATION NO. : 10/515804
DATED : January 26, 2010
INVENTOR(S) : E. E. Schadt et al.

It is certified that error appears in the above-identified patent and that said Letters Patent is hereby corrected as shown below:

| COLUMN | LINE | |
|---|---|---|
| 96 (Claim 16, | 16 line 4) | "often or more" should read --of ten or more-- |
| 98 (Claim 37, | 4 line 4) | "quantitative-trait" should read --quantitative trait-- |
| 120 (Claim 318, | 40 line 2) | after "represents said" delete "it th" |

Signed and Sealed this
Twenty-fifth Day of January, 2011

David J. Kappos
*Director of the United States Patent and Trademark Office*